United States Patent
Ohwada et al.

(10) Patent No.: US 9,469,665 B2
(45) Date of Patent: Oct. 18, 2016

(54) COMPOUND HAVING LYSOPHOSPHATIDYLSERINE RECEPTOR FUNCTION MODULATION ACTIVITY

(71) Applicants: THE UNIVERSITY OF TOKYO, Tokyo (JP); TOHOKU UNIVERSITY, Sendai-shi, Miyagi (JP)

(72) Inventors: Tomohiko Ohwada, Tokyo (JP); Yuko Otani, Tokyo (JP); Masaya Ikubo, Tokyo (JP); Sho Nakamura, Tokyo (JP); Sejin Jung, Tokyo (JP); Junken Aoki, Miyagi (JP); Kumiko Makide, Miyagi (JP); Asuka Inoue, Miyagi (JP)

(73) Assignees: THE UNIVERSITY OF TOKYO, Tokyo (JP); TOHOKU UNIVERSITY, Sendai-Shi (JP)

( * ) Notice: Subject to any disclaimer, the term of this patent is extended or adjusted under 35 U.S.C. 154(b) by 0 days.

(21) Appl. No.: 14/764,808

(22) PCT Filed: Jan. 30, 2014

(86) PCT No.: PCT/JP2014/052053
§ 371 (c)(1),
(2) Date: Jul. 30, 2015

(87) PCT Pub. No.: WO2014/119649
PCT Pub. Date: Aug. 7, 2014

(65) Prior Publication Data
US 2015/0361119 A1   Dec. 17, 2015

(30) Foreign Application Priority Data
Jan. 31, 2013  (JP) ................................. 2013-017817

(51) Int. Cl.
C07F 9/09  (2006.01)
C07F 9/655  (2006.01)

(52) U.S. Cl.
CPC ............... *C07F 9/6552* (2013.01); *C07F 9/09* (2013.01); *C07F 9/091* (2013.01)

(58) Field of Classification Search
CPC combination set(s) only.
See application file for complete search history.

(56) References Cited

U.S. PATENT DOCUMENTS

| | | | |
|---|---|---|---|
| 8,058,402 B2 | 11/2011 | Granger et al. | |
| 8,461,307 B2 | 6/2013 | Granger et al. | |
| 8,974,787 B2 | 3/2015 | Granger et al. | |
| 2009/0304577 A1 | 12/2009 | Matossian-Rogers | |
| 2010/0021466 A1 | 1/2010 | Granger et al. | |
| 2010/0130737 A1 | 5/2010 | Itoh et al. | |
| 2012/0076798 A1 | 3/2012 | Granger et al. | |
| 2013/0230536 A1 | 9/2013 | Granger et al. | |

FOREIGN PATENT DOCUMENTS

| | | |
|---|---|---|
| EP | 0 396 080 A2 | 11/1990 |
| EP | 1 849 465 A1 | 10/2007 |
| JP | 2-306982 A | 12/1990 |
| JP | 2007-267601 A | 10/2007 |
| JP | 2007-284402 A | 11/2007 |
| JP | 2009-505640 A | 2/2009 |
| JP | 2010-502183 A | 1/2010 |
| JP | 2010-184867 A | 8/2010 |
| WO | WO 2006/088246 A1 | 8/2006 |
| WO | WO 2007/017686 A2 | 2/2007 |
| WO | WO 2008/027338 A2 | 3/2008 |
| WO | WO 2012/157746 A1 | 11/2012 |

OTHER PUBLICATIONS

Majumdar et al., caplus an 2005:96998, 2005.*
English translation of International Search Report mailed May 13, 2014, in PCT International Application No. PCT/JP2014/052053.
English translation of Written Opinion mailed May 13, 2014, in PCT International Application No. PCT/JP2014/052053.
Inoue et al., "TFGα shedding assay: an accurate and versatile method for detecting GPCR activation," Nature Methods (Oct. 2012), vol. 9, No. 10, pp. 1021-1029.
Kitamura et al., "GPR34 is a receptor for lysophosphatidylserine with a fatty acid at the sn-2 position," J. Biochem. (2012), vol. 151, No. 5, pp. 511-518.
Martin, T. W. and D. Lagunoff, "Interactions of lysophospholipids and mast cells," Nature (May 17, 1979), vol. 279, pp. 250-252.
Pajouhesh, H. and A. J. Hancock, "Synthesis of conformationally restricted acidic lipids. I. Cyclopentanoid analogs of phosphatidylersine," Journal of Lipid Research (1983), vol. 24, pp. 645-651.
Smith et al., "The exogenous lipid requirement for histamine release from rat peritoneal mast cells stimulated by concanavalin A," FEBS Letters (Sep. 1979), vol. 105, No. 1, pp. 58-62.
Tokumra, A., "Physiological Significance of Lysophospholipids that Act on the Lumen Side of Mammalian Lower Digestive Tracts," Journal of Health Science (2011), vol. 57, No. 2, pp. 115-128.

* cited by examiner

*Primary Examiner* — Sun Jae Yoo
(74) *Attorney, Agent, or Firm* — Birch, Stewart, Kolasch & Birch, LLP

(57) ABSTRACT

The object of the present invention is to provide a compound having a lysophosphatidylserine receptor function modulation activity or a salt thereof.
A compound having a lysophosphatidylserine receptor function modulation activity or a salt thereof, or a pharmaceutical composition or a lysophosphatidylserine receptor function moderator containing such compound or salt is provided by the present invention.

9 Claims, 1 Drawing Sheet

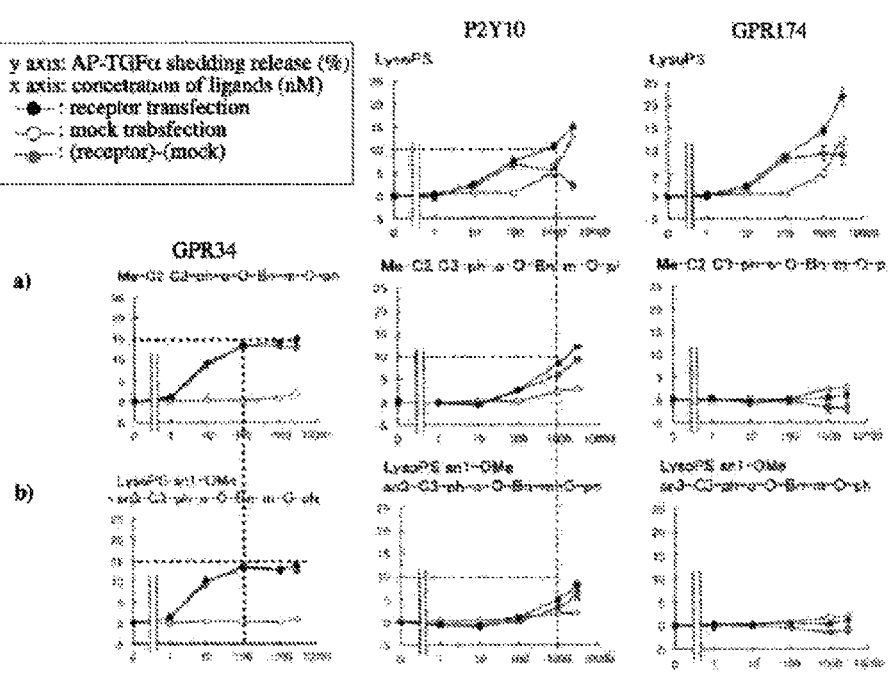

COMPOUND HAVING LYSOPHOSPHATIDYLSERINE RECEPTOR FUNCTION MODULATION ACTIVITY

TECHNICAL FIELD

The present invention relates to a compound having a lysophosphatidylserine receptor function modulation activity or a salt thereof. In addition, the present invention relates to a pharmaceutical composition or a lysophosphatidylserine receptor function modulator containing said compound or salt thereof.

BACKGROUND ART

Lysophospholipid is a collective name of phospholipids containing a single acyl group. Lysophospholipids have lower hydrophobicity than diacyl phospholipids, major components of the cell membrane, and they can be readily liberated from the cell membrane. It has been known that some lysophospholipids serve as signal molecules between cells or membranes and play important roles in the living organisms. In addition, it has been conventionally known that, when an inflammation such as tissue injury develops, phospholipids in a biomembrane are hydrolyzed to generate lysophospholipids (Patent Document 1). Lysophosphatidylserine (LysoPS), a type of lysophospholipid, has shown to be involved in acute inflammation by inducing degranulation of mast cells (Non-Patent Documents 1 and 2). The G protein-coupled receptors, GPR34, P2Y10, A630033H20Rik, and GPR174, have been identified as LysoPS receptors (Non-Patent Document 3); among these receptors, GPR34, P2Y10, and GPR174 are respectively referred to as $LPS_1$, $LPS_2$, and $LPS_3$ (Non-Patent Document 4). It has been reported that $LPS_1$ is involved in signal transduction for inducing or enhancing the degranulation reaction of mast cells, and it can be a target in the treatment of allergic diseases or chronic inflammation diseases (Patent Documents 1 and 2). Further, a specific lysophosphatidylserine derivative (lysophosphatidylthreonine) is known to dramatically accelerate degranulation reaction of mast cells (Patent Documents 3 and 4).

A screening method for compounds which are useful as autoimmune therapeutic agents as well as lysophosphatidylserine and its derivative that were found by the screening method have been reported (Patent Document 5). An autoimmune disease is a collective name of diseases in which the immune system, which is originally a protective system against foreign matters, overreacts and attacks a person's own normal cells and tissues such that symptoms appear. An autoimmune disease can be categorized into two types: a systemic autoimmune disease that affects the entire body, and an organ specific disease that affects only specific organs. In general, an autoimmune disease tends to be a chronic disease or an intractable disease, and some are identified in the list of Specified Disease Treatment Research Program by the Ministry of Health, Labour and Welfare. Numerous studies have been conducted on treatment methods of autoimmune diseases, and examples of those reported include a treatment method of chronic inflammation due to autoimmune disease, using a cytokine specific antibody involved in inflammation (Patent Document 6), and a treatment method of diseases by neutralizing the pathogenic autoantibody (Patent Document 7). However, much are left unanswered concerning the cause of autoimmune diseases, and establishment of effective therapeutic methods is awaited for many autoimmune diseases. A pharmaceutical agent for suppressing immunological systems or an anti-inflammatory agent for mitigating inflammation (a steroid or non-steroid agent) is used as a primary selection agent for autoimmune diseases.

CITATION LIST

Patent Documents

Patent Document 1: Japanese patent publication No. 2007-267601
Patent Document 2: WO 2006/088246
Patent Document 3: Japanese patent publication No. 2007-284402
Patent Document 4: Japanese patent publication No. 2010-184867
Patent Document 5: WO 2012/157746
Patent Document 6: Japanese domestic publication No. 2010-502183
Patent Document 7: Japanese domestic publication No. 2009-505640

Non-Patent Documents

Non-Patent Document 1: Nature, Vol. 279, p 250-252 (1979)
Non-Patent Document 2: J. C. FEBS Lett., Vol. 105, p 58-62 (1979)
Non-Patent Document 3: Journal of Health Science, Vol. 57, No. 2, p 115-128 (2011)
Non-Patent Document 4: Nature Methods, Vol. 9, No. 10, p 1021-1029 (2012)

SUMMARY OF INVENTION

Technical Problem

The object of the present invention is to provide a compound or a salt thereof, which has a lysophosphatidylserine receptor function modulation activity. A further object of the present invention is to provide a pharmaceutical composition or a lysophosphatidylserine receptor function modulator containing said compound or a salt thereof.

Solution to Problem

The present inventors conducted extensive studies to achieve the above object and found a compound having an agonist activity against GPR34, P2Y10 and/or GPR174, and completed the present invention relating to a compound or a salt thereof, which has a lysophosphatidylserine receptor agonist activity.

In other words, the present invention relates to a compound, pharmaceutical composition and a lysophosphatidylserine receptor function modulator shown below.
(1) A compound represented by formula (I):

[Formula 1]

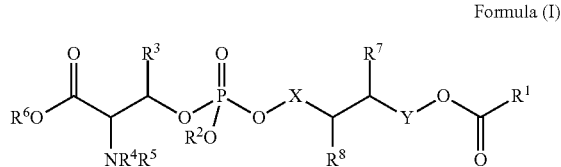

Formula (I)

wherein $R^1$ is $C_{1-30}$ alkyl, $C_{2-30}$ alkenyl, $C_{2-30}$ alkynyl, or a group represented by formula: —($C_{1-15}$ alkylene)-$Q^1$-$Z^1$—($C_{1-15}$ alkylene)-$Z^2$-$Q^2$;

in which $Q^1$ is $C_{3-10}$ cycloalkylene, 5-10 membered heterocyclylene, $C_{6-10}$ arylene, or 5-10 membered heteroarylene, $Q^2$ is a hydrogen atom, $C_{3-10}$ cycloalkyl, 5-10 membered heterocyclyl, $C_{6-10}$ aryl, or 5-10 membered heteroaryl, and $Q^2$ may be substituted with —$Z^3$-$Q^3$, $Q^3$ is $C_{3-10}$ cycloalkyl, 5-10 membered heterocyclyl, $C_{6-10}$ aryl, or 5-10 membered heteroaryl, $Z^1$, $Z^2$, and $Z^3$ are independently selected from the group consisting of an oxygen atom, a sulfur atom, —$NR^9$—, difluoromethylene, and a direct bond, wherein the alkyl, alkenyl, alkynyl, cycloalkylene, heterocyclylene, arylene, heteroarylene, cycloalkyl, heterocyclyl, aryl, and heteroaryl may be independently substituted with one or more substituents selected from halo and hydroxy;

$R^2$ is a hydrogen atom, $C_{1-6}$ alkyl, $C_{7-14}$ aralkyl, or $C_{1-6}$ alkoxy $C_{1-6}$ alkyl;

$R^3$ is a hydrogen atom or $C_{1-6}$ alkyl;

$R^4$ and $R^5$ are independently selected from the group consisting of a hydrogen atom, $C_{1-6}$ alkyl, $C_{7-14}$ aralkyl, formyl, $C_{1-6}$ alkylcarbonyl, arylcarbonyl, $C_{1-6}$ alkoxycarbonyl, $C_{1-6}$ alkoxy $C_{1-6}$ alkyl, and $C_{7-14}$ aralkyloxycarbonyl;

$R^6$ is a hydrogen atom, $C_{1-6}$ alkyl, $C_{1-6}$ alkoxy $C_{1-6}$ alkyl, or $C_{7-14}$ aralkyl;

$R^7$ is a hydrogen atom or $C_{1-6}$ alkyl, $R^8$ is $C_{1-6}$ alkyl, in which the alkyl may be substituted with one or more substituents selected from the group consisting of hydroxy, $C_{1-6}$ alkoxy, $C_{3-10}$ cycloalkyloxy, a 5-10 membered heterocyclyloxy, $C_{7-14}$ aralkyloxy, $C_{6-10}$ aryloxy, and a 5-10 membered heteroaryloxy, or $R^7$ and $R^8$ together with a carbon atom that they are attached may form a ring selected from a $C_{3-10}$ saturated carbocyclic ring, and a 5-10 membered saturated or partially-saturated heterocyclic ring;

$R^9$ is a hydrogen atom or $C_{1-6}$ alkyl;

X is $CH_2$ or a direct bond, with the proviso that when X is $CH_2$, $R^7$ and $R^8$ together with a carbon atom that they are attached form a ring; and Y is $CH_2$ or a direct bond, or a salt thereof.

(2) A compound according to (1), which is represented by formula (Ia):

[Formula 2]

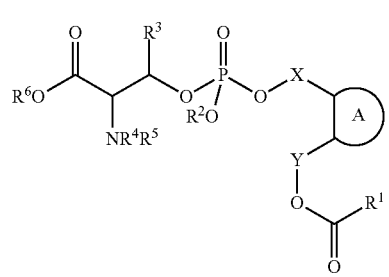

Formula (Ia)

wherein $R^8$ is $C_{1-6}$ alkyl, wherein the alkyl may be substituted with hydroxy, $C_{1-6}$ alkoxy, $C_{3-10}$ cycloalkyloxy, 5-10 membered heterocyclyloxy, $C_{7-14}$ aralkyloxy, $C_{6-10}$ aryloxy, or 5-10 membered heteroaryloxy; and $R^1$, $R^2$, $R^3$, $R^4$, $R^5$, and $R^6$ are as defined in (1), or a salt thereof.

(3) A compound according to (1), which is represented by formula (Ib):

[Formula 3]

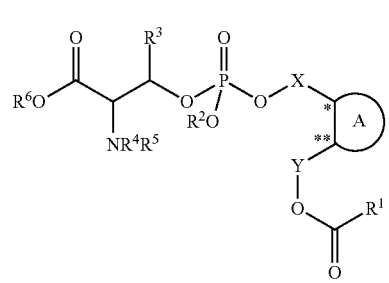

Formula (Ib)

wherein A is a ring selected from $C_{3-10}$ saturated carbocyclic ring, and a 5-10 membered saturated or partially-saturated heterocyclic ring; and $R^1$, $R^2$, $R^3$, $R^4$, $R^5$, $R^6$, X, and Y are as defined in (1), or a salt thereof.

(4) A compound according to (3), which is represented by formula (Ic):

[Formula 4]

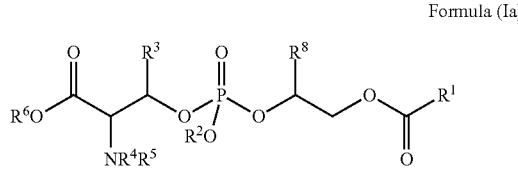

Formula (Ic)

wherein A is a ring selected from the following:

[Formula 5]

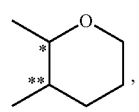

Formula (IIa)

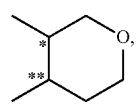

Formula (IIb)

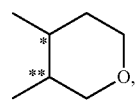

Formula (IIc)

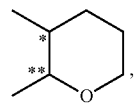

Formula (IId)

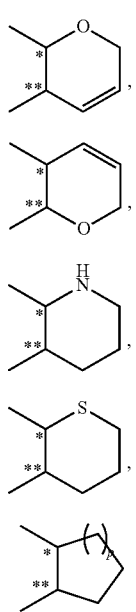

Formula (IIe)

Formula (IIf)

Formula (IIg)

Formula (IIh)

Formula (IIi)

wherein p is 1-5, and
* and ** represent the binding positions of side chains on ring A;
$R^1$, $R^2$, $R^3$, $R^4$, $R^5$, $R^6$, X, and Y are as defined in (1), or a salt thereof.
(5) A compound according to any of (1) to (4), wherein $R^3$ is a hydrogen atom or methyl.
(6) A compound according to any of (1) to (5), wherein $R^1$ is selected from the following:

[Formula 6]

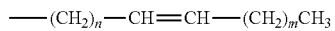

Formula (IIIa)

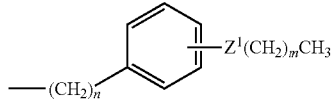

Formula (IIIb)

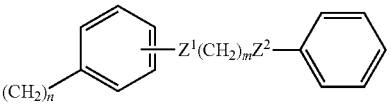

Formula (IIIc)

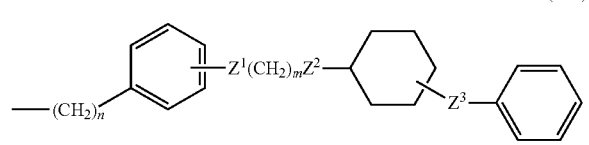

Formula (IIId)

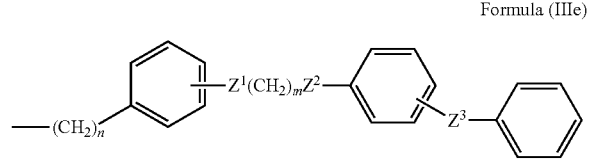

Formula (IIIe)

wherein n and m are independently 1 to 12, and $Z^1$, $Z^2$, and $Z^3$ are as defined in (1), or a salt thereof.
(7) A compound selected from:

(9Z)-octadeca-9-enoic acid (2R)-2-[((2S)-2-amino-2-carboxy-ethoxy)-hydroxy-phosphoryloxy]-propyl ester;
(9Z)-octadeca-9-enoic acid (2S)-2-[((2S)-2-amino-2-carboxy-ethoxy)-hydroxy-phosphoryloxy]-propyl ester;
(2S)-2-amino-3-[hydroxyl-((1R)-1-methyl-2-{3-[2-(3-phenoxy-benzyloxy)-phenyl]-propionyloxy}-ethoxy)-phosphoryloxy]-propionic acid;
(9Z)-octadeca-9-enoic acid (2R)-2-[((2S)-2-amino-2-carboxy-ethoxy)-hydroxy-phosphoryloxy]-3-methoxy-propyl ester;
(9Z)-octadeca-9-enoic acid (2S)-2-[((2S)-2-amino-2-carboxy-ethoxy)-hydroxy-phosphoryloxy]-3-methoxy-propyl ester;
(9Z)-octadeca-9-enoic acid (2R)-2-[((2S)-2-amino-2-carboxy-ethoxy)-hydroxy-phosphoryloxy]-3-ethoxypropyl ester;
(9Z)-octadeca-9-enoic acid (2R)-2-[((2S)-2-amino-2-carboxy-ethoxy)-hydroxy-phosphoryloxy]-3-benzyloxy-propyl ester;
(2S)-2-amino-3-(hydroxy{(3R,4R)-4-[3-(2-undecyloxy-phenyl)-propionyloxy]-tetrahydro-pyran-3-yloxy}-phosphoryloxy)-propionic acid;
(2S)-2-amino-3-(hydroxy{(3R,4R)-3-[3-(2-undecyloxy-phenyl)-propionyloxy]-tetrahydropyran-4-yloxy}-phosphoryloxy)-propionic acid;
(2S)-2-amino-3-(hydroxy {(3S,4S)-4-[3-(2-undecyloxy-phenyl)-propionyloxy]-tetrahydro-pyran-3-yloxy}-phosphoryloxy)-propionic acid;
(2S)-2-amino-3-(hydroxy{(3S,4S)-3-[3-(2-undecyloxy-phenyl)-propionyloxy]-tetrahydro-pyran-4-yloxy}-phosphoryloxy)-propionic acid;
(2S)-2-amino-3-({(3S,4S)-3-[3-(5-tert-butyl-2-undecyloxy-phenyl)-propionyloxy]-tetrahydro-pyran-4-yloxy}-hydroxy-phosphoryloxy)-propionic acid;
(2S)-2-amino-3-[hydroxy((2R,3S)-3-{3-[2-(3-phenoxy-benzyloxy)-phenyl]-propionyloxy}-tetrahydro-pyran-2-ylmethoxy)-phosphoryloxy]-propionic acid;
(2S)-2-amino-3-(hydroxy {(2R,3S)-3-[3-(2-undecyloxy-phenyl)-propionyloxy]-tetrahydro-pyran-2-ylmethoxy}-phosphoryloxy)-propionic acid;
(9Z)-octadeca-9-enoic acid (2R,3R)-3-[((2S)-2-amino-2-carboxy-ethoxy)-hydroxy-phosphoryloxy]-tetrahydro-pyran-2-ylmethyl ester;
(2S)-2-amino-3-(hydroxy{(2R,3R)-2-[3-(2-undecyloxy-phenyl)-propionylmethoxy]-tetrahydro-pyran-3-yloxy}-phosphoryloxy)-propionic acid;
(2S)-2-amino-3-[hydroxy-((2R,3R)-2-{3-[2-(3-phenoxy-benzyloxy)-phenyl]-propionylmethoxy}-tetrahydropyran-3-yloxy)-phosphoryloxy]-propionic acid;
(2S)-2-amino-3-[hydroxy-((2R,3R)-3-{3-[2-(3-phenoxy-benzyloxy)-phenyl]-propionyloxy}-tetrahydropyran-2-ylmethoxy)-phosphoryloxy]-propionic acid;
(2S)-2-amino-3-(hydroxyl-{(2R,3S)-2-[3-(2-undecyloxy-phenyl)-propionyloxymethyl]-3,6-dihydro-2H-pyran-3-yloxy}-phosphoryloxy)-propionic acid;
(9Z)-octadeca-9-enoic acid (2R,3S)-3-[((2S)-2-amino-2-carboxy-ethoxy)-hydroxy-phosphoryloxy]-tetrahydro-pyran-2-ylmethyl ester;
(2S)-2-amino-3-(hydroxy-{(2R,3S)-2-[3-(2-undecyloxy-phenyl)-propionyloxymethyl]-tetrahydro-pyran-3-yloxy}-phosphoryloxy)-propionic acid;
(2S)-2-amino-3-[hydroxy-((2R,3S)-2-{3-[2-(3-phenoxy-benzyloxy)-phenyl]-propionyloxymethyl}-tetrahydropyran-3-yloxy)-phosphoryloxy]-propionic acid;
(9Z)-octadeca-9-enoic acid (2R,3S)-3-[((2S)-2-amino-2-carboxy-ethoxy)-hydroxy-phosphoryloxy]-3,6-dihydro-2H-pyran-2-ylmethyl ester;

(2S)-2-amino-3-[hydroxy-((2R,3S)-2-{3-[2-(3-phenoxy-benzyloxy)-phenyl]-propionyloxymethyl}-3,6-dihydro-2H-pyran-3-yloxy)-phosphoryloxy]-propionic acid;
(2S)-2-amino-3-(hydroxy-{(2R,3R)-2-[3-(2-undecyloxy-phenyl)-propionyloxymethyl]-3,6-dihydro-2H-pyran-3-yloxy}-phosphoryloxy)-propionic acid;
(2S)-2-amino-3-[hydroxy-((2R,3R)-2-{3-[2-(3-phenoxy-benzyloxy)-phenyl]-propionyloxymethyl}-3,6-dihydro-2H-pyran-3-yloxy)-phosphoryloxy]-propionic acid;
(2S,3S)-2-amino-3-[hydroxy-((2R,3S)-3-{3-[2-(3-phenoxy-benzyloxy)-phenyl]-propionyloxy}-tetrahydropyran-2-ylmethoxy)-phosphoryloxy]-butyric acid;
(2S,3S)-2-amino-3-[hydroxy-((2R,3R)-3-{3-[2-(3-phenoxy-benzyloxy)-phenyl]-propionyloxy}-tetrahydro-pyran-2-ylmethoxy)-phosphoryloxy]-butyric acid;
(2S,3S)-2-amino-3-[hydroxy-((2R,3S)-2-{3-[2-(3-phenoxy-benzyloxy)-phenyl]-propionyloxymethyl}-tetrahydro-pyran-3-yloxy)-phosphoryloxy]-butyric acid;
(2S,3S)-2-amino-3-[hydroxy-((2R,3R)-2-{3-[2-(3-phenoxy-benzyloxy)-phenyl]-propionyloxymethyl}-tetra-hydro-pyran-3-yloxy)-phosphoryloxy]-butyric acid; and
(2S)-2-amino-3-[hydroxy-((1R)-1-methoxymethyl-2-{3-[2-(3-phenoxy-benzyloxy)-phenyl]-propionyloxy}-ethoxy)-phosphoryloxy]-propionic acid,
or a salt thereof.
(8) A pharmaceutical composition for use in treating an auto-immune disease, which comprises the compound according to any of (1) to (7) or a salt thereof.
(9) A lysophosphatidylserine receptor function modulator, which comprises the compound according to any of (1) to (7) or a salt thereof, and acts on one or more lysophosphatidylserine receptor selected from GPR34, P2Y10, and GPR174.
(10) The lysophosphatidylserine receptor function modulator according to (9), which acts on any two of lysophosphatidylserine receptors selected from GPR34, P2Y10, and GPR174.
(11) The lysophosphatidylserine receptor function modulator according to (9), which acts selectively on GPR34.
(12) The lysophosphatidylserine receptor function modulator according to any of (9) to (11), which has a lysophosphatidylserine receptor agonist activity.

Advantageous Effects of Invention

The present invention provides a compound or a salt thereof, which has a lysophosphatidylserine receptor function modulation activity, and the present invention also provides a pharmaceutical composition or a lysophosphatidylserine receptor function modulator containing said compound or a salt thereof.

BRIEF DESCRIPTION OF DRAWING

FIG. 1 is graphs showing the assay results (Test Example 1) of agonist activities against GPR34, P2Y10, GPR174 receptors of lysophosphatidylserine analogs.

DESCRIPTION OF EMBODIMENTS

The present invention is explained in more detail below.
Compounds or their Salts
The compound or the salt thereof of the present invention includes the compounds of formulae (I), (Ia), (Ib) and (Ic) or salts thereof, and more specifically compounds described in the Examples provided hereinafter.

One embodiment of the present invention provides a compound represented by formula (I) or a salt thereof:

[Formula 7]

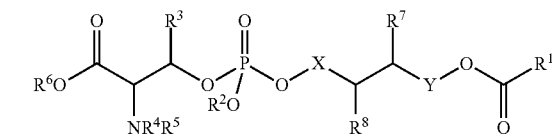

Formula (I)

wherein, $R^1$-$R^8$, X and Y are as defined above.
For example, $R^1$ is selected from the following formulae:

[Formula 8]

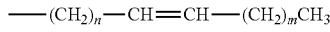

Formula (IIIa)

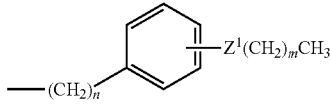

Formula (IIIb)

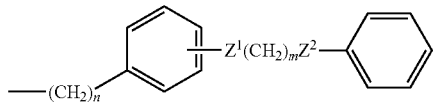

Formula (IIIc)

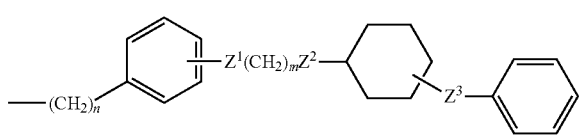

Formula (IIId)

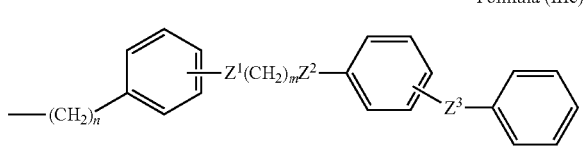

Formula (IIIe)

wherein n and m, $Z^1$, $Z^2$, and $Z^3$ are as defined above, and $R^1$ includes (8Z)-8-heptadecenyl, 2-(2-undecyloxyphenyl)ethyl, 2-[2-(3-phenoxybenzyloxyl)phenyl]ethyl, etc. Furthermore, in formula (IIIa) for example, n and m are each preferably 6 to 8, more preferably 7; in formula (IIIb), n is preferably 1 to 3, more preferably 2, and m is preferably 8 to 12, more preferably 10; in formula (IIIe), n is preferably 1 to 3, more preferably 2, and m is preferably 1 to 3, more preferably 2.
Furthermore, for example $R^8$ is methyl that may be substituted with one or more substituents selected from the group consisting of hydroxy, methoxy, ethoxy, benzyloxy.
Also, for example X and Y may correspond to cases (i) to (iii) below.
(i) When X is a direct bond and Y is a direct bond or $CH_2$, $R^7$ is a hydrogen atom or $C_{1-6}$ alkyl, for example, a hydrogen atom or methyl, preferably a hydrogen atom. $R^8$ is $C_{1-6}$ alkyl, in which the alkyl may be substituted with at least one substituent selected from the group consisting of hydroxy, $C_{1-6}$ alkoxy, $C_{3-10}$ cycloalkyloxy, a 5-10 membered heterocyclyloxy, $C_{7-14}$ aralkyloxy, $C_{6-10}$ aryloxy, and a 5-10 membered heteroaryloxy. Or else, when X is a direct bond and Y is a direct bond or CH$_2$, R$^7$ and R$^8$ together with the carbon atom which they are attached may form a ring selected from C$_{3-10}$ saturated carbon ring, and a 5-10 membered saturated or partially-saturated heterocycle;

(ii) When X and Y is CH$_2$, R$^7$ and R$^8$ together with the carbon atom which they are attached may form a ring;

(iii) When X is CH$_2$ and Y is a direct bond, R$^7$ and R$^8$ together with the carbon atom which they are attached may form a ring.

When R$^7$ and R$^8$ together with the carbon atom which they are attached form a ring, the resulting ring is, for example, a cyclohexane ring, a cyclopentane ring, a tetrahydrofuran ring, a tetrahydropyran ring, or a dihydropyran ring, and preferably a tetrahydropyran ring, or a dihydropyran ring.

A more preferable embodiment of the present invention provides a compound of the following formula (Ia) or a salt thereof.

[Formula 9]

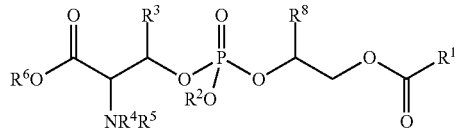

Formula (Ia)

wherein, R$^1$-R$^6$, R$^8$, X and Y are as defined above.

An even more preferable embodiment of the present invention provides a compound of the following formula (Ib) or a salt thereof.

[Formula 10]

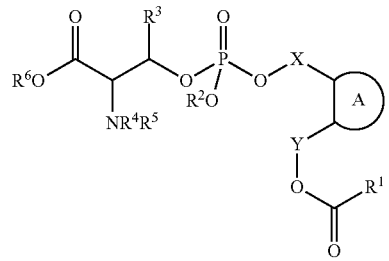

Formula (Ib)

wherein, R$^1$-R$^6$, X, Y and A are as defined above.

An even more preferable embodiment of the present invention provides a compound of the following formula (Ic) or a salt thereof.

[Formula 11]

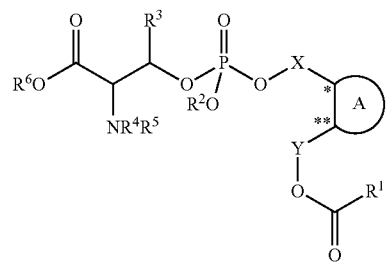

Formula (Ic)

wherein, R$^1$-R$^6$, X, Y and A are as defined above. Note that A is a ring structure that connects to X and Y at two ring-contained carbon atoms neighboring each other.

For example, A is a cyclohexane ring, a cyclopentane ring, a tetrahydrofuran ring, a tetrahydropyran ring, a dihydropyran ring, etc. and it is preferably a tetrahydropyran ring, a dihydropyran ring.

Most preferable embodiments of the present invention provide compounds shown in Table 1 below or salts thereof.

TABLE 1

| Compound No. | Structural Formula | Compound Name |
|---|---|---|
| 1 | | (9Z)-octadeca-9-enoic acid (2R)-2-[((2S)-2-amino-2-carboxy-ethoxy)-hydroxy-phosphoryloxy]-propyl ester |
| 2 | | (9Z)-octadeca-9-enoic acid (2S)-2-[((2S)-2-amino-2-carboxy-ethoxy)-hydroxy-phosphoryloxy]-propyl ester |
| 3 | | (2S)-2-amino-3-[hydroxyl-((1R)-1-methyl-2-{3-[2-(3-phenoxy-benzyloxy)-phenyl]-propionyloxy}-ethoxy)-phosphoryloxy]-propionic acid |

TABLE 1-continued

| Compound No. | Structural Formula | Compound Name |
|---|---|---|
| 4 |  | (9Z)-octadeca-9-enoic acid (2R)-2-[((2S)-2-amino-2-carboxy-ethoxy)-hydroxy-phosphoryloxy]-3-methoxy-propyl ester |
| 5 |  | (9Z)-octadeca-9-enoic acid (2S)-2-[((2S)-2-amino-2-carboxy-ethoxy)-hydroxy-phosphoryloxy]-3-methoxy-propyl ester |
| 6 |  | (9Z)-octadeca-9-enoic acid (2R)-2-[((2S)-2-amino-2-carboxy-ethoxy)-hydroxy-phosphoryloxy]-3-ethoxypropyl ester |
| 7 |  | (9Z)-octadeca-9-enoic acid (2R)-2-[((2S)-2-amino-2-carboxy-ethoxy)-hydroxy-phosphoryloxy]-3-benzyloxy-propyl ester |
| 8 |  | (2S)-2-amino-3-(hydroxy{(3R,4R)-4-[3-(2-undecyloxy-phenyl)-propionyloxy]-tetrahydro-pyran-3-yloxy}-phosphoryloxy)-propionic acid |
| 9 |  | (2S)-2-amino-3-(hydroxy{(3R,4R)-3-[3-(2-undecyloxy-phenyl)-propionyloxy]-tetrahydropyran-4-yloxy}-phosphoryloxy)-propionic acid |
| 10 |  | (2S)-2-amino-3-(hydroxy{(3S,4S)-4-[3-(2-undecyloxy-phenyl)-propionyloxy]-tetrahydro-pyran-3-yloxy}-phosphoryloxy)-propionic acid |
| 11 |  | (2S)-2-amino-3-(hydroxy{(3S,4S)-3-[3-(2-undecyloxy-phenyl)-propionyloxy]-tetrahydro-pyran-4-yloxy}-phosphoryloxy)-propionic acid |

TABLE 1-continued

| Compound No. | Structural Formula | Compound Name |
|---|---|---|
| 12 | | (2S)-2-amino-3-({(3S,4S)-3-[3-(5-tert-butyl-2-undecyloxy-phenyl)-propionyloxy]-tetrahydro-pyran-4-yloxy}-hydroxy-phosphoryloxy)-propionic acid |
| 13 | | (2S)-2-amino-3-[hydroxy((2R,3S)-3-{3-[2-(3-phenoxy-benzyloxy)-phenyl]-propionyloxy}-tetrahydro-pyran-2-ylmethoxy)-phosphoryloxy]-propionic acid |
| 14 | | (2S)-2-amino-3-(hydroxy{(2R,3S)-3-[3-(2-undecyloxy-phenyl)-propionyloxy]-tetrahydro-pyran-2-ylmethoxy}-phosphoryloxy)-propionic acid |
| 15 | | (9Z)-octadeca-9-enoic acid (2R,3R)-3-[((2S)-2-amino-2-carboxy-ethoxy)-hydroxy-phosphoryloxy]-tetrahydro-pyran-2-ylmethyl ester |
| 16 | | (2S)-2-amino-3-(hydroxy{(2R,3R)-2-[3-(2-undecyloxy-phenyl)-propionylmethoxy]-tetrahydro-pyran-3-yloxy}-phosphoryloxy)-propionic acid |

TABLE 1-continued

| Compound No. | Structural Formula | Compound Name |
|---|---|---|
| 17 | | (2S)-2-amino-3-[hydroxy-((2R,3R)-2-{3-[2-(3-phenoxy-benzyloxy)-phenyl]-propionylmethoxy}-tetrahydropyran-3-yloxy)-phosphoryloxy]-propionic acid |
| 18 | | (2S)-2-amino-3-[hydroxy-((2R,3R)-3-{3-[2-(3-phenoxy-benzyloxy)-phenyl]-propionyloxy}-tetrahydropyran-2-ylmethoxy)-phosphoryloxy]-propionic acid |
| 19 | | (2S)-2-amino-3-(hydroxyl-{(2R,3S)-2-[3-(2-undecyloxy-phenyl)-propionyloxymethyl]-3,6-dihydro-2H-pyran-3-yloxy}-phosphoryloxy)-propionic acid |
| 20 | | (9Z)-octadeca-9-enoic acid (2R,3S)-3-[((2S)-2-amino-2-carboxy-ethoxy)-hydroxy-phosphoryloxy]-tetrahydro-pyran-2-ylmethyl ester |
| 21 | | (2S)-2-amino-3-(hydroxy-{(2R,3S)-2-[3-(2-undecyloxy-phenyl)-propionyloxymethyl]-tetrahydro-pyran-3-yloxy}-phosphoryloxy)-propionic acid |

TABLE 1-continued

| Compound No. | Structural Formula | Compound Name |
|---|---|---|
| 22 | | (2S)-2-amino-3-[hydroxy-((2R,3S)-2-{3-[2-(3-phenoxy-benzyloxy)-phenyl]-propionyloxymethyl}-tetrahydropyran-3-yloxy)-phosphoryloxy]-propionic acid |
| 23 | | (9Z)-octadeca-9-enoic acid (2R,3S)-3-[((2S)-2-amino-2-carboxy-ethoxy)-hydroxy-phosphoryloxy]-3,6-dihydro-2H-pyran-2-ylmethyl ester |
| 24 | | (2S)-2-amino-3-[hydroxy-((2R,3S)-2-{3-[2-(3-phenoxy-benzyloxy)-phenyl]-propionyloxymethyl}-3,6-dihydro-2H-pyran-3-yloxy)-phosphoryloxy]-propionic acid |
| 25 | | (2S)-2-amino-3-(hydroxy-{(2R,3R)-2-[3-(2-undecyloxy-phenyl)-propionyloxymethyl]-3,6-dihydro-2H-pyran-3-yloxy}-phosphoryloxy)-propionic acid |
| 26 | | (2S)-2-amino-3-[hydroxy-((2R,3R)-2-{3-[2-(3-phenoxy-benzyloxy)-phenyl]-propionyloxymethyl}-3,6-dihydro-2H-pyran-3-yloxy)-phosphoryloxy]-propionic acid |

TABLE 1-continued

| Compound No. | Structural Formula | Compound Name |
|---|---|---|
| 27 | | (2S,3S)-2-amino-3-[hydroxy-((2R,3S)-3-{3-[2-(3-phenoxy-benzyloxy)-phenyl]-propionyloxy}-tetrahydropyran-2-ylmethoxy)-phosphoryloxy]-butyric acid |
| 28 | | (2S,3S)-2-amino-3-[hydroxy-((2R,3R)-3-{3-[2-(3-phenoxy-benzyloxy)-phenyl]-propionyloxy}-tetrahydro-pyran-2-ylmethoxy)-phosphoryloxy]-butyric acid |
| 29 | | (2S,3S)-2-amino-3-[hydroxy-((2R,3S)-2-{3-[2-(3-phenoxy-benzyloxy)-phenyl]-propionyloxymethyl}-tetrahydro-pyran-3-yloxy)-phosphoryloxy]-butyric acid |
| 30 | | (2S,3S)-2-amino-3-[hydroxy-((2R,3R)-2-{3-[2-(3-phenoxy-benzyloxy)-phenyl]-propionyloxymethyl}-tetrahydro-pyran-3-yloxy)-phosphoryloxy]-butyric acid |
| 31 | | (2S)-2-amino-3-[hydroxy-((1R)-1-methoxymethyl-2-{3-[2-(3-phenoxy-benzyloxy)-phenyl]-propionyloxy}-ethoxy)-phosphoryloxy]-propionic acid |

In the present specification, "$C_{1-6}$ alkyl" is a straight chain, branched chain, cyclic or partially cyclic alkyl group of 1 to 6 carbons. For example, it includes methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, cyclopropyl, cyclobutyl, cyclopentyl, cyclohexyl, and cyclopropylmethyl, and it also includes $C_{1-4}$ alkyl and $C_{1-3}$ alkyl.

In the present specification, "$C_{1-30}$ alkyl" is a straight chain, branched chain, cyclic or partially cyclic alkyl group of 1 to 30 carbons. For example, it includes a straight chain, branched chain, cyclic or partially cyclic alkyl group represented by $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, and $C_{30}H_{61}$, in addition to the $C_{1-6}$ alkyl groups given above as $C_{1-6}$ alkyl.

In the present specification, "$C_{1-15}$ alkylene" is a bivalent group of $C_{1-15}$ alkane connecting at two points. The group includes, for example, a group represented by formula —$(CH_2)_q$— (wherein, q is 1 to 15).

In the present specification, "$C_{1-6}$ alkylcarbonyl" is an alkylcarbonyl group having the above defined $C_{1-6}$ alkyl group as the alkyl section. It includes, for example, methylcarbonyl(acetyl), ethylcarbonyl, tert-butylcarbonyl and also $C_{1-4}$ alkylcarbonyl.

In the present specification, "$C_{1-6}$ alkoxy" is an alkyloxy group having the above defined alkyl group with 1 to 6 carbons as the alkyl section. It includes, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cyclopentyloxy, cyclohexyloxy, cyclopropylmethyloxy, and it also includes $C_{1-4}$ alkoxy and $C_{1-3}$ alkoxy. Also, "$C_{1-4}$ alkoxy" in the present specification includes $C_{1-3}$ alkoxy.

In the present specification, "$C_{1-6}$ alkoxycarbonyl" is an alkoxycarbonyl group having the above defined $C_{1-6}$ alkoxy group as the alkoxy section. It includes, for example, methoxycarbonyl, ethoxycarbonyl, tert-butoxycarbonyl and also $C_{1-3}$ alkoxycarbonyl.

In the present specification, "$C_{1-6}$ alkoxy $C_{1-6}$ alkyl" includes, for example, methoxymethyl, ethoxymethyl, 2-methoxyethyl, 1-methoxyethyl.

In the present specification, "$C_{2-30}$ alkenyl" includes a straight chain or a branched chain alkenyl group of 2 to 30 carbons containing one double bond (e.g. 8-heptadecenyl). The term further includes a straight chain or a branched chain alkenyl group containing 2 double bonds (e.g. 9,12-octadecadienyl), a straight chain or a branched chain alkenyl group containing 3 double bonds (e.g. 9,12,15-octadecatrienyl), a straight chain or a branched chain alkenyl group containing 4 double bonds (e.g. 5,8,11,14-eicosatetraenyl), and a straight chain or a branched chain alkenyl group containing 5 or more double bonds.

In the present specification, "$C_{2-30}$ alkynyl" is a straight chain or a branched chain alkenyl group of 2 to 30 carbons, including a straight chain or a branched chain alkynyl group having 1 triple bond, and also a straight chain or a branched chain alkynyl group having 2 or more triple bonds.

In the present specification, "$C_{3-10}$ cycloalkyl" is a cyclic alkyl group having 3 to 10 carbons, and it includes, for example, cyclopropyl, cyclobutyl, cyclopentyl, cyclohexyl. Note that $C_{3-10}$ cycloalkyl falls within the range indicated by the above $C_{1-30}$ alkyl.

In the present specification, "$C_{3-10}$ saturated carbon ring" is a saturated carbon ring having 3 to 10 carbons, and it includes, for example, cyclopropane, cyclobutane, cyclopentane, cyclohexane.

In the present specification, "$C_{3-10}$ cycloalkyloxy" includes, for example, cyclopropyloxy, cyclobutyloxy, cyclopentyloxy, cyclohexyloxy.

In the present specification, "$C_{3-10}$ cycloalkylene" is a bivalent group in which a saturated carbon ring having 3-10 carbons connects at 2 points.

In the present specification, "5-10 membered heterocyclyl" is a saturated or partially saturated aliphatic heterocyclic group containing at least 1 hetero atom selected from the oxygen atom, nitrogen atom and sulfur atom, wherein the ring includes 5 to 10 atoms. Specific examples include oxetanyl, tetrahydrofuranyl, tetrahydropyranyl, pyrrolidinyl, piperidinyl, piperazinyl, morpholinyl, tetrahydrothiopyranyl.

In the present specification, "5-10 membered saturated or partially-saturated heterocycle" is a saturated or partially saturated aliphatic heterocycle containing at least one hetero atom selected from the oxygen atom, nitrogen atom and sulfur atom, wherein the ring includes 5 to 10 atoms. It includes, for example, oxetane, tetrahydrofuran, tetrahydropyran pyrrolidine, piperidine, piperazine, morpholine, tetrahydrothiopyran.

In the present specification, "5-10 membered heterocyclyloxy" includes for example oxetanyloxy, tetrahydrofuranyloxy, tetrahydropyranyloxy, pyrrolidinyloxy, piperidinyloxy, piperazinyloxy, morpholinyloxy, tetrahydrothiopyranyloxy.

In the present specification, "5-10 membered heterocyclylene" is a bivalent group in which a 5-10 membered heterocycle connects at 2 points.

In the present specification, "$C_{6-10}$ aryl" is, for example, an aromatic carbon cyclic group having 6-10 carbons, and it includes phenyl, naphthyl.

In the present specification, "$C_{6-10}$ aryloxy" includes phenoxy, naphthyloxy.

In the present specification, "$C_{6-10}$ arylcarbonyl" includes benzoyl.

In the present specification, "$C_{6-10}$ arylene" is a bivalent group in which $C_{6-10}$ aromatic carbon ring connects at 2 points. The phenylene group includes, for example, a 1,2-substituted group, a 1,3-substituted group, and a 1,4-substituted group.

In the present specification, "$C_{7-14}$ aralkyl" is an arylalkyl group including an aryl group and having 7-14 carbons. It includes for example benzyl, 1-phenethyl, 2-phenethyl, 1-naphthylmethyl, 2-naphthylmethyl. The number of carbons in the alkyl group section is 1 to 4, for example.

In the present specification, "$C_{7-14}$ aralkyloxy" includes, for example, benzyloxy, 1-phenethyloxy, 2-phenethyloxy, 1-naphthylmethyloxy, 2-naphthylmethyloxy.

In the present specification, "$C_{7-14}$ aralkyloxycarbonyl" includes, for example, benzyloxycarbonyl, 1-phenethyloxycarbonyl, 2-phenethyloxycarbonyl, 1-naphthylmethyloxycarbonyl, 2-naphthylmethyloxycarbonyl.

In the present specification, "5-10 membered heteroaryl" is an aromatic heterocyclic group that is monocyclic with 5-10 atoms in the ring including 1 or more hetero atom selected from the oxygen atom, nitrogen atom or sulfur atom. Specific examples include pyrrolyl, imidazolyl, pyrazolyl, triazolyl, pyridyl, pyrimidyl, pyridazinyl, furyl, thienyl, oxazolyl, oxadiazolyl, thiazolyl, thiadiazolyl.

In the present specification, "5-10 membered heteroaryloxy" includes, for example, pyrrolyloxy, imidazolyloxy, pyrazolyloxy, triazolyloxy, pyridyloxy, pyrimidyloxy, pyridazinyloxy, furyloxy, thienyloxy, oxazolyloxy, oxadiazolyloxy, thiazolyloxy, thiadiazolyloxy.

In the present specification, "5-10 membered heteroarylene" is a bivalent group in which 5-10 membered aromatic heterocycle connects at 2 points. It includes, for example, a group in which connections are made at neighboring ring atoms, a group in which the second connection exists at a ring atom that is the second atom from the ring atom forming the first connection, and a group in which the second connection exists at a ring atom that is the third atom from the ring atom forming the first connection. Specific examples of a heterocycle constituting the group include pyrrole, imidazole, pyrazole, triazole, pyridine, pyrimidine, pyridazinine, furan, thiophene, oxazole, oxadiazole, thiazole, thiadiazole.

In the present specification, a compound having one or more double bonds between carbon atoms can be a cis-isomer or a trans-isomer.

The present invention relating to compounds represented by formulae (I), (Ia), (Ib) and (Ic) includes various stereoisomers such as tautomers, geometric isomers, optical isomers, etc., and mixtures thereof.

The "salt" of the compound of the present invention is not particularly limited as long as it is a salt, and a pharmaceutically applicable salt is preferable. Salts that can be formed from compounds of the present invention and a base include the following: salts with inorganic base, such as sodium, potassium, magnesium, calcium and aluminum; salts with organic base, such as methylamine, ethylamine, ethanolamine. The salts may be acid addition salts, which specifically include acid addition salts incorporating the following acids: mineral acids, such as hydrochloric acid, hydrobromic acid, hydriodic acid, sulfuric acid, nitric acid, phosphoric acid; and organic acids, such as formic acid, acetic acid, trifluoroacetic acid, propionic acid, oxalic acid, malonic acid, succinic acid, fumaric acid, maleic acid, lactic acid, malic acid, tartaric acid, citric acid, methansulfonic acid, ethansulfonic acid.

In addition, the compounds of the present invention provide hydrates, various solvates, polymorphs, etc.

The atoms (e.g. hydrogen atom, carbon atom, oxygen atom, nitrogen atom, sulfur atom and phosphorous atom) included in the compounds of the present invention may be isotopic atoms that fall outside isotopes predominant in nature, and the isotopic atom may be a radioisotope atom. In other words, one aspect of the present invention provides compounds of formula (I), (Ia), (Ib), or (Ic) defined in the present specification labeled with an isotopic atom, or a salt thereof. The labeling of an isotopic atom may be performed by applying a radioisotope ($^{3}H$, $^{14}C$, $^{32}P$) and label by $^{3}H$ is preferable in view of easy preparation of the compound. The $^{3}H$ labeled compound of the present invention can be synthesized by, for example, using a $^{3}H$ labeled fatty acid or a derivative thereof.

In one embodiment of the present invention, compounds of formulae (I), (Ia), (Ib) and (Ic) are administered as prodrug, and then they are converted into an active compound in vivo. For example, $R^2$ and $R^6$ in formulae (I), (Ia), (Ib) and (Ic) may be groups that form carbonic acid esters or phosphoric acid esters. Specific examples include groups described in the Journal of Medicinal Chemistry, 2008, 51(8), 2337, which include $C_{1-6}$ alkyl (e.g. tert-butyl), $C_{1-6}$ alkoxy$C_{1-6}$ alkyl (e.g. methoxymethyl), $C_{1-6}$ alkylcarbonyloxy$C_{1-6}$ alkyl (e.g. pivaloyloxymethyl), $C_{1-6}$ alkoxycarbonyloxy$C_{1-6}$ alkyl (e.g. isopropoxycarbonyloxymethyl), substitutable phenyl (e.g. $C_{1-3}$ alkoxyphenyl), substitutable benzyl (e.g. benzyl that can be substituted with 1-3 groups selected from $C_{1-6}$ alkoxy, hydroxy, $C_{1-6}$ alkylcarbonyloxy, nitro, and a halogen atom), phthalidyl (e.g. isobenzofuranon-3-yl that can be substituted with 1-4 groups selected from $C_{1-6}$ alkoxy), dioxolenonylmethyl (e.g. dioxolenon-4-yl methyl that can be substituted with a group selected from $C_{1-6}$ alkoxy or phenyl at position 5 of the dioxolenon ring), or furylmethyl (e.g. 2-furylmethyl that can be substituted with nitro at position 5 of the furan ring).

Synthesis of Compounds or their Salts

The lysophosphatidylserine receptor is a module type molecule consisting of a hydrophilic section (the amino acid section and the phosphodiester section), the hydrophobic section (the acyl side chain section), and the connection section that connects the hydrophilic section and the hydrophobic section, so the modular structures can be systematically converted according to the following general synthesis method to synthesize the compounds of the present invention and salts thereof. The compounds of formulae (I), (Ia), (Ib) and (Ic) may be synthesized by the steps of the following scheme, for example.

Scheme 1: General Synthesis Method of Chain Type Compound (Formula Ia)

[Formula 12]

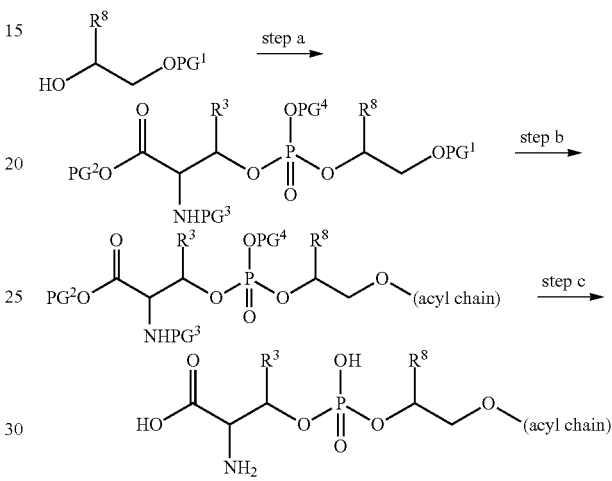

In the formula, $R^3$ and $R^8$ are as previously defined in the present specification; —O-(acyl chain) corresponds to —O—CO—$R^1$ in formulae (I) and (Ia) as previously defined in the present specification; $PG^1$, $PG^2$, $PG^3$ and $PG^4$ each refer to a protection group, for example, $PG^1$, $PG^2$, and $PG^4$ are TBS or tert-butyl, and $PG^3$ is Boc.

Compounds included in formula (Ia) can be prepared by performing condensation oxidation of secondary alcohol and phosphoramidite at the connection section in step a, then deprotection of alcohol and a subsequent condensation with the acyl side chain section in step b, and deprotection of phosphodiester, carboxylate ester and amine in step c.

The condensation reaction of step a is performed by using an active derivative of phosphoric acid and a suitable condensation agent. The reaction may also be performed in a suitable solvent, such as methylene chloride, tetrahydrofuran, N,N'-dimethylformamide, toluene, diethyl ether, 1,4-dioxane, and under the presence of a suitable reaction accelerator (e.g. 1H-tetrazol). The oxidation step may be performed in a suitable solvent using a suitable oxidant (e.g. tert-butylhydroperoxide, meta-chloroperoxybenzoic acid, iodine-pyridine-water, etc.). The condensation step and the oxidation step may be performed on the product obtained by an after treatment following the condensation reaction, or the reaction may be a one-pot reaction without an after treatment.

The acylation step of alcohol in step b may be performed using acid chloride, and the step may be performed in a suitable solvent, under the presence of a suitable base (e.g. 4-dimethylaminopyridine) or the absence of base. Acylation may also be performed by using carboxylic acid and a suitable condensing agent (e.g. 1-ethyl-3-(3-dimethyl aminopropyl)carbodiimide hydrochloric acid salt (EDC), 1,3-diisopropyl carbodiimide (DIC)). The deprotection step prior to the condensation step can be performed by applying an appropriate deprotection condition, and one example is to use TFA.

In the deprotection step of step c, the desired compound that is included in formula (Ia) can be obtained by applying an appropriate deprotection condition like step b, and/or further converting the substituent.

These steps are not particularly limited, but they can be performed at a reaction temperature of 0 to 70° C., preferably 15 to 30° C., and at a reaction time of 10 min. to 2 days, preferably 1 to 2 hours.

Scheme 2: General Synthesis Method 1 of Cyclic Compound (Formula Ib, Ic)

[Formula 13]

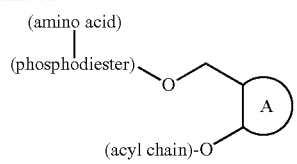

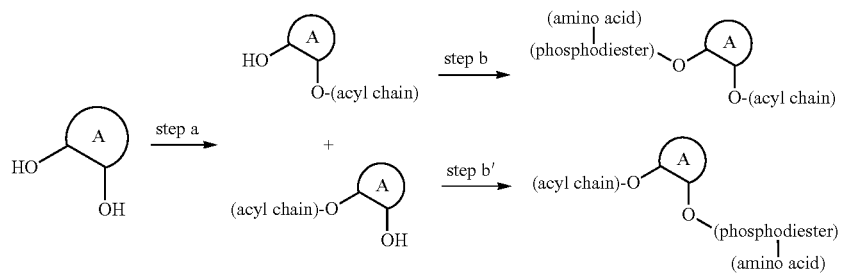

In the formula, A is as previously defined in the present specification; —O-(acyl chain) corresponds to —O—CO—$R^1$ in formulae (I), (Ib) and (Ic) as previously defined in the present specification; —O-(phosphodiester)-(amino acid) corresponds to $R^6O$—CO—CH($NR^4R^5$)—CH($R^3$)—O—PO($OR^2$)—O— in formulae (I), (Ib) and (Ic) as previously defined in the present specification.

The compounds included in formulae (Ib) and (Ic) may be prepared by condensing one secondary alcohol in the connection section (ring A) and an acyl side chain section in step a, then further condensing the remaining secondary alcohols in the connection section (ring A) and phosphoramidite followed by oxidation, and further deprotecting phosphodiester, carboxylate ester and amine in steps b and b'. The reactions of step a, steps b and b' can be performed under the same condition as the condensation/oxidation/deprotection reaction of Scheme 1.

Scheme 3: General Synthesis Method 2 of Cyclic Compound (Formula Ib, Ic)

[Formula 14]

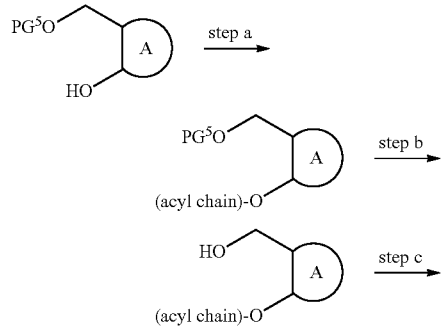

In the formula, A is as previously defined in the present specification; —O-(acyl chain) corresponds to —O—CO—$R^1$ in formulae (I), (Ib) and (Ic) as previously defined in the present specification; —O-(phosphodiester)-(amino acid) corresponds to $R^6O$—CO—CH($NR^4R^5$)—CH($R^3$)—O—PO($OR^2$)—O— in formulae (I), (Ib) and (Ic) as previously defined in the present specification; $PG^5$ refers to a protection group, which can be exemplified by TBS or tert-butyl.

Compounds included in formulae (Ib) and (Ic) may be prepared by condensing the hydroxy group of ring A and the acyl side chain section in step a, deprotecting alcohol in step b, and further condensing the alcohol in the hydroxymethyl group of ring A and phosphoramidite followed by oxidation, then deprotecting phosphodiester, carboxylate ester and amine. Reactions of steps a to c may be performed under the same condition as the condensation/oxidation/deprotection reactions of Scheme 1.

Scheme 4: General Synthesis Method 3 of Cyclic Compound (Formula Ib, Ic)

[Formula 15]

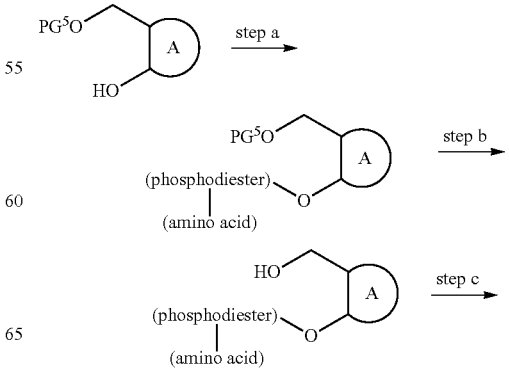

-continued

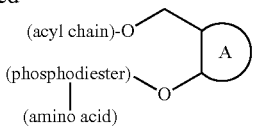

In the formula, A is as previously defined in the present specification; —O-(acyl chain) corresponds to —O—CO—R¹ in formulae (I), (Ib) and (Ic) as previously defined in the present specification; —O-(phosphodiester)-(amino acid) corresponds to R⁶O—CO—CH(NR⁴R⁵)—CH(R³)—O—PO(OR²)—O— in formulae (I), (Ib) and (Ic) as previously defined in the present specification; PG⁵ refers to a protection group, which can be exemplified by TBS or tert-butyl.

Compounds included in formulae (Ib) and (Ic) may be prepared by condensing the hydroxy group of ring A and the phosphoramidite in step a, deprotecting alcohol in step b, and condensing the alcohol in the hydroxymethyl group of ring A and acyl side chain section followed by oxidation, then deprotecting phosphodiester, carboxylate ester and amine. Reactions of steps a to c may be performed under the same condition as the condensation/oxidation/deprotection reaction of Scheme 1.

Scheme 5: General Synthesis Method of Amino Acid Section

[Formula 16]

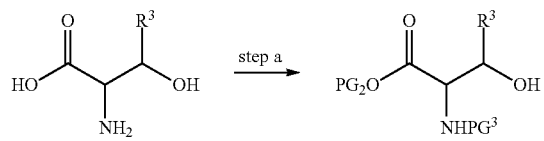

In the formula, R³, PG² and PG³ are as previously defined in the present specification.

The amino acid section used in the synthesis of formulae (I), (Ia), (Ib) and (Ic) may be prepared by protecting the carboxylate and amine of the alcohol section of the amino acid with suitable substituents PG² and PG³.

The protection reaction of carboxylate and amine in step a can be performed by applying a suitable protection condition.

Scheme 6: General Synthesis Method of Phosphoramidite

[Formula 17]

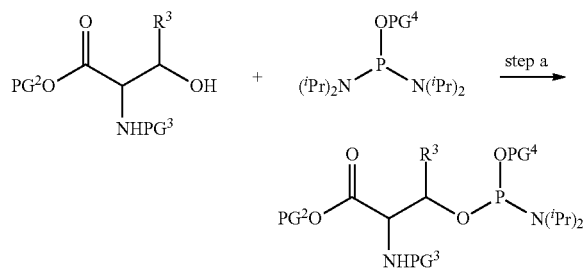

In the formula R³, PG², PG³, and PG⁴ are as previously defined in the present specification.

Phosphoramidite used in the synthesis of formulae (I), (Ia), (Ib) and (Ic) may be prepared by reacting alcohol (amino acid section) synthesized in Scheme 5 and bis(diisopropylamino)-tert-butyl phosphine. The condensation step of step a may be performed under the same condition as the condensation step of step a in Scheme 1.

Scheme 7: General Sythesis Method of Side Chain Section of Benzene Ring

[Formula 18]

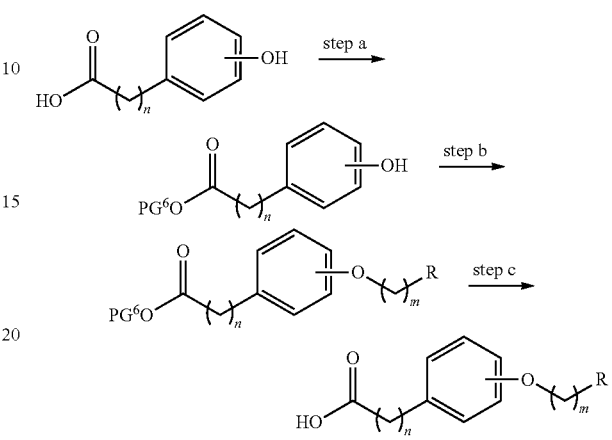

In the formula, n and m are as previously defined in the present specification; PG⁶ refers to a protection group, which can be exemplified by TBS or tert-butyl.

The side chain section having a benzene ring used in the synthesis of formulae (I), (Ia), (Ib) and (Ic) may be prepared by protecting the carboxylate in phenol having a carboxylate group in step a, alkylating phenol in step b, and deprotecting carboxylate in step c.

The protection step of phosphoric acid in step a may be performed by applying a suitable protection condition. The alkylation reaction of phenol in step b may be performed under a suitable condition by using halogenated alkyl as a reaction agent. The deprotection step of step c may be performed by applying a suitable deprotection condition.

Pharmaceutical Composition

The pharmaceutical composition of the present invention may be in various dosage foil is. Compositions for oral administration may be in the form of tablets, capsules, powders, granules, pills, liquids, emulsions, suspensions, solutions, spirits, syrups, extracts, elixirs. Compositions for parental administration may be in the form of injections, such as hypodermic injection, intravenous injection, intramuscular injection, intraperitoneal injection; dermal administration or patches, ointments or lotions; hypoglossal agents, oral patches for intraoral administration; and aerosol agents for nasal administration. However, the dosage form is not limited to the above forms. These pharmaceutical formulations may be produced by known methods normally used in the pharmaceutical formulation process. Compounds of formulae (I), (Ia), (Ib) and (Ic) are preferably administered as parental agents.

The pharmaceutical compositions may include various components that are used commonly, and it may include one or more pharmaceutically acceptable excipients, disintegrators, diluents, lubricants, flavors, colorants, sweeteners, correctives, suspending agents, humectants, emulsifiers, dispersants, adjuvants, preservatives, buffers, binders, stabilizers, coating agents. In addition, the pharmaceutical composition of the present invention may be in prolonged or sustained release dosage forms.

The dosage of therapeutic agent, prophylactic or pharmaceutical composition of the present invention may be appropriately selected according to the administration route, the body shape, age, physical condition of the patient, severity of the disease, elapsed time since onset, etc. and the pharmaceutical composition of the present invention may include the compounds of formulae (I), (Ia), (Ib) or (Ic) at a therapeutic dose and/or preventative dose. The compounds of formulae (I), (Ia), (Ib) and (Ic) may be used generally in a dose for adult of 1 to 10000 mg/day. Administration of the pharmaceutical composition may be a one-time administration or multi-time administrations, and it can be used in combination with other drugs, such as immunosuppressive agents (cyclosporine, tacrolimus, sirolimus, methotrexate, azathioprine, etc.), steroidal anti-inflammatory drugs (hydrocortisone, prednisolone, dexamethasone, etc.), non-steroidal anti-inflammatory drugs (loxoprofen sodium, indometacin, diclofenac sodium, etc.) or antibody drugs (infliximab, adalimumab, tocilizumab, certolizumab pegol, etanercept, etc.).

The therapeutic agent or prophylactic of the present invention may include components such as conventionally known colorants, preservatives, flavors, savors, coatings, anti-oxidants, vitamin, amino acids, peptides, proteins and minerals (iron, zinc, magnesium, iodide, etc.). The therapeutic agent or prophylactic of the present invention may be prepared in forms that are suitable for pharmaceutical composition, functional food, health food, beverages and supplements, for example in the form of different solid pharmaceutical formulations, such as granules (including dry syrup), capsules (soft capsules, hard capsules), tablets (including chewable agents), powders (powders), pills or liquids for internal use (including liquids, suspensions, and syrups). Further, the therapeutic agent or prophylactic of the present invention may be used on its own as a pharmaceutical composition, functional food, health food, beverages and supplements.

Additives for pharmaceutical formulation include, for example, excipients, lubricants, binders, disintegrators, fluidization agents, dispersants, humectants, preservatives, viscous agents, pH adjustors, colorants, correctives, surfactants, solubilizers. In addition, thickeners such as pectin, xanthan gum, and guar gum may be added when forming a liquid agent. In addition, the coating agent can be used to form a coating tablet or a paste-like deflocculant. For other forms of pharmaceutical formulation, the conventional method can be applied.

A pharmaceutical composition which is one aspect of the present invention has a lysophosphatidylserine receptor function modulation activity, lysophosphatidylserine receptor agonist activity, suppressive effect against mast cell degranulation, suppressive effect against histamine liberation, suppressive effect against leukotriene generation, suppressive effect against prostaglandin generation, suppressive effect against IL-13 generation, suppressive effect against tryptase secretion, and suppressive effect against antigen-antibody reaction that acts on at least one of the lysophosphatidylserine receptors selected from GPR34, P2Y10, and GPR174 based on the chemical structure of compounds shown by formulae (I), (Ia), (Ib) and (Ic). In addition, the pharmaceutical composition of the present invention may be used as a therapeutic agent or a prophylactics for diseases such as an autoimmune disease. The autoimmune disease may be either a systemic autoimmune disease or an organ specific disease, and examples include malignant rheumatoid arthritis, systemic lupus erythematosus, multiple sclerosis, myasthenia gravis, Graves' disease, anti-phospholipid antibody syndrome, Sjögren's syndrome, primary biliary cirrhosis, polymyositis, and autoimmune hepatitis.

Lysophosphatidylserine Receptor Function Modulator

One aspect of the present invention provides a function modulator of one or more lysophosphatidylserine receptors selected from GPR34, P2Y10 and GPR174 containing the above compounds or salts thereof. Further, the lysophosphatidylserine receptor function modulator may optionally adjust two functions selected from GPR34, P2Y10 and GPR174, or it may selectively adjust the GPR34 function.

The "lysophosphatidylserine receptor function modulator" of the present invention is an agent that is used for its action on the lysophosphatidylserine receptor of GPR34, P2Y10 and GPR174, to enhance or suppress the expression of the subject receptor, or to enhance or suppress the in vivo function specific to the subject receptor.

The lysophosphatidylserine receptor is a module type molecule consisting of a hydrophilic section (the amino acid section and the phosphodiester section), the hydrophobic section (the acyl side chain section), and the connection section that connects the hydrophilic section and the hydrophobic section, so the modular structures can be systematically converted according to the following general synthesis method and the necessity of each module structure in the bioactivity expression can be assessed to find the necessary structure for the expression of bioactivity of lysophosphatidylserine or the structural requirement for developing a receptor selective agonist. In other words, the lysophosphatidylserine receptor function modulator of the present invention may be used as a chemical tool to find an unknown biological function of the lysophosphatidylserine receptor by incorporating a compound having an agonist activity against one or more receptors, or a compound having selective agonist activity to 2 receptors (dual agonist activity) or a selective agonist activity to 1 receptor. In addition, the lysophosphatidylserine receptor function modulator of the present invention may be used as an active component of the above mentioned pharmaceutical composition.

<GPR34 Function Modulator>

GPR34 is expressed at a high level in mononuclear leukocytes, centered on macrophage, so it is assumed to be involved in suppressing migration, growth and activation of macrophage and granulocyte. Further, in the lung infection experiment of pathogenic bacteria (*Cryptococcus neoformans*), the GPR34 knockout mouse has more pathogenic bacteria than a wild-type mouse, and they are found to have abnormality in the removal function of pathogenic bacteria. In other words, GPR34 is suggested to be involved in a wide range of immune response through mononuclear leukocytes, and a lysophosphatidylserine receptor function modulator to selectively modulate the GPR34 function can be used to discover the physiological function that the mononuclear leukocytes are involved in.

Furthermore, it has been confirmed that generation of cytokines, such as tumor necrosis factor-$\alpha$ (TNF-$\alpha$) or interferon-$\gamma$ (IFN-$\gamma$) is excessively enhanced in GPR34 knockout mice, and a report suggests suppression of cytokine generation as GPR34 function. In other words, the lysophosphatidylserine receptor function modulator that selectively modulates the GPR34 function may be used as the chemical tool to elucidate the suppression of cytokine generation in vivo.

Further, it is useful as a drug, such as prophylactics/therapeutic agent for diseases relating to GPR34 function.

<P2Y10 Function Modulator>

P2Y10 is expressed on a large part in lymphoid organs, such as the thymus gland or the spleen, and a large increase of expression is seen particularly in activated lymphocytes. Further, P2Y10 is reported to inhibit the generation of cell agglutination mass of activated T lymphocytes by suppressing the LFA1 function, and it has the possibility of being involved in suppressing cell adhesion by inhibiting LFA-1-ICAM-1 interaction of activated lymphocytes as the physiological function of P2Y10. In other words, the $P2Y_{10}$ function modulator may be used as a chemical tool for elucidating the physiological function relating to inhibition of cell adhesion of activated lymphocytes.

Further, it is useful as a drug, such as prophylactics/therapeutic agent for diseases relating to P2Y10 function.

<GPR174 Function Modulator>

Similarly to P2Y10, GPR174 is also expressed largely on the lymphoid organ, such as the thymus gland or the spleen. Since a large increase of expression is seen particularly in activated lymphocytes, GPR174 may also hold some important function in the activation stage of the immune system. For example, it has been found that a GPR174 selective agonist suppresses IL-2 generation unlike the P2Y10 selective agonist which does not suppress IL-2 generation in the activation lymphocytes. In other words, the GPR174 function modulator that selectively modulates the GPR174 function may be used as a chemical tool for elucidating the physiological function relating to suppressing the IL-2 generation of activated lymphocytes.

It is also useful as a drug, such as prophylactics/therapeutic agent, for diseases relating to GPR174 function.

Assay Method of Compounds and their Salts

The agonist activity of the subject compound against the lysophosphatidylserine receptor may be assessed using GPR34, P2Y10 and GPR174. That is, the assay or screening method of the above compounds or their salts as the subject compound is not limited as long as it uses GPR34, P2Y10 and GPR174, but it can be performed by using cells that express genes encoding GPR34, P2Y10 and GPR174, a transgenic non-human mammal that excessively expresses genes encoding GPR34, P2Y10 and GPR174, transgenic non-human mammal that expresses genes encoding human GPR34, human P2Y10 and human GPR174. Cells for use in the assay or screening are not particularly limited, but include known cultured cells that are normally used, for example, HEK293 cells. Also, the non-human mammal includes a mouse, a rat, a rabbit, a dog, a cat or a monkey. The tissue or cell of the animal can also be used for screening. In such a case, the administration of the subject compound is performed, for example, by incorporating the subject compound in the solution or culture in which the tissue or cell is retained, and letting the subject compound act on the target.

The assay or screening of the compounds or their salts may be performed by using cultured cells that express genes encoding GPR34, P2Y10 and GPR174, and it is preferable to use cultured cells in view of screening efficiency. Also, since GPR34, P2Y10 and GPR174 are G protein-coupled receptors, assay can be performed by referring to calcium response, cAMP generation, and reporter genes as indices. Further, an assay can be performed by letting the cultured cells express genes that encode labeled human epidermal growth factor receptor (EGFR) ligands, and quantifying labeled compounds that were cut off. Specific examples of labeled EGFR ligands include fusion protein of EGFR ligands and alkaline phosphatase. Further, the labeled EGFR ligands include Transforming growth factor α (TGFα). An assay method using a labeled EGFR ligand may be performed by referring to Tokumaru et al., J Cell Biol 151, 209-220 (2000); Inoue et al., Nature Methods 9, 1021-1019 (2012).

GPR34, P2Y10 and GPR174 used in the above assay or screening are not particularly limited as long as they are polypeptides having their receptor activities, and GPR34, P2Y10 and GPR174 derived from mammals such as human, mouse or rat are used. Specific examples include polypeptides having a GPR34, P2Y10 and GPR174 activity disclosed in Patent Documents 2 and 5.

EXAMPLES

The present invention is explained in detail below by Examples without being limited thereby.

Reagent and Data Measurement

Reagents purchased from Sigma-Aldrich Chemical Co., Tokyo Chemical Industry Co., Wako Pure Chemical Industries, Ltd., Kanto Chemical Co., Ltd. were used without further purification. $^{1}$H- and $^{13}$C-NMR were measured using BRUKER AVANCE 400 spectrometer (400 MHz), and the chemical shift was shown by ppm against deuterated chloroform (7.26 ppm ($^{1}$H-NMR), 77.00 ppm ($^{13}$C-NMR)). The $^{31}$P-NMR chemical shift was shown by ppm against phosphoric acid in water (85% w/w, 0.00 ppm). The mass analysis was performed using the positive and negative ion mode of BRUKER microTOF-05 spectrometer (ESI-TOF) or SHIMADZU AXIMA-TOF (MALDI-TOF). The silica gel to be used in the column chromatography was purchased from Kanto Chemical Co., Ltd. The element analysis was performed using Yanaco MT-6 CHN CORDER spectrometer.

Example 1

Synthesis of (9Z)-Octadeca-9-enoic acid (2R)-2-[((2S)-2-amino-2-carboxy-ethoxy)-hydroxy-phosphoryloxy]-propyl ester

[Formula 19]

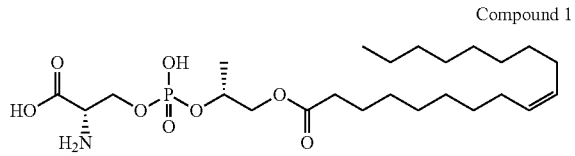

Compound 1

Synthesis of Intermediate 1-1

[Formula 20]

Intermediate 1-1

(R)-1,2-Propanediol (201.1 mg, 2.643 mmol) and imidazole (269.9 mg, 3.964 mmol) were dissolved in anhydrous DMF (4 mL). The resulting solution was added to a solution of TBSCl (436.0 mg, 2.893 mmol) in DMF (2 mL) at room temperature and the mixture was stirred at room temperature for 11 hours. The obtained solution was diluted with water (10 mL) and ethyl acetate (10 mL), the aqueous layer was separated and extraction was performed three times with ethyl acetate (10 mL×3). The organic layer was collected and dried with sodium sulfate, then the solvent was distilled.

The residue was purified by column chromatography (hexane: ethyl acetate=5:1) to give the title compound (478.0 mg, 2.511 mmol, 95%, colorless oil-like matter).

$^{1}$H-NMR(CDCl$_{3}$): δ=3.812 (1H, m), 3.587 (2H, d, J=9.92, 3.36 Hz), 3.587 (2H, d, J=9.92, 3.72 Hz), 2.323 (1H, brs), 1.111 (3H, d, J=8.32 Hz), 0.903 (9H, s), 0.070 (6H, s). $^{13}$C-NMR (CDCl$_{3}$): δ=68.53, 67.93, 25.87, 18.28, 18.18, −5.37, −5.41. HRMS (ESI, [M+Na]$^{+}$): Calcd for C$_{33}$H$_{70}$NaO$_{3}$Si$_{2}$$^{+}$: 593.4756. Found: 593.4758.

Synthesis of Intermediate 1-2

[Formula 21]

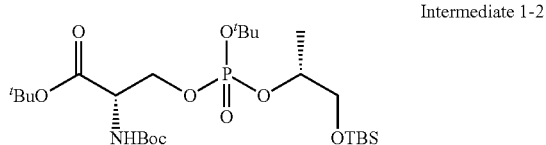

Intermediate 1-2

To remove the contained water, phosphoramidite 6 (202.1 mg, 0.435 mmol) synthesized by Scheme 9 shown below was dissolved in dichloromethane (5 mL) and toluene (0.5 mL), then the solvent was distilled under vacuum. To the obtained residue, Intermediate 1-1 (100.1 mg, 0.526 mmol) was added, then dichloromethane (5 mL) and toluene (0.5 mL) were added, and the solvent was distilled under vacuum. The residue was dissolved in dichloromethane (2 mL) under an argon atmosphere, then a THF (2 mL) solution of 1H-tetrazole (92.3 mg, 1.317 mmol) was added at room temperature. White powders precipitated after a few minutes. The reaction mixture was stirred for 5 hours at room temperature, and tert-butylhydroperoxide (decane solution of TBHP (5.0-6.0 M, 0.175 mL, 0.875 mmol)) was added at room temperature, then the mixture was further stirred at room temperature for 2 hours. The obtained solution was diluted with water (10 mL), and extraction was performed three times with dichloromethane (10 mL×3). The organic layer was collected and washed with salt solution, dried with sodium sulfate and the solvent was distilled. The residue was purified by column chromatography (hexane:ethyl acetate=7:2) to give the title compound (226.3 mg, 0.397 mmol, 91%, colorless oil-like matter).

$^{1}$H-NMR (CDCl$_{3}$): δ=5.490 (1H, m), 4.407 (1H, m), 4.335 (2H, m), 4.202 (1H, m), 3.687 (1H, m), 3.538 (1H, m), 1.482 (9H, m), 1.466 (9H, s), 1.436 (9H, s), 1.300 (3H, dd, J=10.60, 6.32 Hz), 0.883 (9/2H, s), 0.880 (9/2H, s), 0.057 (3/2H, s), 0.052 (3/2H, s), 0.048 (3/2H, s), 0.045 (3/2H, s). $^{31}$P-NMR(CDCl$_{3}$): δ=−6.034, −6.354. $^{13}$C-NMR(CDCl$_{3}$): δ=168.41, 155.25, 83.44, 83.37, 83.31, 82.54, 82.51, 79.80, 75.48, 75.44, 75.42, 75.38, 67.30, 67.25, 66.47, 66.44, 66.40, 66.37, 54.48, 54.40, 29.83, 29.81, 29.79, 29.77, 28.31, 27.95, 27.94, 25.83, 18.27, 18.13, 18.09, 18.05, −5.38, −5.41, −5.42, −5.46. HRMS (ESI, [M+Na]$^{+}$): Calcd for C$_{25}$H$_{52}$NNaO$_{9}$PSi$^{+}$: 592.3041. Found: 592.3051.

Synthesis of Intermediate 1-3

[Formula 22]

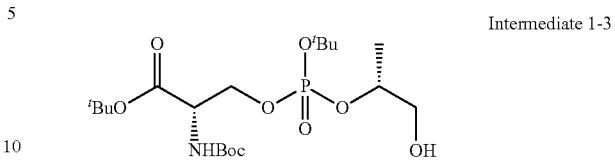

Intermediate 1-3

Drops of HF.pyridine (150 μL) were added to a THF (3 mL) and pyridine (150 μL) mixed solution of Intermediate 1-2, and the solution was stirred for 20 hours. The obtained solution was diluted with a 5% KHSO$_{4}$ solution (10 mL) and ethyl acetate (10 mL), then the aqueous layer was separated and extraction was performed three times with ethyl acetate (10 mL×3). The organic layer was collected and dried with sodium sulfate, then the solvent was distilled. The residue was purified by column chromatography (hexane: ethyl acetate=1:1-0:1) to give the title compound (129.0 mg, 0.283 mmol, 73%, white solid).

$^{1}$H-NMR (CDCl$_{3}$): δ=5.516 (1H, m), 4.533 (1H, m), 4.386-4.218 (3H, m), 3.633 (2H, m), 2.637 (1H, brs), 1.512-1.481 (18H, m), 1.450 (9H, s), 1.286 (3H, t, J=6.04 Hz). $^{31}$P-NMR(CDCl$_{3}$): δ=−4.990, −5.084. $^{13}$C-NMR (CDCl$_{3}$): δ=168.51, 168.39, 155.25, 82.87, 80.03, 67.61, 67.06, 66.91, 54.50, 54.42, 29.82, 29.80, 29.78, 29.76, 28.32, 27.96, 17.89, 17.83, 17.76. HRMS (ESI, [M+Na]$^{+}$): Calcd for C$_{19}$H$_{38}$NNaO$_{9}$P$^{+}$: 478.2176. Found: 478.2187.

Synthesis of Intermediate 1-4

[Formula 23]

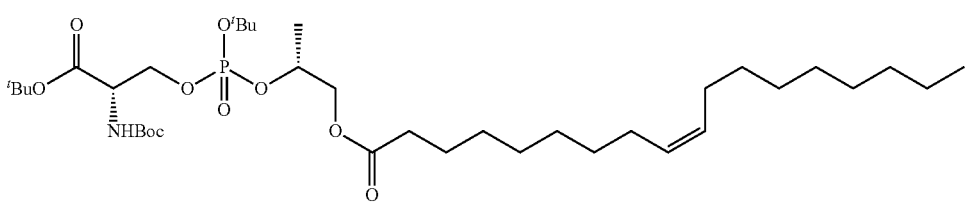

Intermediate 1-4

A solution of oleoyl chloride (30.5 mg, 0.101 mmol) in dichloromethane (1 mL) was added to a solution of Intermediate 1-3 (34.8 mg, 0.0764 mmol) and 4-dimethylaminopyridine (DMAP) (19.1 mg, 0.159 mmol) in dichloromethane (0.5 mL), and the solution was stirred at room temperature for 18 hours. Methanol (1 mL) and 1-ethyl-3-(3-dimethylaminopropyl)carbodiimide (EDCI) (34.0 mg, 0.178 mmol) were added to the reaction mixture, and the mixture was stirred at room temperature for 3 hours. The solvent of the reaction mixture was distilled, and the residue was purified by column chromatography (hexane:ethyl acetate=4:1) to give the title compound (43.6 mg, 0.0606 mmol, 79%, colorless oil-like matter).

$^{1}$H-NMR(CDCl$_{3}$): δ=5.503 (1H, m), 5.340 (2H, m), 4.634 (1H, m), 4.352 (2H, m), 4.228 (1H, m), 4.109 (2H, m), 2.334 (2H, m), 2.006 (4H, m), 1.613 (2H, m), 1.496-1.476 (18H, m), 1.444 (9H, s), 1.351-1.253 (23H, m), 0.878 (3H, t, J=6.82 Hz). $^{31}$P-NMR(CDCl$_{3}$): δ=−6.086, −6.476. $^{13}$C-NMR(CDCl$_{3}$): δ=173.41, 173.38, 168.37, 155.24, 129.99, 129.73, 83.76, 82.64, 82.61, 79.89, 77.32, 77.00, 76.68, 72.76, 72.70, 72.66, 72.60, 67.42, 66.70, 66.64, 54.47, 54.39, 34.09, 34.03, 31.89, 29.83, 29.79, 29.76, 29.71, 29.51, 29.31, 29.30, 29.20, 29.18, 29.12, 28.32, 27.97, 27.95, 27.21, 27.17, 24.83, 22.67, 18.16, 18.12, 18.09, 14.10. HRMS (ESI, [M+Na]$^+$): Calcd for $C_{37}H_{70}NNaO_{10}P^+$: 742.4630. Found: 742.4614.

Synthesis of Compound 1

[Formula 24]

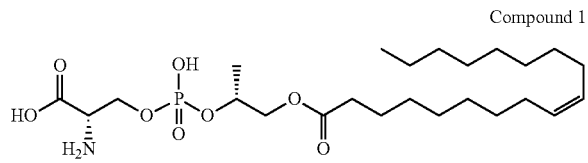

Compound 1

Intermediate 1-4 (42.1 mg, 0.0585 mmol) that has a protection group was dissolved in trifluoroacetic acid (TFA) (1.0 mL), and the mixture was stirred at room temperature for one hour, then the solvent was distilled. The residue was purified by column chromatography (chloroform:methanol: acetic acid=8:1:1) to give the acetic acid salt of the title compound (26.9 mg, 0.0530 mmol, 91%, white powder). The obtained acetic acid salt was dissolved in TFA, and the solvent was distilled to obtain the title compound as TFA salt (white powder).

$^1$H-NMR(CDCl$_3$/TFA-d=4:1): δ=5.365 (2H, m), 4.665 (3H, m), 4.552 (1H, m), 4.284 (1H, m), 4.176 (1H, m), 2.419 (2H, m), 2.018 (4H, m), 1.620 (2H, m), 1.379-1.271 (23H, m), 0.875 (3H, t, J=6.66 Hz). $^{31}$P-NMR(CDCl$_3$/TFA-d=4:1): δ=−2.252. HRMS (ESI, [M-H]$^-$): Calcd for $C_{24}H_{45}NO_8P^-$: 506.2888. Found: 506.2904. Mp: 151.0-152.0° C. Anal. Calcd. For $C_{26}H_{42}F_2NO_9P.0.5CF_3COOH$: C, 53.18; H, 8.30; N, 2.48. Found: C, 53.31; H, 8.30; N, 2.53.

Example 2

Synthesis of (9Z)-Octadeca-9-enoic acid (2S)-2-[((2S)-2-amino-2-carboxy-ethoxy)-hydroxy-phosphoryloxy]-propyl ester

[Formula 25]

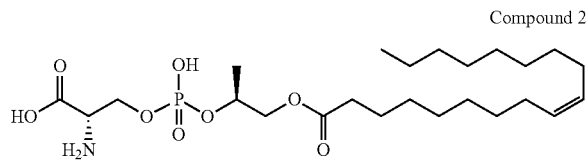

Compound 2

Synthesis was performed by the same method as Example 1 other than using (S)-1,2-propanediol instead of (R)-1,2-propanediol, and column chromatography (chloroform: methanol:acetic acid=8:1:1-6:1:3) was performed in the final step to refine the product and to thus obtain acetic acid salt (76.1 mg, 0.150 mmol, 73%, white powder) of the title compound. In addition, from that obtained acetic acid salt, TFA salt (white powder) of the title compound was obtained.

$^1$H-NMR(CDCl$_3$): δ=5.354 (2H, m), 4.550 (4H, m), 4.273 (1H, m), 4.143 (1H, m), 2.403 (2H, t, J=7 Hz), 1.998 (4H, m), 1.686 (2H, m), 1.343-1.270 (23H, m), 0.875 (3H, t, J=6.6 Hz). $^{31}$P-NMR(CDCl$_3$): δ=−2.55. HRMS (ESI-TOF, [M-H]$^-$): Calcd for $C_{25}H_{45}NO_8P^-$: 506.2888. Found: 506.2931. Mp: 133.5° C.-134.5° C., colorless solid. Anal. Calcd. for $C_{24}H_{46}NO_8P.0.6CF_3COOH$: C, 52.55; H, 8.15; N, 2.43. Found: C, 52.44; H, 7.92; N, 2.17.

Example 3

Synthesis of (2S)-2-amino-3-[hydroxyl-((1R)-1-methyl-2-{3-[2-(3-phenoxy-benzyloxy)-phenyl]-propionyloxy}-ethoxy)-phosphoryloxy]-propionic acid

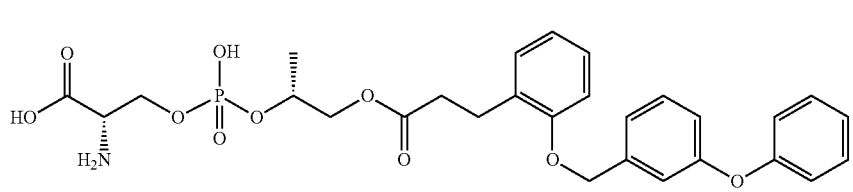 [SMILES: C[C@H](COC(=O)CCc1ccccc1OCc1cccc(Oc2ccccc2)c1)OP(=O)(O)OC[C@H](N)C(=O)O]

Compound 3

Synthesis was performed by the same method as Example 1 other than using Compound 100 synthesized by a method shown below instead of oleoyl chloride, and column chromatography (chloroform:methanol:acetic acid=8:1:1) was performed in the final step to refine the product and to thus obtain acetic acid salt (94.9 mg, 0.165 mmol, 81%, white powder) of the title compound. In addition, from that obtained acetic acid salt, TFA salt (white powder) of the title compound was obtained.

$^1$H-NMR (CDCl$_3$/TFA-d=4:1): δ=7.360-7.321 (3H, m), 7.215-7.082 (5H, m), 7.014-6.899 (5H, m), 5.085 (2H, s), 4.604 (3H, m), 4.476 (1H, m), 4.172 (1H, m), 4.118 (1H, m), 2.972 (2H, t, J=6.80 Hz), 2.738 (2H, t, J=6.90 Hz), 1.297 (3H, m). $^{31}$P-NMR(CDCl$_3$/TFA-d=4:1): δ=−2.301. HRMS (ESI, [M-H]$^-$): Calcd for $C_{28}H_{31}NO_{10}P^-$: 572.1691. Found: 572.1709. Mp: 143.5-144.5° C. Anal. Calcd. For $C_{28}H_{32}NO_{10}P.0.1CF_3COOH$: C, 57.90; H, 5.53; N, 2.39. Found: C, 57.66; H, 5.63; N, 2.46.

Example 4

Synthesis of (9Z)-Octadeca-9-enoic acid (2R)-2-[((2S)-2-amino-2-carboxy-ethoxy)-hydroxy-phosphoryloxy]-3-methoxy-propyl ester

[Formula 27]

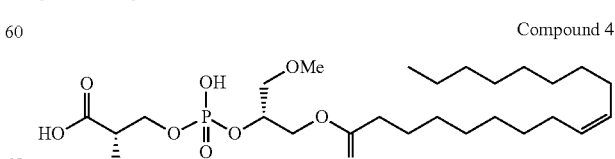

Compound 4

Synthesis was performed by the same method as Example 1 other than using (2S)-3-methoxy-1,2-propanediol instead of (R)-1,2-propanediol, and column chromatography (chloroform:methanol:acetic acid=8:1:1-7:1:2-6:1:3) was performed in the final step to refine the product and to thus obtain acetic acid salt (61.2 mg, 0.114 mmol, 83%, white powder) of the title compound. In addition, from that obtained acetic acid salt, TFA salt (white powder) of the title compound was obtained.

$^1$H-NMR(CDCl$_3$): δ=5.359 (2H, m), 4.698 (2H, m), 4.544 (1H, m), 4.446 (1H, m), 4.358 (1H, m), 4.281 (1H, m), 3.762 (2H, s), 3.520 (3H, s), 2.419 (2H, d, J=7.6 Hz), 2.016 (4H, m), 1.595 (2H, m), 1.284 (20H, m), 0.872 (3H, t, J=6.8 Hz). $^{31}$P-NMR(CDCl$_3$): δ=−1.96. HRMS (ESI-TOF, [M-H]$^-$): Calcd for C$_{25}$H$_{47}$NO$_9$P$^-$: 536.2994. Found: 536.3009. Mp. 192.5° C.-196.0° C., colorless solid. Anal. Calcd. For C$_{25}$H$_{48}$NO$_9$P.7.5CF$_3$COOH: C, 34.49; H, 4.02; N, 1.01. Found: C, 34.39; H, 4.35; N, 1.14.

Example 5

Synthesis of (9Z)-Octadeca-9-enoic acid (2S)-2-[((2S)-2-amino-2-carboxy-ethoxy)-hydroxy-phosphoryloxy]-3-methoxy-propyl ester

[Formula 28]

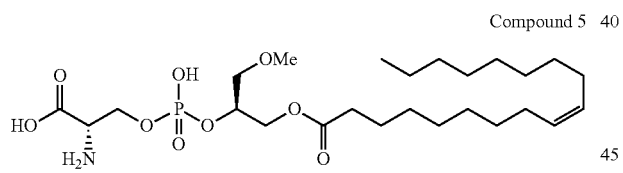

Compound 5

Synthesis was performed by the same method as Example 1 other than using (2R)-3-methoxy-1,2-propanediol instead of (R)-1,2-propanediol, and column chromatography (chloroform:methanol:acetic acid=8:1:1-7:1:2) was performed in the final step to purify the product and to thus obtain acetic acid salt (24.5 mg, 0.046 mmol, 90%, white powder) of the title compound. In addition, from that obtained acetic acid salt, TFA salt (white powder) of the title compound was obtained.

$^1$H-NMR(CDCl$_3$/TFA-d): δ=5.368 (1H, m), 4.698 (3H, m), 4.556 (1H, brs), 4.446 (1H, dd, J=3.2 Hz, 12 Hz), 4.266 (1H, d, J=10.4 Hz), 3.764 (2H, brs), 3.521 (3H, s), 2.416 (2H, t, J=6.8 Hz), 2.007 (2H, m), 1.662 (4H, m), 1.305-1.270 (20H, m), 0.875 (3H, t, J=6.6 Hz). $^{31}$P-NMR(CDCl$_3$/TFA-d): δ=−2.39. HRMS (ESI-TOF, [M-H]$^-$): Calcd for C$_{25}$H$_{47}$NO$_9$P$^-$: 536.2994. Found: 536.3003. Mp: 149.0° C.-150.5° C., colorless cube. Anal. Calcd. For C$_{25}$H$_{48}$NO$_9$P.1.1CF$_3$COOH: C, 49.27; H, 7.46; N, 2.11. Found: C, 49.18; H, 7.39; N, 2.28.

Example 6

Synthesis of (9Z)-Octadeca-9-enoic acid (2R)-2-[((2S)-2-amino-2-carboxy-ethoxy)-hydroxy-phosphoryloxy]-3-ethoxypropyl ester

[Formula 29]

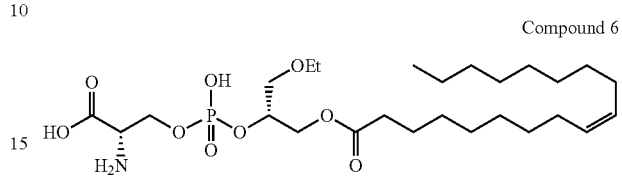

Compound 6

Synthesis was performed by the same method as Example 1 other than using (2S)-3-ethoxy-1,2-propanediol instead of (R)-1,2-propanediol, and column chromatography (chlorofolin:methanol:acetic acid=8:1:1-7:1:2) was performed in the final step to purify the product and to thus obtain acetic acid salt (34.0 mg, 0.062 mmol, 90%, white powder) of the title compound. In addition, from that obtained acetic acid salt, TFA salt (white powder) of the title compound was obtained.

$^1$H-NMR (CDCl$_3$/TFA-d): δ=5.372 (2H, m), 4.692 (3H, m), 4.567 (1H, brs), 4.436 (1H, dd, J=3.4 Hz, 11.8 Hz), 4.281 (1H, dd, J=3.6 Hz, 12.4 Hz), 3.769 (4H, m), 2.425 (2H, m), 2.007 (2H, m), 1.649 (4H, m), 1.306-1.246 (23H, m), 0.876 (3H, t, J=6.6 Hz).

NMR(CDCl$_3$/TFA-d): δ=−2.27. HRMS (ESI-TOF, [M-H]$^-$): Calcd for C$_{26}$H$_{50}$NO$_9$P$^-$: 550.3150. Found: 550.3174. Mp. 130.2° C.-131.0° C., colorless solid. Anal. Calcd. For C$_{26}$H$_{50}$NO$_9$P.0.7CF$_3$COOH: C, 52.12; H, 8.09; N, 2.22. Found: C, 51.96; H, 7.97; N, 2.17.

Example 7

Synthesis of (9Z)-Octadeca-9-enoic acid (2R)-2-[((2S)-2-amino-2-carboxy-ethoxy)-hydroxy-phosphoryloxy]-3-benzyloxy-propyl ester

[Formula 30]

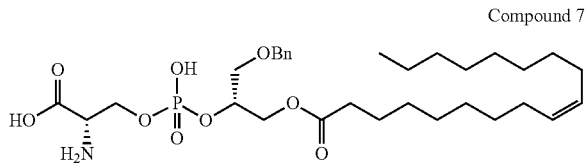

Compound 7

Synthesis was performed by the same method as Example 1 other than using (2S)-3-benzyloxy-1,2-propanediol instead of (R)-1,2-propanediol, and column chromatography (chloroform:methanol:acetic acid=8:1:1-7:1:2) was performed in the final step to purify the product and to thus obtain acetic acid salt (30.6 mg, 0.050 mmol, 98%, white powder) of the title compound. In addition, from that obtained acetic acid salt, TFA salt (white powder) of the title compound was obtained.

$^1$H-NMR(CDCl$_3$): δ=7.390-7.320 (5H, m), 5.380 (2H, m), 4.665 (5H, m), 4.409 (1H, brd, J=9.2 Hz), 4.265 (2H, m), 3.803 (2H, m), 2.368 (2H, t, J=7.6 Hz), 2.025 (2H, m), 1.674

(2H, m), 1.570 (2H, brt, J=6.2 Hz), 1.348-1.281 (20H, m), 0.879 (3H, t, J=6.6 Hz). $^{31}$P-NMR(CDCl$_3$): δ=−2.462. HRMS (ESI-TOF, [M-H]$^-$): Calcd for C$_{31}$H$_{51}$NO$_9$P$^-$: 612.3307. Found: 612.3278. Mp. 118.5-122.0° C., colorless cube. Anal. Calcd. For C$_{31}$H$_{52}$NO$_9$P.0.9CF$_3$COOH: C, 54.99; H, 7.44; N, 1.96. Found: C, 55.14; H, 7.51; N, 1.86.

Example 8

Synthesis of (2S)-2-amino-3-((3R,4R)-hydroxy-{4-[3-(2-undecyloxy-phenyl)-propionyloxy]-tetrahydro-pyran-3-yloxy}-phosphoryloxy)-propionic acid

[Formula 31]

Compound 8

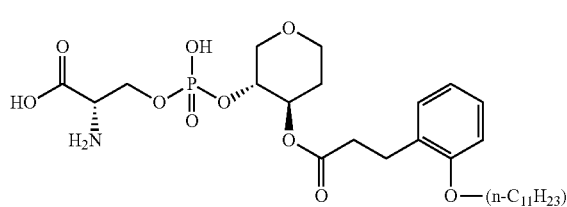

Synthesis of Intermediate 8-1-1, 8-1-2

[Formula 32]

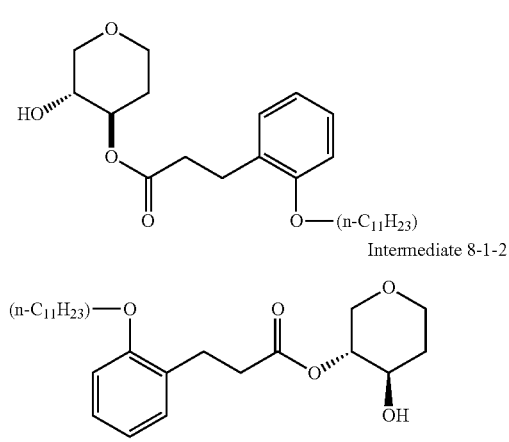

Intermediate 8-1-1

Intermediate 8-1-2

Compound 92 (242.8 mg, 0.758 mmol) synthesized by Scheme 10 shown below was added to a dichloromethane (11 mL) solution of (3R,4R)-tetrahydropyran-3,4-diol (120.4 mg, 1.019 mmol), EDCl/HCl (2.239 mg, 1.168 mmol) and DMAP (23.1 mg, 0.189 mmol) at 0° C., then the solution was stirred at room temperature for 6.5 hours. The obtained solution was diluted with water (20 mL) and the aqueous layer was separated and extraction was performed three times with dichloromethane (20 mL×3). The organic layer was collected and dried with sodium sulfate, then the solvent was distilled. The residue was purified by column chromatography (hexane:ethyl acetate=4:1) to give a mixture of the title compounds 8-1-1 and 8-1-2 (261.8 mg, 0.622 mmol, 82%, colorless oil-like matter).

HRMS (ESI-TOF, [M+Na]$^+$): Calcd. for C$_{25}$H$_{40}$NaO$_5$$^+$: 443.2768. Found: 443.2774.

Synthesis of Intermediate 8-2-1, 8-2-2

[Formula 33]

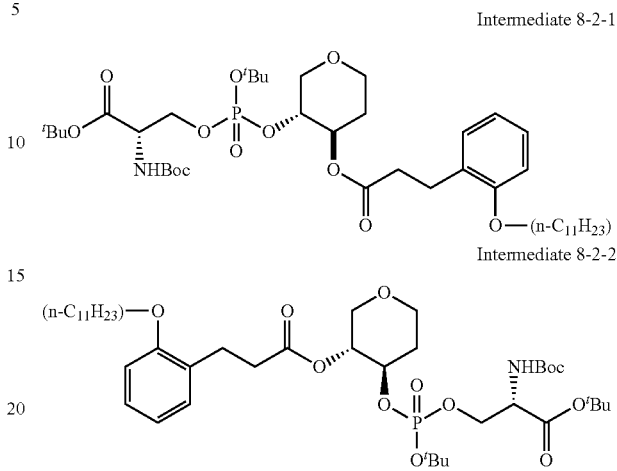

Intermediate 8-2-1

Intermediate 8-2-2

To remove the contained water, phosphoramidite 6 (433.4 mg, 0.933 mmol) synthesized by Scheme 9 shown below was dissolved in dichloromethane and toluene, then the solvent was distilled under vacuum. To the obtained residue, a mixture of Intermediates 8-1-1 and 8-1-2 (261.8 mg, 0.622 mmol) was added, then dichloromethane and toluene were added, and the solvent was distilled under vacuum. The residue was dissolved in dichloromethane (5 mL) under an argon atmosphere, then a THF (5 mL) solution of 1H-tetrazole (88.9 mg, 1.269 mmol) was added at room temperature. White powders precipitated after a few minutes. The reaction mixture was stirred for 5 hours at room temperature, and a saturated NaHCO$_3$ solution (15 ml) was added to complete the reaction, and extraction was performed three times with dichloromethane (20 ml×3). The organic layer was collected and dried with sodium sulfate, then the solvent was distilled. The residue was purified by column chromatography (hexane:ethyl acetate:triethylamine=35:4:1), and the solvent was distilled. The obtained residue was dissolved in dichloromethane (10 mL) under an argon atmosphere. Tert-butylhydroperoxide (decane solution of TBHP (5.0-6.0 M, 0.226 mL, 1.130 mmol)) was added at room temperature, then the mixture was further stirred at room temperature for 10.5 hours. The obtained solution was diluted with water (20 mL), and extraction was performed three times with dichloromethane (20 mL×3). The organic layer was collected and washed with salt solution, dried with sodium sulfate, and the solvent was distilled. The residue was purified by column chromatography (hexane:ethyl acetate=5:1-2:1) to give the title compounds 8-2-1 (27.6 mg, 0.035 mmol, 6%, colorless oil-like matter) and 8-2-2 (125.0 mg, 0.156 mmol, 25%, white oil-like matter).

8-2-1: $^1$H-NMR(CDCl$_3$): δ=7.145 (2H, m), 6.828 (2H, m), 5.670 (1H, dd, J=8.2 Hz, 16.2 Hz), 4.946 (1H, m), 4.348 (2H, m), 4.194 (2H, m), 3.926 (3H, m), 3.724 (1H, m), 3.517 (2H, m), 2.942 (2H, t, J=7.4 Hz), 2.648 (2H, m), 2.084 (1H, m), 1.794 (2H, m), 1.552 (1H, m), 1.494-1.423 (29H, m), 1.394-1.265 (14H, m), 0.877 (3H, t, J=6.8 Hz). $^{13}$C-NMR (CDCl$_3$): δ=172.36, 172.33, 172.28, 168.34, 168.30, 156.99, 156.95, 155.30, 129.94, 128.56, 128.53, 127.63, 127.59, 120.16, 111.04, 84.37, 84.30, 84.23, 84.16, 82.68, 82.57, 79.95, 79.90, 72.53, 72.48, 72.43, 72.41, 70.11, 70.03, 67.95, 67.84, 67.79, 67.49, 64.43, 64.22, 54.46, 54.38, 34.16, 34.11, 34.08, 31.89, 29.79, 29.76, 29.72, 29.60, 29.37, 29.32, 28.93, 28.31, 27.93, 26.14, 26.13, 22.66, 14.09. $^{31}$P-NMR(CDCl$_3$): δ=−6.34. HRMS (ESI-TOF, [M+Na]$^+$): Calcd. for C$_{36}$H$_{58}$NNaO$_9$PSi$^+$: 822.4528. Found: 822.4505.

8-2-2: $^1$H-NMR(CDCl$_3$): δ=7.143 (2H, m), 6.826 (2H, m), 5.576 (1H, m), 4.800 (1H, m), 4.452-4.302 (3H, m), 4.202 (1H, m), 3.948 (2H, t, J=6.4 Hz), 3.850 (2H, m), 3.526 (1H, m), 3.383 (1H, m), 2.940 (2H, m), 2.655 (2H, m), 2.129 (1H, m), 1.773 (3H, m), 1.538-1.439 (29H, m), 1.365-1.264 (14H, m), 0.875 (3H, t, J=6.6 Hz). $^{13}$C-NMR(CDCl$_3$): δ=172.31, 172.28, 168.30, 156.92, 155.25, 129.94, 128.57, 128.53, 127.59, 127.55, 120.13, 111.00, 84.28, 84.21, 84.04, 83.97, 82.68, 82.60, 79.94, 73.13, 73.07, 72.68, 72.66, 72.60, 69.36, 69.28, 69.15, 69.08, 67.77, 67.63, 67.57, 66.41, 66.17, 63.94, 63.58, 54.42, 54.34, 34.04, 33.98, 31.87, 30.31, 29.81, 29.76, 29.71, 29.59, 29.58, 29.57, 29.35, 29.30, 29.29, 28.30, 27.92, 26.09, 26.03, 22.64, 14.07. $^{31}$P-NMR(CDCl$_3$): δ=−6.33, −6.75. HRMS (ESI-TOF, [M+Na]$^+$): Calcd. for C$_{36}$H$_{58}$NNaO$_9$PSi$^+$: 822.4528. Found: 822.4506.

Synthesis of Compound 8

[Formula 34]

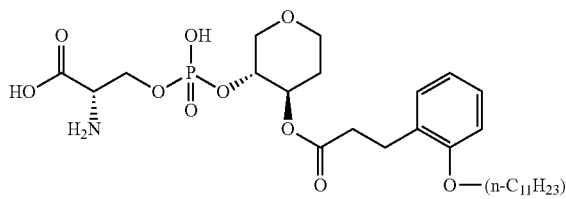

Compound 8

Intermediate 8-2 (27.4 mg, 0.034 mmol) that has a protection group was dissolved in 1,3-dimethoxybenzene (0.1 ml), then TFA (0.5 mL) was added. The mixture was stirred at 0° C. for one hour, and further at room temperature for 11 hours, then the solvent was distilled. The residue was purified by column chromatography (chloroform:methanol:acetic acid=9:1:1-8:1:1-7:1:2) to give the acetic acid salt of the title compound (19.8 mg, 0.034 mmol, 100%, white powder). The obtained acetic acid salt was dissolved in TFA, and the solvent was distilled to obtain the title compound as TFA salt (white powder).

$^1$H-NMR(CDCl$_3$): δ=7.212 (1H, t, J=7.6 Hz), 7.062 (1H, d, J=6.8 Hz), 6.895 (2H, m), 5.033 (1H, brs), 4.665 (2H, brs), 4.545 (1H, brs), 4.194 (1H, brs), 4.032 (2H, t, J=6.6 Hz), 3.802 (4H, m), 2.988 (2H, m), 2.815 (2H, t, J=7.2 Hz), 2.179 (2H, m), 1.813 (2H, quintet, J=7.0 Hz), 1.601 (1H, m), 1.455 (2H, m), 1.378-1.280 (14H, m), 0.878 (3H, t, J=6.6 Hz). $^{31}$P-NMR(CDCl$_3$/TFA-d): δ=−2.80. HRMS (ESI-TOF, [M-H]$^-$): Calcd for C$_{28}$H$_{45}$NO$_{10}$P$^-$: 586.2787. Found: 586.2786. Mp: 147.8° C.-148.8° C., white cube. Anal. Calcd. for C$_{28}$H$_{46}$NO$_{10}$P.0.8CF$_3$COOH: C, 52.37; H, 6.95; N, 2.06. Found: C, 52.15; H, 7.05; N, 2.00.

Example 9

Synthesis of (2S)-2-amino-3-(hydroxyl-{(3R,4R)-3-[3-(2-undecyloxy-phenyl)-propionyloxy]-tetrahydropyran-4-yloxy}-phosphoryloxy)-propionic acid

[Formula 35]

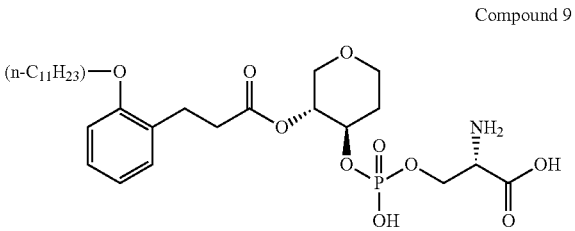

Compound 9

Synthesis was performed by the same method as Example 8 other than using Intermediate 8-2-2 instead of Intermediate 8-2-1, and column chromatography (chloroform:methanol:acetic acid=9:1:1-8:1:1-7:1:2) was performed in the final step to purify the product and to thus obtain acetic acid salt (92.1 mg, 0.157 mmol, 89%, white powder) of the title compound. In addition, from that obtained acetic acid salt, TFA salt (white powder) of the title compound was obtained.

$^1$H-NMR(CDCl$_3$/TFA-d): δ=7.202 (1H, m), 7.053 (1H, d, J=6.4 Hz), 6.879 (2H, m), 4.839 (1H, brs), 4.648 (2H, brs), 4.468 (2H, m), 3.962 (4H, m), 3.825 (1H, m), 3.714 (1H, dd, J=2.8, 12.4 Hz), 2.954 (2H, m), 2.782 (2H, t, J=7.2 Hz), 2.108 (1H, m), 1.791 (3H, m), 1.436 (2H, m), 1.363-1.228 (14H, m), 0.879 (3H, t, J=6.8 Hz). $^{31}$P-NMR(CDCl$_3$/TFA-d): δ=−2.77. HRMS (ESI-TOF, [M-H]$^-$): Calcd for C$_{28}$H$_{45}$NO$_{10}$P$^-$: 586.2787. Found: 586.2786. Mp: 122.0° C.-123.0° C., colorless cube. Anal. Calcd. for C$_{28}$H$_{46}$NO$_{10}$P.0.5CF$_3$COOH: C, 54.03; H, 7.27; N, 2.17. Found: C, 54.21; H, 7.34; N, 2.14.

Example 10

Synthesis of (2S)-2-amino-3-(hydroxy-{(3S,4S)-4-[3-(2-undecyloxy-phenyl)-propionyloxy]-tetrahydropyran-3-yloxy}-phosphoryloxy)-propionic acid

[Formula 36]

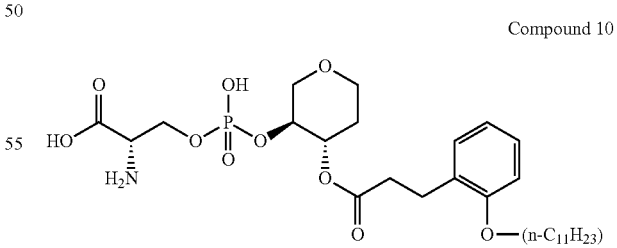

Compound 10

Synthesis was performed by the same method as Example 8 other than using (3S,4S)-tetrahydropyran-3,4-diol instead of (3R,4R)-tetrahydropyran-3,4-diol, and column chromatography (chloroform:methanol:acetic acid=10:1:1-9:1:1-8:1:1-7:1:2) was performed in the final step to purify the product and to thus obtain acetic acid salt (58.3 mg, 0.099 mmol, 100%, white powder) of the title compound. In addition, from that obtained acetic acid salt, TFA salt (white powder) of the title compound was obtained.

$^1$H-NMR(CDCl$_3$/TFA-d): δ=7.200 (1H, m), 7.077 (1H, m), 6.869 (2H, m), 5.048 (1H, brs), 4.676 (2H, brs), 4.498 (1H, brs), 4.285 (1H, brs), 4.007 (2H, t, J=6.6 Hz), 3.750 (4H, m), 2.971 (2H, m), 2.787 (2H, t, J=6.8 Hz), 2.195 (1H, brs), 1.803 (2H, m), 1.609 (1H, d, J=12.8 Hz), 1.455 (2H, m), 1.375-1.277 (14H, m), 0.881 (3H, t, J=6.8 Hz). $^{31}$P-NMR(CDCl$_3$/TFA-d): δ=−2.80. HRMS (ESI-TOF, [M-H]$^−$): Calcd for C$_{28}$H$_{45}$NO$_{10}$P$^−$: 586.2787. Found: 586.2835. Mp: 96.5° C.-98.5° C., white cube. Anal. Calcd. for C$_{28}$H$_{46}$NO$_{10}$P. 0.8CF$_3$COOH: C, 52.37; H, 6.95; N, 2.06. Found: C, 52.22; H, 6.97; N, 1.98.

Example 11

Synthesis of (2S)-2-amino-3-(hydroxy-{(3S,4S)-3-[3-(2-undecyloxy-phenyl)-propionyloxy]-tetrahydro-pyran-4-yloxy}-phosphoryloxy)-propionic acid

[Formula 37]

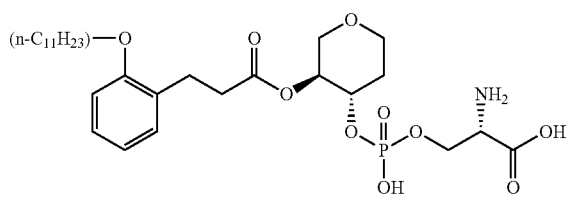

Compound 11

Synthesis was performed by the same method as Example 9 other than using (3S,4S)-tetrahydropyran-3,4-diol instead of (3R,4R)-tetrahydropyran-3,4-diol, and column chromatography (chloroform:methanol:acetic acid=10:1:1-9:1:1-8:1:1-7:1:2) was performed in the final step to purify the product and to thus obtain acetic acid salt (81.4 mg, 0.139 mmol, 97%, white powder) of the title compound. In addition, from that obtained acetic acid salt, TFA salt (white powder) of the title compound was obtained.

$^1$H-NM(CDCl$_3$/TFA-d): δ=7.200 (1H, t, J=7.4 Hz), 7.045 (1H, d, J=7.2 Hz), 6.868 (2H, m), 4.817 (1H, brs), 4.625 (2H, brs), 4.478 (2H, brs), 4.013-3.809 (5H, m), 3.712 (1H, d, J=11.2 Hz), 2.945 (2H, m), 2.772 (2H, t, J=6.8 Hz), 2.076 (1H, brs), 1.793 (3H, m), 1.442 (2H, m), 1.367-1.281 (14H, m), 0.883 (3H, t, J=6.6 Hz). $^{31}$P-NMR(CDCl$_3$/TFA-d): δ=−3.05. HRMS (ESI-TOF, [M-H]$^−$): Calcd for C$_{28}$H$_{45}$NO$_{10}$P$^−$: 586.2787. Found: 586.2827. Mp: 132.8° C.-134.8° C., white cube. Anal. Calcd. for C$_{28}$H$_{46}$NO$_{10}$P.0.5 CF$_3$COOH: C, 54.03; H, 7.27; N, 2.17. Found: C, 53.68; H, 7.24; N, 2.10.

Example 12

Synthesis of (2S)-2-amino-3-({(3S,4S)-3-[3-(5-tert-butyl-2-undecyloxy-phenyl)-propionyloxy]-tetra-hydro-pyran-4-yloxy}-hydroxy-phosphoryloxy)-propionic acid

[Formula 38]

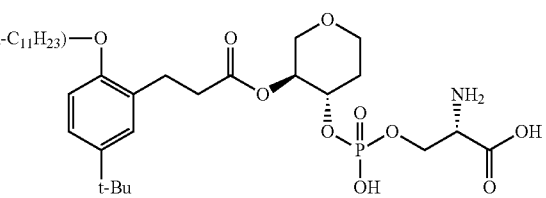

Compound 12

Synthesis was performed by the same method as Example 11 other than using acyl side chain synthesized using 3-(5-tert-butyl-2-undecyloxy-phenyl)-propionic acid instead of Compound 92, and column chromatography (chloroform:methanol:acetic acid=10:1:1-9:1:1-8:1:1-7:1:2) was performed in the final step to purify the product and to thus obtain acetic acid salt of the title compound. In addition, from that obtained acetic acid salt, TFA salt (white powder) of the title compound was obtained.

$^1$H-NMR(CDCl$_3$/TFA-d): δ=7.232 (1H, dd, J=2.0, 8.4 Hz), 7.106 (1H, d, J=2.0 Hz), 6.843 (1H, d, J=8.4 Hz), 4.850 (1H, brs), 4.651 (2H, brs), 4.514 (2H, brs), 4.016-3.905 (4H, m), 3.828 (1H, d, J=10.4 Hz), 3.703 (1H, d, J=10.8 Hz), 2.934 (2H, t, J=6.8 Hz), 2.769 (2H, m), 1.782 (3H, m), 1.449-1.264 (25H, m), 0.873 (3H, t, J=6.6 Hz). $^{31}$P-NMR (CDCl$_3$/TFA-d): δ=−2.83. HRMS (ESI-TOF, [M-H]$^−$): Calcd for C$_{32}$H$_{53}$NO$_{10}$P$^−$: 642.3413. Found: 642.3437. Mp: 144.0° C.-144.5° C., white powder. Anal. Calcd. for C$_{32}$H$_{54}$NO$_{10}$P.0.7CF$_3$COOH: C, 55.44; H, 7.62; N, 1.94. Found: C, 55.72; H, 7.74; N, 1.98.

Example 13

Synthesis of (2S)-2-amino-3-[hydroxyl-((2R,3S)-3-{3-[2-(3-phenoxy-benzyloxy)-phenyl]-propionyloxy}-tetrahydro-pyran-2-ylmethoxy)-phosphoryloxy]-propionic acid

[Formula 39]

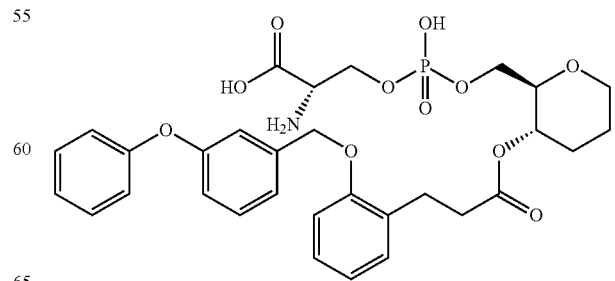

Compound 13

Synthesis of Intermediate 13-1

[Formula 40]

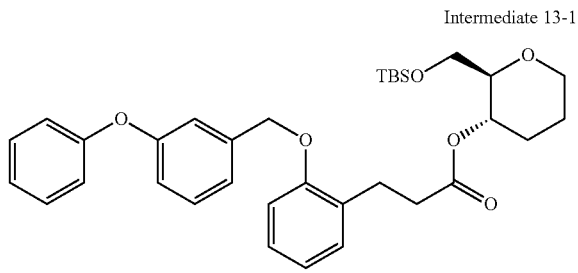

Intermediate 13-1

Compound 100 (260.2 mg, 0.747 mmol) synthesized by Scheme 10 shown below was added to a dichloromethane (2 mL) solution of (2R,3S)-2-(tert-butyldimethyl-silyloxymethyl)-tetrahydropyran-3-ol (184.0 mg, 0.747 mmol), DIC (122.5 mg, 0.971 mmol) and DMAP (9.0 mg, 0.075 mmol) at 0° C., then the solution was stirred at room temperature for 16 hours. The obtained solution was diluted with water (7 mL) and dichloromethane (7 mL) and the aqueous layer was separated and extraction was performed three times with dichloromethane (7 mL×3). The organic layer was collected and dried with magnesium sulfate, then the solvent was distilled. The residue was purified by column chromatography (hexane:ethyl acetate=15:1) to give a mixture of the title compound 13-1 (324.5 mg, 0.563 mmol, 74%, colorless oil-like matter).

$^1$H-NMR (CDCl$_3$): δ(ppm): δ=7.369-7.321 (m, 3H), 7.189-7.077 (m, 5H), 7.037-7.006 (m, 2H), 6.963-6.936 (m, 1H), 6.913-6.853 (m, 2H), 5.071 (s, 2H), 4.693-4.631(m, 1H), 3.951-3.912 (m, 1H), 3.683-3.586 (m, 2H), 3.357-3.256 (m, 2H), 2.982-2.943 (m, 2H), 2.607-2.567 (m, 2H), 2.180-2.140 (m, 1H), 1.769-1.560 (m, 2H), 1.410-1.263 (m, 1H), 0.871 (s, 9H), 0.018-0.013(m, 6H). $^{13}$C-NMR (CDCl$_3$): δ(ppm): δ=172.18, 157.68, 156.91, 156.37, 139.33, 130.17, 129.91, 129.80, 129.05, 127.62, 123.48, 121.52, 120.85, 119.16, 117.89, 117.14, 111.61, 80.54, 69.33, 68.35, 67.59, 63.36, 34.37, 29.16, 26.20, 25.99, 24.95, 18.46, −5.27, −5.33. HRMS (ESI-TOF [M+Na]$^+$): Calcd. for C$_{34}$H$_{44}$NaO$_6$Si$^+$599.2799. Found 599.2816. Anal. Calcd. for C, 69.47%; H, 7.76%; N, 0.00%. Found C, 69.70%; H, 7.53%; N, 0.00%.

Synthesis of Intermediate 13-2

[Formula 41]

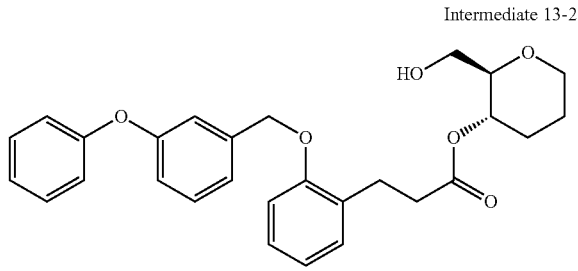

Intermediate 13-2

Drops of HF.pyridine (345.5 μL) were added to a THF (3 mL) and pyridine (150 μL) mixed solution of Intermediate 13-2, and the solution was stirred for 19 hours. The obtained solution was diluted with water (10 mL) and dichloromethane (10 mL), then the aqueous layer was separated and extraction was performed three times with dichloromethane (10 mL×3). The organic layer was collected and dried with magnesium sulfate, then the solvent was distilled. The residue was purified by column chromatography (hexane:ethyl acetate=2:1) to give the title compound (254.6 mg, 0.551 mmol, 98%, white solid).

$^1$H-NMR (CDCl$_3$): δ(ppm): δ=7.391-7.272 (m, 3H), 7.226-7.125 (m, 5H), 7.074-7.043(m, 2H), 6.997-6.971(m, 1H), 6.945-6.887 (m, 2H), 5.082 (s, 2H), 4.743-4.679(m, 1H), 3.985-3.946(m, 1H), 3.607-3.578(m, 1H), 3.465-3.334 (m, 2H), 3.282-3.239(m, 1H), 3.007(t, 2H, J=7.6 Hz), 2.675-2.616(m, 3H), 2.169-2.130(m, 1H), 1.805-1.637(m, 2H), 1.517-1.414(m, 1H). $^{13}$C-NMR (CDCl$_3$): δ(ppm): δ=172.78, 157.72, 156.95, 156.40, 149.76, 139.35, 136.05, 130.25, 129.96, 129.85, 128.83, 127.76, 123.54, 121.58, 120.90, 119.19, 117.93, 117.17, 111.69, 79.95, 69.33, 68.25, 67.66, 62.15, 60.39, 34.28, 29.14, 26.32, 25.10, 14.24. HRMS (ESI-TOF [M+Na]$^+$): Calcd. for C$_{28}$H$_{30}$NaO$_6$$^+$485.1935. Found 485.1912. Anal. Calcd. for C, 70.61%; H, 6.42% (CH$_2$Cl$_2$×0.1); N, 0.00%. Found C, 70.61%; H, 6.29%; N, 0.00%.

Synthesis of Intermediate 13-3

[Formula 42]

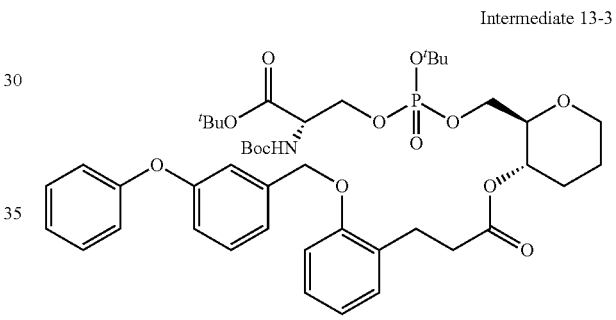

Intermediate 13-3

To remove the contained water, phosphoramidite 6 (89.2 mg, 0.198 mmol) synthesized by Scheme 9 shown below was dissolved in dichloromethane (1 mL) and toluene (0.1 mL), then the solvent was distilled under vacuum. To the obtained residue, Intermediate 13-2 (137.1 mg, 0.160 mmol) was added, then dichloromethane (1 mL) and toluene (0.1 mL) were added, and the solvent was distilled under vacuum. The residue was dissolved in dichloromethane (1 mL) under an argon atmosphere, then a THF (1 mL) solution of 1H-tetrazole (16.0 mg, 0.229 mmol) was added at room temperature. White powders precipitated after a few minutes. The reaction mixture was stirred for 19 hours at room temperature, diluted with dichloromethane (8 ml), and a saturated NaHCO$_3$ solution (10 ml) was added to complete the reaction, and extraction was performed three times with dichloromethane (8 ml×3). The organic layer was collected and dried with magnesium sulfate, then the solvent was distilled. The residue was purified by column chromatography (hexane:ethyl acetate=2:1), to give a trivalent phosphodiester intermediate (65.8 mg, 0.0797 mmol, 40.3%). The obtained intermediate was dissolved in dichloromethane (1 mL) under an argon atmosphere. Tert-butylhydroperoxide (decane solution of TBHP (5.0-6.0 M, 0.0318 mL, 0.159 mmol)) was added at room temperature, and the mixture was further stirred at room temperature for 1 hours. The solvent of the obtained solution was distilled, and the residue was purified by column chromatography (hexane:

acetone=4:1) to give the title compound (60.8 mg, 0.0722 mmol, 90.8% (2 steps: 36.5%), colorless oil-like matter).

$^1$H-NMR (CDCl$_3$): δ(ppm): δ=7.262-7.216 (m, 3H), 7.084-6.994 (m, 5H), 6.939-6.909(m, 2H), 6.868-6.842(m, 1H), 6.817-6.767(m, 2H), 5.491 (brs, 1H), 4.986 (s, 2H), 4.581-4.493 (m, 1H), 4.249-4.232 (m, 2H), 4.157-4.107 (m, 1H), 3.983-3.831(m, 3H), 3.379-3.333(m, 1H), 3.292-3.216 (m, 1H), 2.908-2.859 (m, 2H), 2.550-2.504 (m, 2H), 2.102 (m, 1H), 1.705-496 (m, 2H), 1.395-1.173 (28H). $^{13}$C-NMR (CDCl$_3$): δ(ppm): δ=172.00, 171.97, 168.43, 168.40, 157.73, 157.05, 156.46, 139.43, 139.40, 130.11, 130.07, 129.83, 129.71, 129.14, 129.09, 127.57, 127.54, 123.39, 121.56, 120.92, 119.09, 117.91, 117.90, 117.24, 111.90, 83.55, 82.35, 82.41, 78.22, 78.20, 28.15, 78.13, 69.57, 68.12, 68.04, 67.47, 67.34, 66.82, 66.76, 66.56, 66.50, 34.25, 29.77, 29.72, 29.08, 29.02, 28.32, 27.97, 27.95, 26.05, 26.04, 24.78, 24.73. $^{31}$P-NMR (CDCl$_3$): δ (ppm): δ=−5.57, −5.79. HRMS (ESI-TOF [M+Na]$^+$): Calcd. for C$_{44}$H$_{60}$NNaO$_{13}$P$^+$864.3700. Found 864.3701. Anal. Calcd. for C, 60.58%; H, 7.27%; N, 1.61%. Found C, 60.18%; H, 6.89%; N, 1.59%.

Synthesis of Compound 13

[Formula 43]

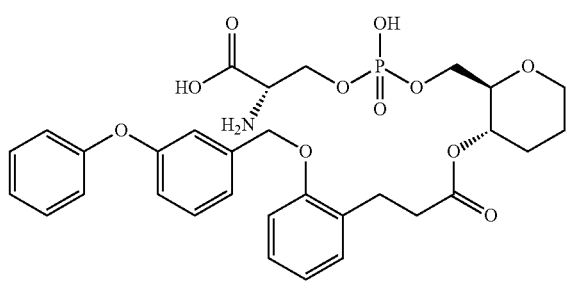 [SMILES: N[C@@H](COP(=O)(O)OC[C@H]1OCCC[C@@H]1OC(=O)CCc1ccccc1OCc1cccc(Oc2ccccc2)c1)C(=O)O]

Compound 13

Intermediate 13-3 (62.5 mg, 0.0742 mmol) that has a protection group was dissolved in TFA (2 mL), and the mixture was stirred at room temperature for 2.5 hours, then the solvent was distilled. The residue was purified by column chromatography (chloroform:methanol:acetic acid=6:1:2-5:1:4) to give TFA salt of the title compound (50.9 mg, 0.0808 mmol, 109%, white powder).

$^1$H-NMR (CDCl$_3$): δ(ppm): δ=7.386-7.343 (m, 3H), 7.239-7.094 (m, 5H), 7.041-7.022 (m, 2H), 6.988-6.908 (m, 3H), 5.115 (s, 2H), 4.859 (m, 1H), 4.628 (m, 2H), 4.497-4.444(m, 1H), 4.094-4.025 (m, 3H), 3.566-3.549 (m, 1H), 3.462 (m, 1H), 2.995-2.960 (m, 2H), 2.789-2.690 (m, 2H), 2.064-2.041(m, 1H), 1.727 (m, 2H), 1.515-1.417 (m, 1H). $^{31}$P-NMR (CDCl$_3$): δ(ppm): δ=−1.86. HRMS (ESI-TOF [M-H]$^−$): Calcd. for C$_{31}$H$_{35}$NO$_{11}$P$^−$ 628.1953. Found 628.1959. Anal. Calcd. for C, 53.30%; H, 5.02%; N, 1.88%. Found C, 53.37%; H, 5.11%; N, 1.79%. m.p 70-77° C.

Example 14

Synthesis of (2S)-2-amino-3-(hydroxy-{(2R,3S)-3-[3-(2-undecyloxy-phenyl)-propionyloxy]-tetrahydro-pyran-2-ylmethoxy}-phosphoryloxy)-propionic acid

[Formula 44]

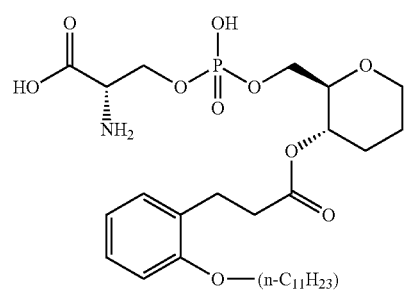

Compound 14

Synthesis was performed by the same method as Example 13 other than using Compound 92 instead of Compound 100 synthesized by Scheme 10 shown below, and column chromatography (chlorofolin:methanol:acetic acid=7:1:1-6:1:4) was performed in the final step to purify the product and to thus obtain acetic acid salt (16.0 mg, 0.0266 mmol, 105.1%, white powder) of the title compound. In addition, from that obtained acetic acid salt, TFA salt (white powder) of the title compound was obtained.

$^1$H-NMR (CDCl$_3$): δ (ppm): δ=7.098-7.062(m, 1H), 6.944-6.926(m, 1H), 6.774-6.737 (m, 2H), 4.744(brs, 1H), 4.495-4.395(m, 3H), 3.958-3.815(m, 5H), 3.451-3.366(m, 2H), 2.811-2.798(m, 2H), 2.679-2.590(m, 2H), 1.980-1.956 (m, 1H), 1.706-1.637(m, 4H), 1.397-1.106(m, 14H), 0.776-0.742(m, 3H). $^{31}$P-NMR (CDCl$_3$): δ(ppm): δ=−1.69. HRMS (ESI-TOF: [M-H]$^−$): Calcd. for C$_{29}$H$_{47}$NO$_{10}$P$^−$ 600.2943. Found 600.2917.

Example 15

Synthesis of (9Z)-Octadeca-9-enoic acid (2R,3R)-3-[((2S)-2-amino-2-carboxy-ethoxy)-hydroxy-phosphoryloxy]-tetrahydropyran-2-ylmethyl ester

[Formula 45]

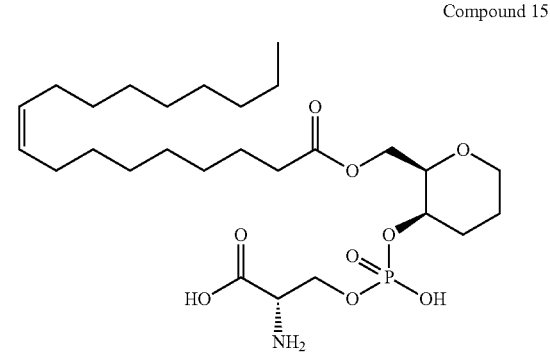

Compound 15

Synthesis was performed by basically the same method as Example 13, but (2R,3S)-2-(tert-butyldimethyl-silyloxymethyl)-tetrahydro-pyran-3-ol and phosphoramidite 6 were reacted first, and then oleoyl chloride was reacted instead of Compound 100. Further, column chromatography (chloroform:methanol:acetic acid=8:1:1-6:1:3) was performed in the final step to purify the product and to thus obtain TFA salt (62.4 mg, 0.111 mmol, 75.6%, white powder) of the title compound was obtained.

$^1$H-NMR (CDCl$_3$): δ(ppm): δ=5.398-5.255(m, 1H), 5.102-5.042(m, 0.3H), 4.637(brs, 2H), 4.510(brs, 2H), 4.333-4.312(m, 1H), 4.189-4.161(m, 2H), 3.885-3.871(m, 1H), 3.677-3.619(m, 1H), 2.389-2.352(m, 2H), 2.177-2.149 (m, 1H), 2.059-1.969(m, 3), 1.824-1.793(m, 1H), 1.646-1.573(m, 5H), 1.262(brs, 20H), 0.891-0.857(m, 3H). $^{13}$C-NMR (CDCl$_3$): δ(ppm): δ=177.21, 156.73, 154.28, 129.74, 128.02, 127.84, 120.54, 111.8572.12, 68.44, 68.37, 64.81, 63.56, 33.95, 33.93, 31.87, 31.25, 29.57, 29.53, 29.30, 29.25, 29.08, 28.22, 25.99, 25.92, 22.62, 19.14, 13.93. $^{31}$P-NMR (CDCl$_3$): δ(ppm): δ=−2.87. HRMS (ESI-TOF: [M-H]$^-$): Calcd. for C$_{27}$H$_{49}$NO$_9$P$^-$ 562.3150. Found 562.3182. Anal. Calcd. for C, 51.40%; H, 7.59%; N, 2.07%; O, 25.97%; P, 4.57%. Found C, 51.00%; H, 7.47%; N, 2.02%; (+CF$_3$COOH). m.p 70-80° C.

Example 16

Synthesis of (2S)-2-amino-3-(hydroxyl-{(2R,3R)-2-[3-(2-undecyloxy-phenyl)-propionylmethoxy]-tetrahydropyran-3-yloxy}-phosphoryloxy)-propionic acid

[Formula 46]

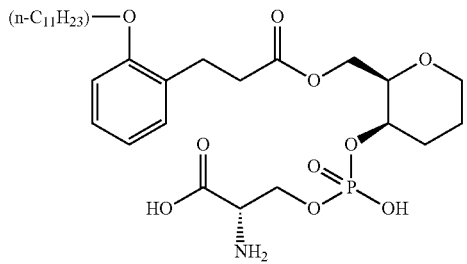

Compound 16

Synthesis was performed by the same method as Example 15 other than using Compound 92 instead of oleoyl chloride, and column chromatography (chloroform:methanol:acetic acid=8:1:1-6:1:3) was performed in the final step to purify the product and to thus obtain acetic acid salt (80.4 mg, 0.134 mmol, 86%, white powder) of the title compound. In addition, from that obtained acetic acid salt, TFA salt (white powder) of the title compound was obtained.

$^1$H-NMR(CDCl$_3$): δ(ppm): δ=7.230-7.171(m, 1H), 7.070-7.053(m, 1H), 6.873-6.799(m, 2H), 4.607-4.583(m, 2H), 4.451(brs, 2H), 4.334-4.285(m, 1H), 4.172-4.131(m, 2H), 3.980(t, 2H, J=6.8 Hz), 3.767-3.751(m, 1H), 3.625-3.567(m, 1H), 2.933-2.900(m, 2H), 2.748-2.712(m, 2H), 2.163-2.133(m, 1H), 2.010-1.981(m, 1H), 1.827-1.757(m, 3H), 1.537-1.409(m, 3H), 1.365-1.278(m, 15H), 0.885(t, 3H, J=6.8 Hz). $^{13}$C-NMR (CDCl$_3$): δ(ppm): δ=177.20, 156.73, 154.28, 129.74, 128.02, 127.84, 120.54, 111.85, 77.16, 72.11, 68.45, 68.36, 64.80, 63.54, 33.96, 33.93, 31.87, 31.24, 29.59, 29.53, 29.30, 29.25, 29.08, 28.23, 25.99, 25.92, 22.61, 19.14, 13.92. $^{31}$P-NMR (CDCl$_3$): δ(ppm): δ=−2.96. HRMS (ESI-TOF: [M-H]$^-$): Calcd. for C$_{29}$H$_{47}$NO$_{10}$P$^-$ 600.2943. Found 600.2925. Anal. Calcd. for C, 53.38%; H, 7.15%; N, 2.06%; O, 26.83%; P, 4.33%. Found C, 53.75%; H, 7.30%; N, 2.08% (+CF$_3$COOH×0.7). m.p 69-85° C.

Example 17

Synthesis of (2S)-2-amino-3-[hydroxyl-((2R,3R)-2-{3-[2-(3-phenoxy-benzyloxy)-phenyl]-propionyl-methoxy}-tetrahydropyran-3-yloxy)-phosphoryloxy]-propionic acid

[Formula 47]

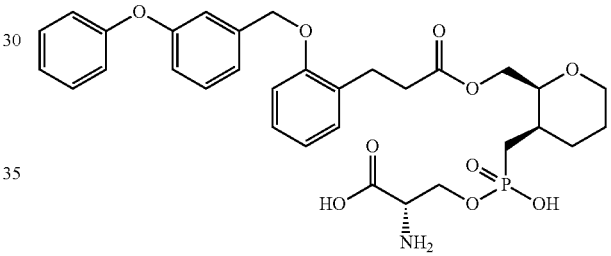

Compound 17

Synthesis was performed by the same method as Example 15 other than using Compound 100 instead of oleoyl chloride, and column chromatography (chloroform:methanol:acetic acid=8:1:1-6:1:3) was performed in the final step to purify the product and to thus obtain acetic acid salt (35.3 mg, 0.0560 mmol, 64%, white powder) of the title compound. In addition, from that obtained acetic acid salt, TFA salt (white powder) of the title compound was obtained.

$^1$H-NMR (CDCl$_3$): δ(ppm): δ=7.364-7.325(m, 3H), 7.214-7.085(m, 5H), 7.024-7.005(m, 2H), 6.970-6.945(m, 1H), 6.909-6.889(m, 2H), 5.082(s, 2H), 4.665(brs, 2H), 4.510-4.370(m, 2H), 4.306(brs, 1H), 4.147-4.122(m, 2H), 3.758(brs, 1H), 3.602-3.550(m, 1H), 2.958(brs, 2H), 2.744-2.727(m, 2H), 2.199-2.156(m, 1H), 1.994-1.982(m, 1H), 1.733(brs, 1H), 1.534-1.509(m, 1H). $^{13}$C-NMR (CDCl$_3$): δ(ppm): δ=157.51, 156.59, 156.13, 139.00, 129.92, 129.84, 128.14, 127.91, 123.81, 121.89, 121.22, 119.07, 118.00, 117.27, 112.33, 77.11, 72.47, 69.76, 68.41, 64.78, 63.53, 34.13, 31.15, 28.19, 25.99, 25.76, 19.06. $^{31}$P-NMR (CDCl$_3$): δ(ppm): δ=0.97. HRMS (ESI-TOF: [M-H]$^-$): Calcd. for C$_{31}$H$_{35}$NO$_{11}$P$^-$ 628.1953. Found 628.1915. Anal. Calcd. for C, 51.19%; H, 5.22%; N, 1.81% (CF$_3$CO$_2$H×1, H$_2$O×1.7. Found C, 51.48%; H, 5.02%; N, 1.70%. m.p 79-85° C.

Example 18

Synthesis of (2S)-2-amino-3-[hydroxyl-((2R,3R))-3-{3-[2-(3-phenoxy-benzyloxy)-phenyl]-propionyloxy}-tetrahydro-pyran-2-ylmethoxy)-phosphoryloxy]-propionic acid

[Formula 48]

Compound 18

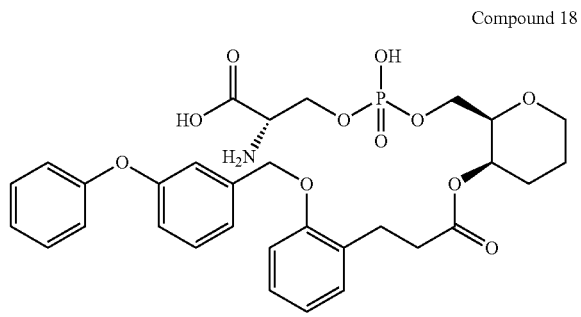

Synthesis was performed by the same method as Example 13 other than using (2R,3R)-2-(tert-butyldimethyl-silyloxymethyl)-tetrahydro-pyran-3-ol instead of (2R,3S)-2-(tert-butyldimethyl-silyloxymethyl)-tetrahydro-pyran-3-ol, and column chromatography (chloroform:methanol:acetic acid=6:1:2-5:1:3) was performed in the final step to purify the product and to thus obtain acetic acid salt (8.3 mg, 0.0132 mmol, 66.9%, white powder) of the title compound. In addition, from that obtained acetic acid salt, TFA salt (white powder) of the title compound was obtained.

$^1$H-NMR (CDCl$_3$): δ(ppm): δ=7.357-7.314 (m, 3H), 7.206-7.065 (m, 5H), 7.011-6.878 (m, 5H), 5.802 (s, 2H), 5.004 (brs, 1H), 4.596 (brs, 2H), 4.489 (brs, 1H), 4.142-4.114 (m, 1H), 3.989-3.975 (m, 2H), 3.852-3.841 (m, 1H), 3.629-3.577 (m, 1H), 3.028-2.932 (m, 2H), 2.810-2.711(m, 2H), 1.869-1.838(m, 1H), 1.778-1.640 (m, 2H), 1.493-1.411 (m, 1H). $^{31}$P-NMR (CDCl$_3$): δ(ppm): δ=−1.78. HRMS (ESI-TOF: [M-H]$^-$): Calcd. for C$_{31}$H$_{35}$NO$_{11}$P 628.1953. Found 628.1967. Anal. Calcd. for C, 59.14%; H, 5.76%; N, 2.22%; [H$_2$O×1, CF$_3$CO$_2$H×1]; C, 52.04%; H, 5.16%; N, 1.84%]. Found C, 52.12%; H, 5.46%; N, 1.81%. m.p 65-75° C.

Example 19

Synthesis of (2S)-2-amino-3-(hydroxyl-{(2R,3S)-2-[3-(2-undecyloxy-phenyl)-propionyloxymethyl]-3,6-dihydro-2H-pyran-3-yloxy}-phosphoryloxy)-propionic acid

[Formula 49]

Compound 19

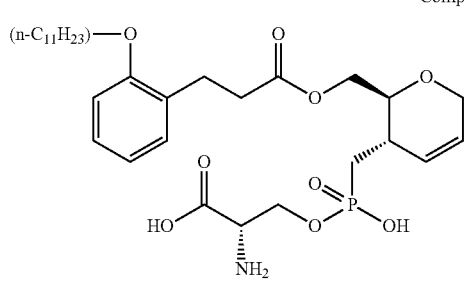

Synthesis was performed by the same method as Example 16 other than using (2R,3S)-2-(tert-butyldimethyl-silyloxymethyl)-3,6-dihydro-2H-pyran-3-ol instead of (2R,3R)-2-(tert-butyldimethyl-silyloxymethyl)-tetrahydropyran-3-ol, and column chromatography (chloroform:methanol:acetic acid=6:1:2-4:1:3) was performed in the final step to purify the product and to thus obtain acetic acid salt of the title compound. In addition, from that obtained acetic acid salt, TFA salt (15.3 mg, 0.0255 mmol, 58.39% (2 steps: 20.9%), white powder) of the title compound was obtained.

$^1$H-NMR (CDCl$_3$): δ(ppm): δ=7.214-7.176 (m, 1H), 7.076-7.059 (m, 1H), 6.895-6.829 (m, 2H), 6.027-6.003 (m, 1H), 5.876-5.809 (m, 1H), 4.738-4.424 (m, 5H), 4.310-4.254 (m, 3H), 4.011-3.977 (m, 2H), 3.864-3.861 (m, 1H), 2.951-2.866 (m, 2H), 2.773-2.756 (m, 2H), 1.816-1.746 (m, 2H), 1.427-1.267 (m, 16H), 0.890-0.857 (m, 3H). $^{31}$P-NMR (CDCl$_3$): δ(ppm): δ=−1.85. HRMS (ESI-TOF [M-H]$^-$): Calcd. for C$_{29}$H$_{49}$NO$_{10}$P$^-$ 598.2787. Found 598.2779.

Example 20

Synthesis of (9Z)-Octadeca-9-enoic acid (2R,3S)-3-[((2S)-2-amino-2-carboxy-ethoxy)-hydroxy-phosphoryloxy]-tetrahydro-pyran-2-ylmethyl ester

[Formula 50]

Compound 20

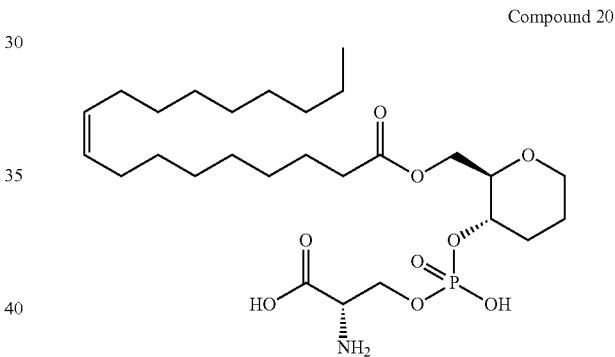

Synthesis was performed by the same method as Example 15 other than using (2R,3S)-2-(tert-butyldimethyl-silyloxymethyl)-tetrahydro-pyran-3-ol instead of (2R,3R)-2-(tert-butyldimethyl-silyloxymethyl)-tetrahydro-pyran-3-ol, and column chromatography (chloroform:methanol:acetic acid=8:1:1-6:1:3) was performed in the final step to purify the product and to thus obtain acetic acid salt (75.9 mg, 0.135 mmol, 94%, white powder) of the title compound. In addition, from that obtained acetic acid salt, TFA salt (white powder) of the title compound was obtained.

$^1$H-NMR (CDCl$_3$): δ(ppm): δ=5.398-5.306(m, 1H), 5.104-5.042(m, 1H), 4.605(brs, 2H), 4.493(brs, 1H), 4.397-4.396(m, 1H), 4.272(m, 1H), 4.120-4.095(m, 2H), 3.602-3.485(m, 2H), 2.390-2.287(m, 3H), 2.035-1.966(m, 2H), 1.794-1.573(m, 7H), 1.261(m, 20H), 0.890-0.856(m, 3H). $^{13}$C-NMR (CDCl$_3$): δ(ppm): δ=178.27, 169.01, 130.12, 129.65, 81.07, 78.37, 72.42, 67.81, 63.87, 63.42, 34.20, 33.56, 31.79, 29.68, 29.57, 29.45, 29.25, 29.19, 29.07, 28.96, 28.90, 27.12, 27.06, 24.88, 24.59, 22.58, 13.86. $^{31}$P-NMR (CDCl$_3$): δ(ppm): δ=−3.10. HRMS (ESI-TOF: [M-H]$^-$): Calcd. for C$_{27}$H$_{49}$NO$_9$P$^-$ 562.3150. Found 562.3178. 2$^{nd}$: Anal. Calcd. for C, 52.46%; H, 7.76%; N, 2.14% (CF$_3$CO$_2$H×1). Found C, 52.20%; H, 7.72%; N, 2.16%. m.p. 70-80° C.

Example 21

Synthesis of (2S)-2-amino-3-(hydroxyl-{(2R,3S)-2-[3-(2-undecyloxy-phenyl)-propionyloxymethyl]-tetrahydro-pyran-3-yloxy}-phosphoryloxy)-propionic acid

[Formula 51]

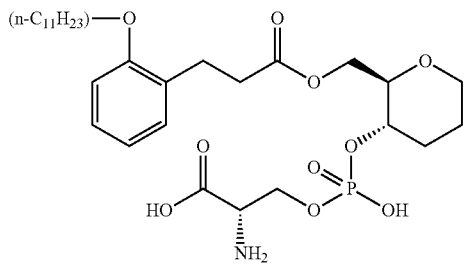

Compound 21

Synthesis was performed by the same method as Example 20 other than using Compound 92 instead of oleoyl chloride, and column chromatography (chloroform:methanol:acetic acid=8:1:1-6:1:2) was performed in the final step to purify the product and to thus obtain acetic acid salt (43.6 mg, 0.0725 mmol, 94.4%, white powder) of the title compound. In addition, from that obtained acetic acid salt, TFA salt (white powder) of the title compound was obtained.

$^1$H-NMR (CDCl$_3$): δ(ppm): δ=7.227-7.171(m, 1H), 7.120-7.057(m, 1H), 6.877-6.805(m, 2H), 4.597(brs, 2H), 4.450-4.399(m, 2H), 4.215-4.070(m, 3H), 3.979(t, 2H, J=6.8 Hz), 3.575-3.454(m, 2H), 2.939-2.903(m, 2H), 2.751-2.733(m, 2H), 2.299-2.290(m, 1H), 1.816-1.650(m, 5H), 1.427-1.271(m, 20H), 0.878(t, 3H, J=6.8 Hz). $^{31}$P-NMR (CDCl$_3$): δ(ppm): δ=−2.90. HRMS (ESI-TOF: [M-H]$^-$): Calcd. for C$_{29}$H$_{47}$NO$_{10}$P$^-$ 600.2943. Found 600.2934. Anal. Calcd. for C, 52.02%; H, 6.90%; N, 1.96%; O, 26.83%; P, 4.33%. Found C, 52.06%; H, 7.01%; N, 1.91%. m.p. 70-86° C.

Example 22

Synthesis of (2S)-2-amino-3-[hydroxyl-((2R,3S)-2-{3-[2-(3-phenoxy-benzyloxy)-phenyl]-propionyloxymethyl}-tetrahydropyran-3-yloxy)-phosphoryloxy]-propionic acid

[Formula 52]

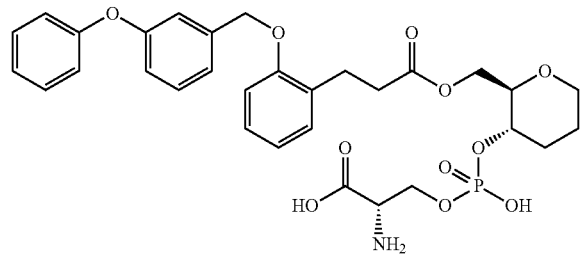 [SMILES: N[C@@H](COP(=O)(O)O[C@H]1CCCO[C@@H]1COC(=O)CCc1ccccc1OCc1cccc(Oc2ccccc2)c1)C(=O)O]

Compound 22

Synthesis was performed by the same method as Example 20 other than using Compound 100 instead of oleoyl chloride, and column chromatography (chloroform:methanol:acetic acid=8:1:1-6:1:3) was performed in the final step to purify the product and to thus obtain acetic acid salt (47.3 mg, 0.0751 mmol, 90.1%, white powder) of the title compound. In addition, from that obtained acetic acid salt, TFA salt (white powder) of the title compound was obtained.

$^1$H-NMR(CDCl$_3$): δ(ppm): δ=7.359-7.314(m, 3H), 7.203-6.879(m, 10H), 5.078(s, 2H), 4.264-4.598(m, 2H), 4.465-4.378(m, 2H), 4.209-4.064(m, 3H), 3.565-3.443(m, 2H), 2.927-2.936(m, 2H), 2.748-2.729(m, 2H), 2.308(brs, 1H), 1.781-1.694(m, 3H). $^{13}$C-NMR (CDCl$_3$): δ(ppm): δ=177.47, 157.48, 156.63, 156.12, 139.00, 129.98, 129.85, 129.81, 129.72, 128.07, 128.00, 123.75, 121.86, 121.19, 119.10, 119.07, 118.76, 118.02, 117.27, 112.35, 78.24, 72.67, 69.78, 67.70, 64.11, 63.43, 34.07, 31.17, 29.97, 25.80, 23.97. $^{31}$P-NMR (CDCl$_3$): δ(ppm): δ=−2.73. HRMS (ESI-TOF: [M-H]$^-$): Calcd. for C$_{31}$H$_{35}$NO$_{11}$P$^-$ 628.1953. Found 628.1968. Anal. Calcd. for C, 50.17%; H, 4.58%; N, 1.70%. Found C, 50.07%; H, 4.95%; N, 1.60%. m.p. 78-88° C.

Example 23

Synthesis of (9Z)-Octadeca-9-enoic acid (2R,3S)-3-[((2S)-2-amino-2-carboxy-ethoxy)-hydroxy-phosphoryloxy]-3,6-dihydro-2H-pyran-2-ylmethyl ester

[Formula 53]

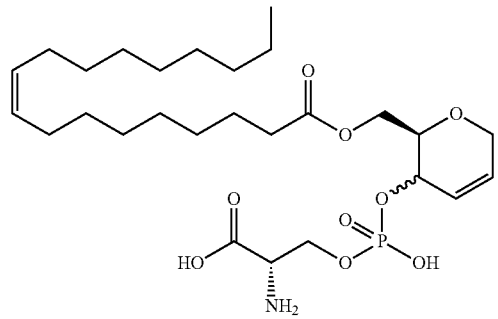 [SMILES: CCCCCCCC/C=C\CCCCCCCC(=O)OC[C@H]1OCC=C[C@@H]1OP(=O)(O)OC[C@H](N)C(=O)O]

Compound 23

Synthesis was performed by the same method as Example 20 other than using (2R,3S)-2-(tert-butyldimethyl-silyloxymethyl)-3,6-dihydro-2H-pyran-3-ol instead of (2R,3S)-2-(tert-butyldimethyl-silyloxymethyl)-tetrahydro-pyran-3-ol, and column chromatography (chloroform:methanol:acetic acid=7:1:1-6:1:4) was performed in the final step to purify the product and to thus obtain acetic acid salt (30.6 mg, 0.0616 mmol, 48%, white powder) of the title compound. In addition, from that obtained acetic acid salt, TFA salt (white powder) of the title compound was obtained.

$^1$H-NMR (CDCl$_3$): δ(ppm): δ=5.900-5.875(m, 1H), 5.803-5.718(m, 1H), 5.295-5.211(m, 1H), 5.003-4.942(m, 1H), 4.570(brs, 1H), 4.470-4.302(m, 3H), 4.183-4.142(m, 3H), 3.697-3.621(m, 1H), 2.308-2.271(m, 2H), 1.928-1.878(m, 2H), 1.552-1.496(m, 4H), 1.174(brs, 19H), 0.806-0.772(m, 3H). $^{31}$P-NMR (CDCl$_3$): δ(ppm): δ=−2.72. HRMS (ESI-TOF: [M-H]$^-$): Calcd. for C$_{27}$H$_{47}$NO$_9$P$^-$ 560.2994. Found 560.3027.

Example 24

Synthesis of (2S)-2-amino-3-[hydroxy-((2R,3S)-2-{3-[2-(3-phenoxy-benzyloxy)-phenyl]-propionyloxymethyl}-3,6-dihydro-2H-pyran-3-yloxy)-phosphoryloxy]-propionic acid

[Formula 54]

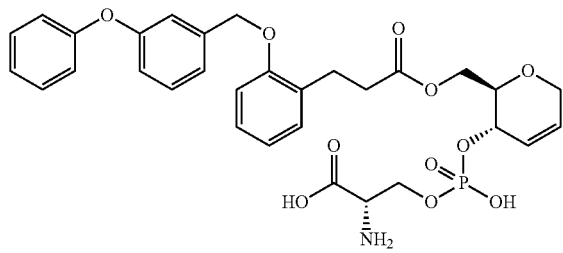 [SMILES: N[C@@H](COP(=O)(O)O[C@H]1C=CCO[C@@H]1COC(=O)CCc1ccccc1OCc1cccc(Oc2ccccc2)c1)C(=O)O]

Compound 24

Synthesis was performed by the same method as Example 23 other than using Compound 100 instead of oleoyl chloride, and column chromatography (chloroform:methanol:acetic acid=6:1:2-4:1:3) was performed in the final step to purify the product and to thus obtain acetic acid salt of the title compound. In addition, from that obtained acetic acid salt, TFA salt (12.9 mg, 0.020 mmol, 17.7%, white powder) of the title compound was obtained.

$^1$H-NMR (CDCl$_3$): δ(ppm): δ=7.364-7.302(m, 3H), 7.209-7.7.026 (m, 5H), 7.009-6.863 (m, 5H), 6.027-5.944 (m, 1H), 5.801-5.775 (m, 1H), 5.063 (s, 2H), 4.666-4.102 (m, 8H), 3.774-3.757 (m, 1H), 2.988-2.928 (m, 2H), 2.747-2.666 (m, 2H). $^{31}$P-NMR (CDCl$_3$): δ(ppm): δ=−2.66. HRMS (ESI-TOF [M-H]$^-$): Calcd. for C$_{31}$H$_{33}$NO$_{11}$P$^-$ 626.1797. Found 626.1811.

Example 25

Synthesis of (2S)-2-amino-3-(hydroxy-{(2R,3R)-2-[3-(2-undecyloxy-phenyl)-propionyloxymethyl]-3,6-dihydro-2H-pyran-3-yloxy}-phosphoryloxy)-propionic acid

[Formula 55]

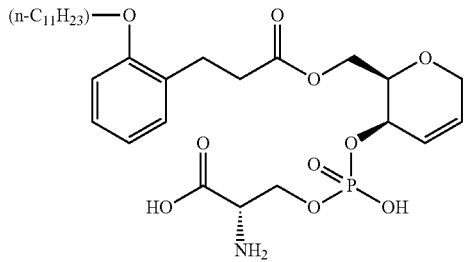

Compound 25

Synthesis was performed by the same method as Example 21 other than using (2R,3R)-2-(tert-butyldimethyl-silyloxymethyl)-3,6-dihydro-2H-pyran-3-ol instead of (2R,3S)-2-(tert-butyldimethyl-silyloxymethyl)-tetrahydropyran-3-ol, and column chromatography (chloroform:methanol:acetic acid=6:1:2-5:1:3) was performed in the final step to purify the product and to thus obtain acetic acid salt (52.1 mg, 0.0869 mmol, 77.4%, white powder) of the title compound. In addition, from that obtained acetic acid salt, TFA salt (white powder) of the title compound was obtained.

$^1$H-NMR (CDCl$_3$): δ(ppm): δ=7.201-7.057 (m, 2H), 6.866-6.829 (m, 2H), 6.126-6.018 (m, 2H), 4.603-4.189 (m, 8H), 3.976 (t, 2H, J=6.8 Hz), 3.877 (m, 1H), 2.940-2.907 (m, 2H), 2.759-2.723 (m, 2H), 1.824-1.754 (m, 2H), 1.455-1.271 (m, 16H), 0.897-0.863 (m, 3H). $^{31}$P-NMR (CDCl$_3$): δ(ppm): δ=−2.64. HRMS (ESI-TOF [M-H]$^-$): Calcd. for C$_{29}$H$_{45}$NO$_{10}$P$^-$ 598.2787. Found 598.2785.

Example 26

Synthesis of (2S)-2-amino-3-[hydroxyl-((2R,3R)-2-{3-[2-(3-phenoxybenzyloxy)-phenyl]-propionyloxymethyl}-3,6-dihydro-2H-pyran-3-yloxy)-phosphoryloxy]-propionic acid

[Formula 56]

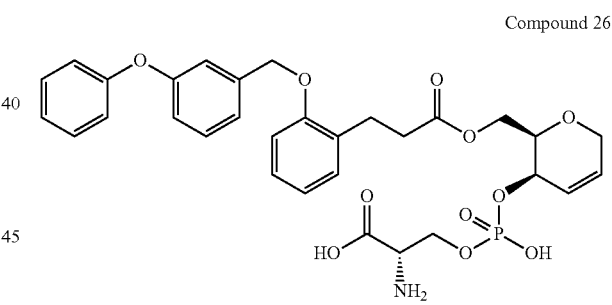

Compound 26

Synthesis was performed by the same method as Example 25 other than using Compound 100 instead of Compound 92, and column chromatography (chloroform:methanol:acetic acid=6:1:2-5:1:3) was performed in the final step to purify the product and to thus obtain acetic acid salt (13.7 mg, 0.0128 mmol, 42.6%, white powder) of the title compound. In addition, from that obtained acetic acid salt, TFA salt (white powder) of the title compound was obtained.

$^1$H-NMR (CDCl$_3$): δ(ppm): δ=7.361-7.311 (m, 3H), 7.209-7.078 (m, 5H), 7.015-6.871 (m, 5H), 6.114-6.090 (m, 1H), 5.980 (m, 1H), 5.078 (s, 2H), 4.571-4.502 (m, 3H), 4.466-4.434 (m, 1H), 4.386-4.337 (m, 2H), 4.260-4.165 (m, 2H), 3.858-3.842 (m, 1H), 3.016-2.901 (m, 2H), 2.811-2.722 (m, 2H). $^{31}$P-NMR (CDCl$_3$): δ(ppm): δ=−3.09. HRMS (ESI-TOF [M-H]$^-$): Calcd. for C$_{31}$H$_{33}$NO$_{11}$P$^-$ 626.1797. Found 626.1801. Anal. Calcd. for C, 49.13%; H, 4.24%; N, 1.64%. Found C, 48.78%; H, 4.24%; N, 1.61%.

Example 27

Synthesis of (2S,3S)-2-amino-3-[hydroxyl-((2R,3S)-3-{3-[2-(3-phenoxy-benzyloxy)-phenyl]-propionyloxy}-tetrahydro-pyran-2-ylmethoxy)-phosphoryloxy]-butyric acid

[Formula 57]

Compound 27

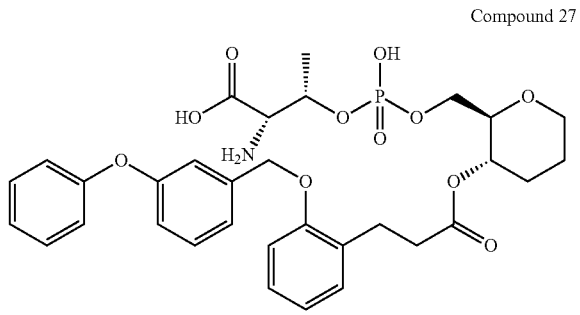

Synthesis was performed by the same method as Example 18 other than using (2R,3S)-2-(tert-butyldimethyl-silyloxymethyl)-tetrahydro-pyran-3-ol instead of (2R,3R)-2-(tert-butyldimethyl-silyloxymethyl)-tetrahydro-pyran-3-ol, and using phosphoramidite 9 instead of phosphoramidite 6, and column chromatography (chloroform:methanol: acetic acid=6:1:2-5:1:4) was performed in the final step to purify the product and to thus obtain acetic acid salt (29.1 mg, 0.0452 mmol, 166.2%, white powder) of the title compound. In addition, from that obtained acetic acid salt, TFA salt (white powder) of the title compound was obtained.

$^1$H-NMR (CDCl$_3$): δ(ppm): δ=7.366-7.328 (m, 3H), 7.221-7.096 (m, 5H), 7.027-7.006 (m, 2H), 6.976-6.956 (m, 1H), 6.923-6.889 (m, 2H), 5.178 (m, 1H), 5.091 (m, 2H), 4.483-4.429 (m, 1H), 4.304 (m, 2H), 4.210-4.139(m, 2H), 3.792-3.781(m, 1H), 3.636-3.579 (m, 1H), 2.966-2.905 (m, 2H), 2.753-2.719 (m, 2H), 2.169-2.155 (m, 1H), 2.024-1.994 (m, 1H), 1.789-1.733 (m, 1H), 1.608-1.540 (m, 4H). $^{31}$P-NMR (CDCl$_3$): δ (ppm): δ=-3.38. HRMS (ESI-TOF [M-H]$^-$): Calcd. for C$_{32}$H$_{37}$NO$_{11}$P$^-$ 642.2110 Found 642.2122. m.p 75-86° C.

Example 28

Synthesis of (2S,3S)-2-amino-3-[hydroxyl-((2R,3R)-3-{3-[2-(3-phenoxy-benzyloxy)-phenyl]-propionyloxy}-tetrahydro-pyran-2-ylmethoxy)-phosphoryloxy]-butyric acid

[Formula 58]

Compound 28

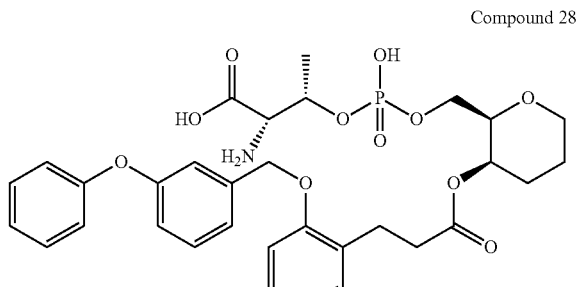

Synthesis was performed by the same method as Example 18 other than using phosphoramidite 9 instead of phosphoramidite 6, and column chromatography (chloroform:methanol:acetic acid=6:1:2-5:1:4) was performed in the final step to purify the product and to thus obtain acetic acid salt (56.3 mg, 0.0875 mmol, 87.04%, white powder) of the title compound. In addition, from that obtained acetic acid salt, TFA salt (white powder) of the title compound was obtained.

$^1$H-NMR (CDCl$_3$): δ(ppm): δ=7.388-7.348 (m, 3H), 7.234-7.096 (m, 5H), 7.044-6.972 (m, 3H), 6.940-6.906 (m, 2H), 5.115-5.025 (m, 4H), 4.237-4.139 (m, 2H), 4.028-4.011 (m, 2H), 3.858 (m, 1H), 3.646-3.591 (m, 1H), 3.031-2.997 (m, 2H), 2.861-2.734 (m, 2H), 1.875-1.671 (m, 2H), 1.567-1.560 (m, 3H), 1.474-1.443 (m, 1H), 1.356-1.293(m, 1H). $^{31}$P-NMR (CDCl$_3$): δ(ppm): δ=-3.42. HRMS (ESI-TOF [M-H]$^-$): Calcd. for C$_{32}$H$_{37}$NO$_{11}$P$^-$ 642.2110. Found 642.2117. Anal. Calcd. for C, 50.37%; H, 4.69%; N, 1.65%. Found C, 50.29%; H, 4.81%; N, 1.68%. m.p 62-72° C.

Example 29

Synthesis of (2S,3S)-2-amino-3-[hydroxy-((2R,3S)-2-{3-[2-(3-phenoxybenzyloxy)-phenyl]-propionyloxymethyl}-tetrahydro-pyran-3-yloxy)-phosphoryloxy]-butyric acid

[Formula 59]

Compound 29

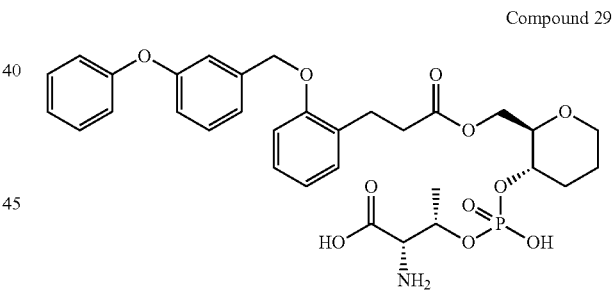

Synthesis was performed by the same method as Example 22 other than using phosphoramidite 9 instead of phosphoramidite 6, and column chromatography (chloroform:methanol:acetic acid=6:1:2-5:1:4) was performed in the final step to purify the product and to thus obtain acetic acid salt (14.3 mg, 0.0222 mmol, 138.86%, white powder) of the title compound. In addition, from that obtained acetic acid salt, TFA salt (white powder) of the title compound was obtained.

$^1$H-NMR (CDCl$_3$): δ(ppm): δ=7.357-7.311 (m, 3H), 7.201-7.060 (nm, 5H), 7.016-6.996 (m, 2H), 6.964-6.938 (m, 1H), 6.910-6.875 (m, 2H), 5.122-5.074 (m, 3H), 4.441-4.412 (m, 1H), 4.231-4.3.994 (m, 4H), 3.583-3.565 (m, 1H), 3.487-3.437 (m, 1H), 2.966-2.929 (m, 2H), 2.770-2.685 (m, 2H), 2.301-2.282 (m, 1H), 1.781-1.563 (m, 6H). $^{31}$P-NMR (CDCl$_3$): δ(ppm): δ=-4.03. HRMS (ESI-TOF [M-H]$^-$): Calcd. for C$_{32}$H$_{37}$NO$_{11}$P$^-$ 642.2110. Found 642.2117. m.p 42-54° C.

Example 30

Synthesis of (2S,3S)-2-amino-3-[hydroxy-((2R,3R)-2-{3-[2-(3-phenoxy-benzyloxy)-phenyl]-propionyloxymethyl}-tetrahydro-pyran-3-yloxy)-phosphoryloxy]-butyric acid

[Formula 60]

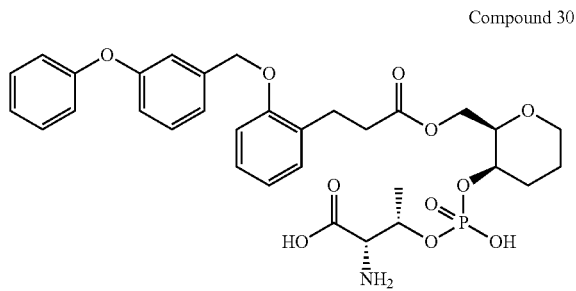

Compound 30

Synthesis was performed by the same method as Example 24 other than using (2R,3R)-2-(tert-butyldimethyl-silyloxymethyl)-tetrahydropyran-3-ol instead of (2R,3S)-2-(tert-butyldimethyl-silyloxymethyl)-tetrahydropyran-3-ol, and using phosphoramidite 9 instead of phosphoramidite 6, and column chromatography (chloroform:methanol: acetic acid=6:1:2-5:1:4) was performed in the final step to purify the product and to thus obtain acetic acid salt (15.7 mg, 0.0234 mmol, 89.35%, white powder) of the title compound. In addition, from that obtained acetic acid salt, TFA salt (white powder) of the title compound was obtained.

$^1$H-NMR (CDCl$_3$): δ(ppm): δ=7.366-7.328 (m, 3H), 7.221-7.096 (m, 5H), 7.027-7.006 (m, 2H), 6.976-6.956 (m, 1H), 6.923-6.889(m, 2H), 5.178 (m, 1H), 5.091 (s, 3H), 4.483-4.429 (m, 1H), 4.304 (m, 2H), 4.210-4.139 (m, 2H), 3.792-3.781 (m, 1H), 3.636-3.579 (m, 1H), 2.966-2.905 (m, 2H), 2.753-2.719 (m, 2H), 2.169-2.155 (m, 1H), 2.204-1.994 (1H), 1.789-1.733 (m, 1H), 1.608-1.540 (m, 1H). $^{31}$P-NMR (CDCl$_3$): δ(ppm): δ=−3.38. HRMS (ESI-TOF [M-H]$^-$): Calcd. for C$_{32}$H$_{37}$NO$_{11}$P$^-$ 642.2110. Found 642.2122. m.p 52-60° C.

Example 31

Synthesis of (2S)-2-amino-3-[hydroxy-((1R)-1-methoxymethyl-2-{3-[2-(3-phenoxy-benzyloxy)-phenyl]-propionyloxy}-ethoxy)-phosphoryloxy]-propionic acid

[Formula 61]

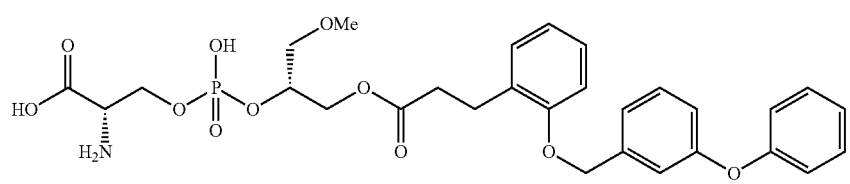 [SMILES: COC[C@H](COC(=O)CCc1ccccc1OCc1cccc(Oc2ccccc2)c1)OP(=O)(O)OC[C@H](N)C(=O)O]

Compound 31

Synthesis was performed by the same method as Example 3 other than using (2S)-3-methoxy-1,2-propanediol instead of (R)-1,2-propanediol, and column chromatography (chloroform:methanol:acetic acid=8:1:1-7:1:2) was performed in the final step to purify the product and to thus obtain acetic acid salt (100.1 mg, 0.116 mmol, 90%, white powder) of the title compound. In addition, from that obtained acetic acid salt, TFA salt (white powder) of the title compound was obtained.

$^1$H-NMR(CDCl$_3$): δ=7.347 (3H, m), 7.228-7.087 (5H, m), 7.022-6.906 (5H, m), 5.102 (2H, s), 4.655 (3H, m), 4.530 (1H, brs), 4.338 (1H, dd, J=4.4, 12.0 Hz), 4.224 (1H, dd, J=4.6, 12.0 Hz), 3.634 (2H, m), 3.467 (3H, s), 2.978 (2H, t), 2.759 (2H, t, J=7.4 Hz). $^{31}$P-NMR(CDCl$_3$): δ=−2.27. HRMS (ESI-TOF, [M-H]$^-$): Calcd for C$_{29}$H$_{33}$NO$_{11}$P$^-$:602.1797. Found: 602.1844. Mp: 51.5° C.-53.5° C., colorless solid. Anal. Calcd. for C$_{29}$H$_{34}$NO$_{11}$P.1.5CF$_3$COOH: C, 49.62; H, 4.62; N, 1.81. Found: C, 49.40; H, 4.76; N, 1.81.

The synthetic method of the phosphoric acid section (phosphoramidite) connected to an amino acid section and the side chain section used in the present invention is shown in the schemes below.

[Formula 62]

Scheme 8: Preparation of Amino Acid Section

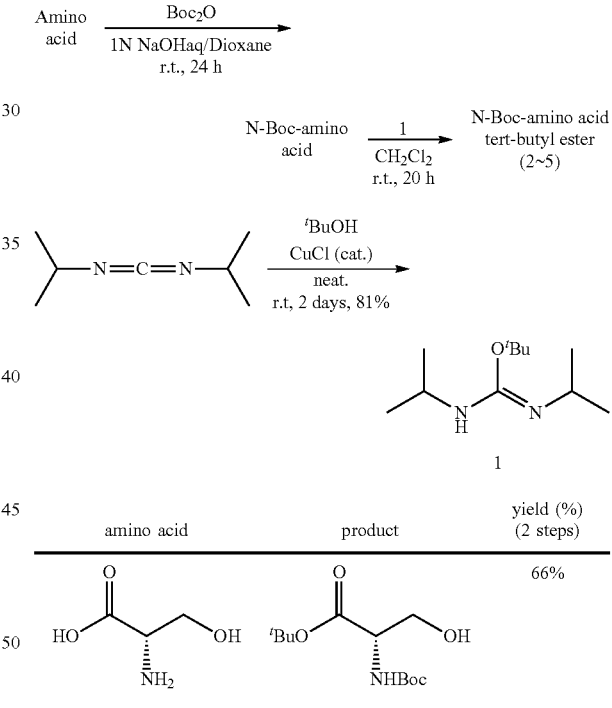

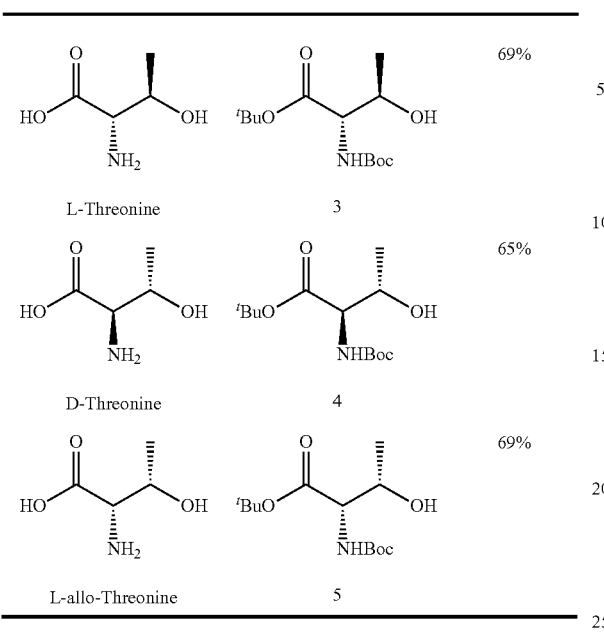
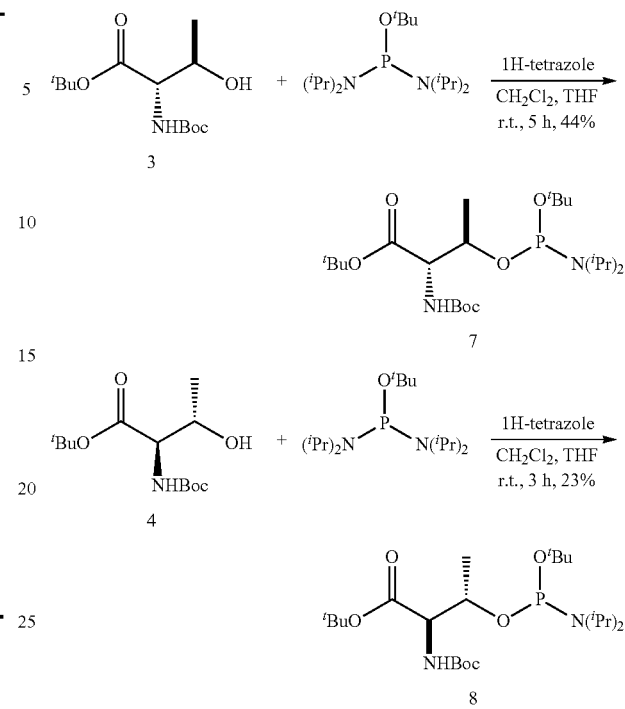
Scheme 9: Preparation of Phosphoric Acid Section (Phosphoramidite) Connected with Amino Acid Section
[Formula 63]
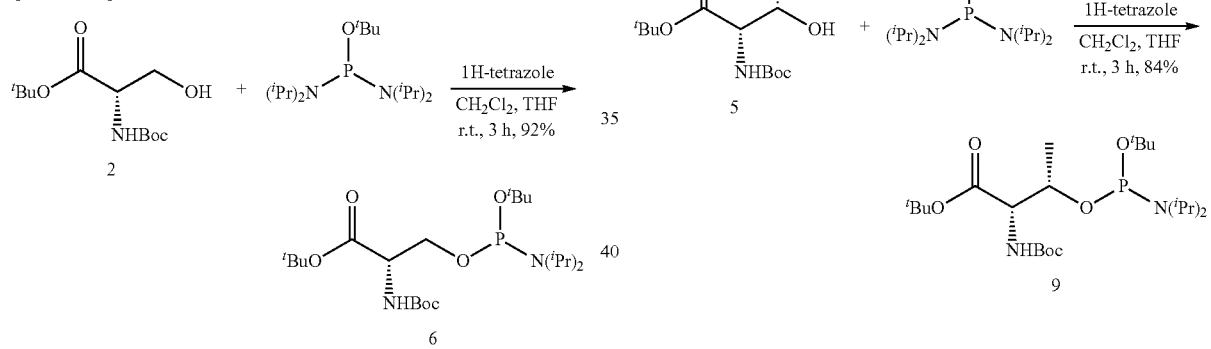

Scheme 10: Preparation of Side Chain Section having Benzene Ring
[Formula 64]
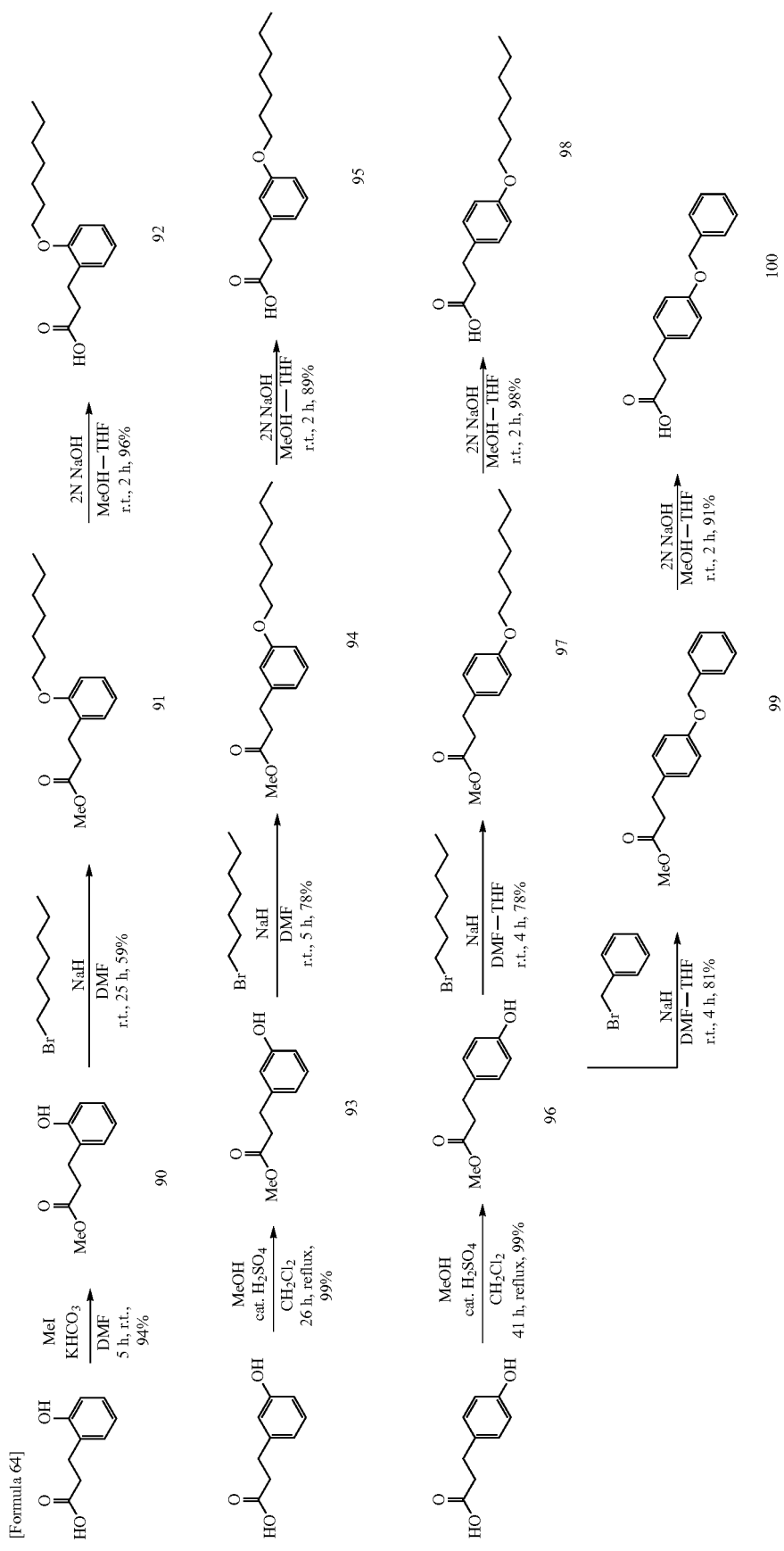

GPR34, P2Y10 and GPR174 Agonistic Activity Assay
[Test Example 1]Assay of Agonistic Activity by TGFα Shedding Assay HEK293 cells were suspended in the Dulbecco's modified Eagle's medium (DMEM) containing 10% fetal bovine serum (FCS) to exist in an amount of $2.0 \times 10^5$ cells/mL, and they were seeded in 60 mm dishes at 4 mL per dish. Transfection of different expression vectors was performed using LipofectAMINE 2000 (Invitrogen) after 24 hours of culture under the presence of 5% $CO_2$. For each 60 mm dish, 1 μg of AP labeled TGFα plasmid vectors were used, and 1 μg of pCAGGS plasmid vectors of mouse GPR34, P2Y10 or GPR174 were used. The plasmid vectors were prepared by methods disclosed in Patent Documents 2 and 5. Note that the AP labeled TGFα is a protein comprising a membrane-bound pro-TGFα whose N terminal end is fused with human placental alkaline phosphatase, and the plasmid vector of the AP labeled TGFα may be produced based on the teaching of Tokumaru et al., J Cell Biol 151, 209-220 (2000). After 24 hours of transfection, the cells were peeled off using trypsin/EDTA, and they were re-suspended in a culture medium to form an amount of $2.0 \times 10^4$ cells/well to be seeded to a 96-well plate. Hanks' Balanced Salt Solution (HBSS, containing 5 mM HEPES) was used for the re-suspended solution when stimulating with the compound. After it was left still for 30 min., subject compounds of various concentrations were added and the solutions were left still for another 1 hour under the presence of 5% $CO_2$. The 96-well plate was subjected to centrifugation (190×g, 3 min.), then 80 μl of supernatant was transferred to a different 96-well plate. A reaction buffer (40 mM Tris-HCl (pH 9.5)) containing 10 mM p-nitrophenyl phosphate (p-NPP) was added in an amount of 80 μL to the supernatant and cells. The OD405 was measured with a micro plate reader (background), then after heating at 37° C. for an hour, OD405 was re-measured. The AP activity for each well was obtained by subtracting the background from the second absorbance and plugging the difference into the following formula.

$$AP \text{ Activity } (\%) = \frac{OD405 \text{ of Supernatant}}{OD405 \text{ of Supernatant} + OD405 \text{ of Cell}}$$ [Formula 65]

In addition, the value obtained by subtracting the AP activity (%) of the non-stimulated group was used in the vertical axis to create a graph. The graphs of the test results for Example 3 (lysoPS sn-1-deoxy sn3 C3-ph-o-OBn-m-Oph) and Example 31 (lysoPS sn-1-OMe sn3 C3-ph-o-OBn-m-Oph) are shown in FIG. 1. From the graphs of FIG. 1, it was confirmed that compounds of Examples 3 and 31 were agonists having selectivity against GPR34.

In addition, the result of the agonistic activity of each compound obtained by comparing the maximum reaction value (Emax) obtained for each test compound of Examples 1 to 26 and 31 with the Emax of the control compound 1 below is shown in Table 2. The obtained activity is shown by plotting the compound concentration and AP activity (%), then representing the activity of the control compound 1 (LPS18:1) as +++, an activity that is 10 folds that of control compound 1 as ++++, an activity that is 100 folds that of control compound 1 as +++++, an activity that is 1/10 as ++, and an activity that is 1/100 as +, and an activity below that as −.

[Formula 66]

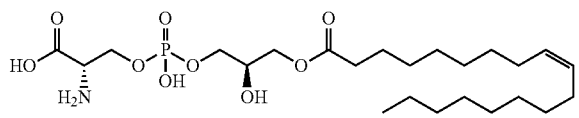

Control Compound 1

TABLE 2

Test Result of TGFα Shedding Assay

| Example | GPR34/LPS2 | P2Y10/LPS2 | GPR174/LPS3 |
|---|---|---|---|
| 1 | ++++ | ++ | +~++ |
| 2 | +++ | ++~+++ | +~++ |
| 3 | +++++ | ++ | − |
| 4 | ++++ | + | − |
| 5 | ++ | + | − |
| 6 | +++++ | + | − |
| 7 | ++ | − | − |
| 8 | +++~++++ | +++ | − |
| 9 | ++++~+++++ | ++~+++ | − |
| 10 | − | ++~+++ | − |
| 11 | − | ++ | − |
| 12 | − | + | − |
| 13 | ++ | −~+ | − |
| 14 | − | + | − |
| 15 | ++ | − | − |
| 16 | +++ | +~++ | − |
| 17 | ++++ | − | − |
| 18 | ++++~+++++ | − | − |
| 19 | − | ++ | − |
| 20 | +++~++++ | + | − |
| 21 | −~++ | ++ | − |
| 22 | +++ | − | − |
| 23 | ++ | ++ | − |
| 24 | +++ | ++~+++ | − |
| 25 | +~++ | +++~++++ | − |
| 26 | +++~++++ | ++ | − |
| 31 | +++++ | +~++ | − |

The invention claimed is:

1. A compound represented by formula (I):

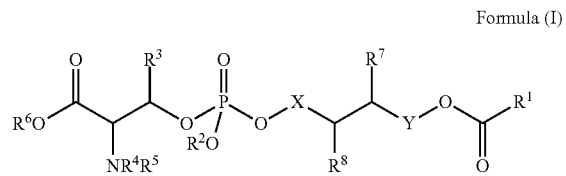

Formula (I)

wherein $R^1$ is $C_{1-30}$ alkyl, $C_{2-30}$ alkenyl, $C_{2-30}$ alkynyl, or a group represented by formula: —($C_{1-15}$ alkylene)-$Q^1$-$Z^1$-($C_{1-15}$ alkylene)-$Z^2$-$Q^2$;

in which $Q^1$ is $C_{3-10}$ cycloalkylene, 5-10 membered heterocyclylene, $C_{6-10}$ arylene, or 5-10 membered heteroarylene, $Q^2$ is a hydrogen atom, $C_{3-10}$ cycloalkyl, 5-10 membered heterocyclyl, $C_{6-10}$ aryl, or 5-10 membered heteroaryl, and $Q^2$ may be substituted with -$Z^3$-$Q^3$, $Q^3$ is $C_{3-10}$ cycloalkyl, 5-10 membered heterocyclyl, $C_{6-10}$ aryl, or 5-10 membered heteroaryl, $Z^1$, $Z^2$, and $Z^3$ are independently selected from the group consisting of an oxygen atom, a sulfur atom, —$NR^9$—, difluoromethylene, and a direct bond, wherein the alkyl, alkenyl, alkynyl, cycloalkylene, heterocyclylene, arylene, heteroarylene, cycloalkyl, heterocyclyl, aryl, and heteroaryl may be independently substituted with one or more substituents selected from halo and hydroxy;

$R^2$ is a hydrogen atom, $C_{1-6}$ alkyl, $C_{7-14}$ aralkyl, or $C_{1-6}$ alkoxy $C_{1-6}$ alkyl;

$R^3$ is a hydrogen atom or $C_{1-6}$ alkyl;

$R^4$ and $R^5$ are independently selected from the group consisting of a hydrogen atom, $C_{1-6}$ alkyl, $C_{7-14}$ aralkyl, formyl, $C_{1-6}$ alkylcarbonyl, arylcarbonyl, $C_{1-6}$ alkoxycarbonyl, $C_{1-6}$ alkoxy $C_{1-6}$ alkyl, and $C_{7-14}$ aralkyloxycarbonyl;

$R^6$ is a hydrogen atom, $C_{1-6}$ alkyl, $C_{1-6}$ alkoxy $C_{1-6}$ alkyl, or $C_{7-14}$ aralkyl;

$R^7$ is a hydrogen atom or $C_{1-6}$ alkyl, $R^8$ is $C_{1-6}$ alkyl, in which the alkyl may be substituted with one or more substituents selected from the group consisting of hydroxy, $C_{1-6}$ alkoxy, $C_{3-10}$ cycloalkyloxy, 5-10 membered heterocyclyloxy, $C_{7-14}$ aralkyloxy, $C_{6-10}$ aryloxy, and 5-10 membered heteroaryloxy, or $R^7$ and $R^8$ together with the carbon atom which they are attached may form a ring, if and only if X is $CH_2$, said ring selected from a $C_{3-10}$ saturated carbocyclic ring, and 5-10 membered saturated or partially-saturated heterocyclic ring;

$R^9$ is a hydrogen atom or $C_{1-6}$ alkyl;

X is $CH_2$ or a direct bond, with the proviso that if X is $CH_2$, $R^7$ and $R^8$ together with a carbon atom which they are attached form a ring; and Y is $CH_2$ or a direct bond, or a salt thereof.

2. The compound according to claim 1, which is represented by formula (Ia):

Formula (Ia)

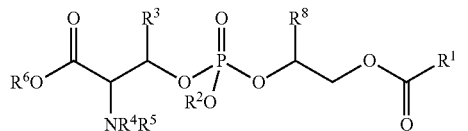

wherein $R^8$ is $C_{1-6}$ alkyl, wherein the alkyl may be substituted with hydroxy, $C_{1-6}$ alkoxy, $C_{3-10}$ cycloalkyloxy, 5-10 membered heterocyclyloxy, $C_{7-14}$ aralkyloxy, $C_{6-10}$ aryloxy, or 5-10 membered heteroaryloxy; and $R^1$, $R^2$, $R^3$, $R^4$, $R^5$, and $R^6$ are as defined in claim 1, or a salt thereof.

3. The compound according to claim 1, which is represented by formula (Ib):

Formula (Ib)

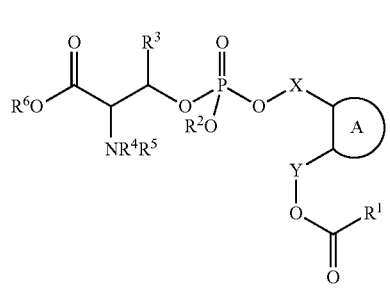

wherein A is a ring selected from $C_{3-10}$ saturated carbocyclic ring, and 5-10 membered saturated or partially-saturated heterocyclic ring; and $R^1$, $R^2$, $R^3$, $R^4$, $R^5$, $R^6$, X, and Y are as defined in claim 1, or a salt thereof.

4. The compound according to claim 3, which is represented by formula (Ic):

Formula (Ic)

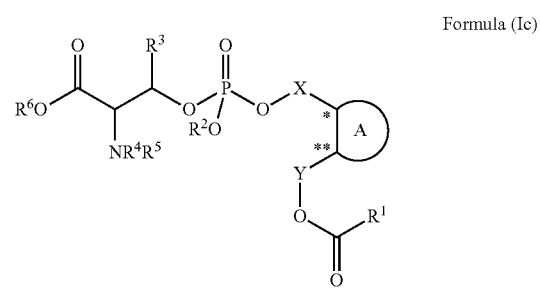

wherein A is a ring selected from the following:

Formula (IIa)

Formula (IIb)

Formula (IIc)

Formula (IId)

Formula (IIe)

Formula (IIf)

Formula (IIg)

Formula (IIh)

Formula (IIi)

wherein p is 1-5, and
* and ** represent the binding positions of side chains on ring A;
or a salt thereof.

5. The compound according to any one of claims 1-4, wherein R³ is a hydrogen atom or methyl.

6. The compound according to claim 1, wherein R¹ is selected from the following:

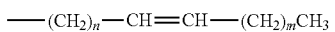
Formula (IIIa)

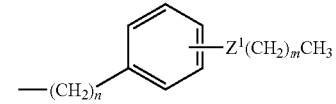
Formula (IIIb)

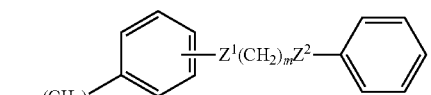
Formula (IIIc)

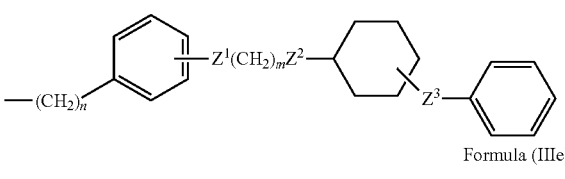
Formula (IIId)

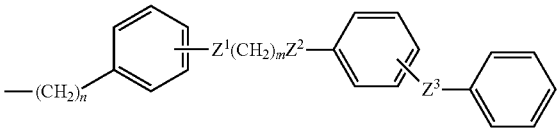
Formula (IIIe)

wherein n and m are independently 1-12, and $Z^1$, $Z^2$, and $Z^3$ are as defined in claim 1, or a salt thereof.

7. A compound selected from:
(9Z)-octadeca-9-enoic acid (2R)-2-[((2S)-2-amino-2-carboxy-ethoxy)-hydroxy-phosphoryloxy]-propyl ester;
(9Z)-octadeca-9-enoic acid (2S)-2-[((2S)-2-amino-2-carboxy-ethoxy)-hydroxy-phosphoryloxy]-propyl ester;
(2S)-2-amino-3-[hydroxyl-((1R)-1-methyl-2-{3-[2-(3-phenoxy-benzyloxy)-phenyl]-propionyloxy}-ethoxy)-phosphoryloxy]-propionic acid;
(9Z)-octadeca-9-enoic acid (2R)-2-[((2S)-2-amino-2-carboxy-ethoxy)-hydroxy-phosphoryloxy]-3-methoxypropyl ester;
(9Z)-octadeca-9-enoic acid (2S)-2-[((2S)-2-amino-2-carboxy-ethoxy)-hydroxy-phosphoryloxy]-3-methoxypropyl ester;
(9Z)-octadeca-9-enoic acid (2R)-2-[((2S)-2-amino-2-carboxy-ethoxy)-hydroxy-phosphoryloxy]-3-ethoxypropyl ester;
(9Z)-octadeca-9-enoic acid (2R)-2-[((2S)-2-amino-2-carboxy-ethoxy)-hydroxy-phosphoryloxy]-3-benzyloxypropyl ester;
(2S)-2-amino-3-(hydroxy{(3R,4R)-4-[3-(2-undecyloxy-phenyl)-propionyloxy]-tetrahydro-pyran-3-yloxy}-phosphoryloxy)-propionic acid;
(2S)-2-amino-3-(hydroxy{(3R,4R)-3-[3-(2-undecyloxy-phenyl)-propionyloxy]-tetrahydropyran-4-yloxyl}-phosphoryloxy)-propionic acid;
(2S)-2-amino-3-(hydroxy{(3S,4S)-4-[3-(2-undecyloxy-phenyl)-propionyloxy]-tetrahydro-pyran-3-yloxy}-phosphoryloxy)-propionic acid;
(2S)-2-amino-3-(hydroxy{(3S,4S)-3-[3-(2-undecyloxy-phenyl)-propionyloxy]-tetrahydro-pyran-4-yloxy}-phosphoryloxy)-propionic acid;
(2S)-2-amino-3-({(3S,4S)-3-[3-(5-tert-butyl-2-undecyloxy-phenyl)-propionyloxy]-tetrahydro-pyran-4-yloxy}-hydroxy-phosphoryloxy)-propionic acid;
(2S)-2-amino-3-[hydroxy((2R,3S)-3-{3-[2-(3-phenoxy-benzyloxy)-phenyl]-propionyloxy}-tetrahydro-pyran-2-ylmethoxy)-phosphoryloxy]-propionic acid;
(2S)-2-amino-3-(hydroxy{(2R,3S)-3-[3-(2-undecyloxy-phenyl)-propionyloxy]-tetrahydro-pyran-2-ylmethoxyl}-phosphoryloxy)-propionic acid;
(9Z)-octadeca-9-enoic acid (2R,3R)-3-[((2S)-2-amino-2-carboxy-ethoxy)-hydroxy-phosphoryloxy]-tetrahydro-pyran-2-ylmethyl ester;
(2S)-2-amino-3-(hydroxy{(2R,3R)-2-[3-(2-undecyloxy-phenyl)-propionylmethoxy]-tetrahydro-pyran-3-yloxy}-phosphoryloxy)-propionic acid;
(2S)-2-amino-3-[hydroxy-((2R,3R)-2-{3-[2-(3-phenoxy-benzyloxy)-phenyl]-propionylmethoxy}-tetrahydropyran-3-yloxy)-phosphoryloxy]-propionic acid;
(2S)-2-amino-3-[hydroxy-((2R,3R)-3-{3-[2-(3-phenoxy-benzyloxy)-phenyl]-propionyloxy}-tetrahydropyran-2-ylmethoxy)-phosphoryloxy]-propionic acid;
(2S)-2-amino-3-(hydroxyl-{(2R,3S)-2-[3-(2-undecyloxy-phenyl)-propionyloxymethyl]-3,6-dihydro-2H-pyran-3-yloxy}-phosphoryloxy)-propionic acid;
(9Z)-octadeca-9-enoic acid (2R,3S)-3-[((2S)-2-amino-2-carboxy-ethoxy)-hydroxy-phosphoryloxy]tetrahydro-pyran-2-ylmethyl ester;
(2S)-2-amino-3-(hydroxy-{(2R,3S)-2-[3-(2-undecyloxy-phenyl)-propionyloxymethyl]-tetrahydro-pyran-3-yloxy}-phosphoryloxy)-propionic acid;
(2S)-2-amino-3-[hydroxy-((2R,3S)-2-{3[2(3-phenoxy-benzyloxy)-phenyl]-propionyloxymethyl}-tetrahydro-pyran-3-yloxy)-phosphoryloxy]-propionic acid;
(9Z)-octadeca-9-enoic acid (2R,3S)-3-[((2S)-2-amino-2-carboxy-ethoxy)-hydroxy-phosphoryloxy]-3,6-dihydro-2H-pyran-2-ylmethyl ester;
(2S)-2-amino-3-[hydroxy-((2R,3S)-2-{3-[2-(3-phenoxy-benzyloxy)-phenyl]-propionyloxymethyl}-3,6-dihydro-2H-pyran-3-yloxy)-phosphoryloxy]-propionic acid;
(2S)-2-amino-3-(hydroxy-{(2R,3R)-2[3-(2-undecyloxy-phenyl)-propionyloxymethyl]-3,6-dihydro-2H-pyran-3-yloxyl}-phosphoryloxy)-propionic acid;
(2S)-2-amino-3-[hydroxy-((2R,3R)-2-{3-[2-(3-phenoxy-benzyloxy)-phenyl]-propionyloxymethyl}-3,6-dihydro-2H-pyran-3-yloxy)-phosphoryloxy]-propionic acid;
(2S,3S)-2-amino-3-[hydroxy-((2R,3S)-3-{3-[2-(3-phenoxy-benzyloxy)-phenyl]-propionyloxy}-tetrahydro-pyran-2-ylmethoxy)-phosphoryloxy]-butyric acid;
(2S,3S)-2-amino-3-[hydroxy-((2R,3R)-3-{3-[2-(3-phenoxy-benzyloxy)-phenyl]-propionyloxy}-tetrahydro-pyran-2-ylmethoxy)-phosphoryloxy]-butyric acid;
(2S,3S)-2-amino-3-[hydroxy-((2R,3S)-2-{3-[2(3-phenoxy-benzyloxy)-phenyl]-propionyloxymethyl}-tetrahydro-pyran-3-yloxy)-phosphoryloxy]-butyric acid;
(2S,3S)-2-amino-3-[hydroxy-((2R,3R)-2-{3-[2-(3-phenoxy-benzyloxy)-phenyl]-propionyloxymethyl}-tetrahydro-pyran-3-yloxy)-phosphoryloxy]-butyric acid; and
(2S)-2-amino-3-[hydroxy-((1R)-1-methoxymethyl-2-{3-[2-(3-phenoxy-benzyloxy)-phenyl]-propionyloxy}-ethoxy)-phosphoryloxyj-propionic acid,
or a salt thereof.

8. The pharmaceutical composition comprising the compound according to claim 1 or a salt thereof.

9. A compound of (2S)-2-amino-3-[hydroxyl(((1R)-1-methoxymethyl-2-{3-[2-(3-phenoxy-benzyloxy)-phenyl]-propionyloxy}-ethoxy)-phosphoryloxy]-propionic acid.

* * * * *